US009150924B2

(12) United States Patent
Shaw et al.

(10) Patent No.: US 9,150,924 B2
(45) Date of Patent: *Oct. 6, 2015

(54) BIN1 AS A PROGNOSTIC MARKER IN CARDIOVASCULAR DISEASE

(71) Applicant: The Regents of the University of California, Oakland, CA (US)

(72) Inventors: Robin Shaw, San Francisco, CA (US); Ting-Ting Hong, San Mateo, CA (US); James Smyth, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/176,985

(22) Filed: Feb. 10, 2014

(65) Prior Publication Data

US 2014/0302502 A1    Oct. 9, 2014

Related U.S. Application Data

(63) Continuation of application No. 13/265,531, filed as application No. PCT/US2010/032282 on Apr. 23, 2010, now abandoned.

(60) Provisional application No. 61/172,608, filed on Apr. 24, 2009.

(51) Int. Cl.
  *G01N 33/566* (2006.01)
  *C12Q 1/68* (2006.01)
  *C07K 14/47* (2006.01)
  *G01N 33/68* (2006.01)

(52) U.S. Cl.
  CPC .......... *C12Q 1/6883* (2013.01); *C07K 14/4716* (2013.01); *C07K 14/4747* (2013.01); *G01N 33/6893* (2013.01); *G01N 2333/4703* (2013.01); *G01N 2800/325* (2013.01); *G01N 2800/56* (2013.01)

(58) Field of Classification Search
  None
  See application file for complete search history.

(56) References Cited

U.S. PATENT DOCUMENTS

| 6,048,702 | A  | * | 4/2000  | Prendergast et al. .......... 435/7.1 |
| 6,410,238 | B1 |   | 6/2002  | Prendergast et al. |
| 6,831,063 | B1 |   | 12/2004 | Prendergast et al. |
| RE39,816  | E  |   | 9/2007  | Stanton et al. |
| 2004/0106954 | A1 |   | 6/2004  | Whitehurst et al. |
| 2004/0241764 | A1 |   | 12/2004 | Galili |
| 2006/0263813 | A1 |   | 11/2006 | Rosenberg et al. |
| 2010/0092983 | A1 | * | 4/2010  | Liew ................................ 435/6 |
| 2011/0008346 | A1 |   | 1/2011  | Duckers |

FOREIGN PATENT DOCUMENTS

| WO | 2010112424 | 10/2010 |
| WO | 2012087437 | 6/2012 |

OTHER PUBLICATIONS

Bodor et al. (1997) "Troponin I Phosphorylation in the Normal and Failing Adult Human Heart" Circulation 96 (5):1495-1500.
Doust et al. (2005) "How well does B-type natriuretic peptide predict death and cardiac events in patients with heart failure: systematic review" BMJ 330(7492):625, 9 pages.
Hama et al. (1995) "Rapid Ventricular Induction of Brain Natriuretic Peptide Gene Expression in Experimental Acute Myocardial Infarction" Circulation 92(6):1558-1564.
Huang et al. (1999) "Cardiac troponin I gene knockout: a mouse model of myocardial troponin I deficiency" Circ Res 84(1):1-8.
Hunkeler et al. (1991) "Troponin I isoform expression in human heart" Circ Res 69(5):1409-1414.
Missov et al. (1997) "Circulating cardiac troponin I in severe congestive heart failure" Circulation 96(9):2953-2958.
Ricchiuti et al. (1997) "Cardiac troponin I and T alterations in hearts with severe left ventricular remodeling" Clin Chem 43(6):990-995.
Tamura et al. (2000) "Cardiac fibrosis in mice lacking brain natriuretic peptide" Proc Natl Acad Sci USA 97 (8):4239-4244.
Westfall & Solaro (1992) "Alterations in myofibrillar function and protein profiles after complete global ischemia in rat hearts" Circ Res 70(2):302-313.
Dalzell et al. (2009) "Novel Biomarkers in Heart Failure: An Overview" Biomark Med 3(5):453-463.
McKenna, "Report of the 1995 World Health Organization/ International Society and Federation of Cardiology Task Force on he Definition and Classification of Cardiomyopatheies" Circulation, 1996, vol. 93, pp. 841-842.
La Baer et al. "So, You Want to Look for Biomarkers (Introduction to the Special Biomarkers Issue)"Journal of Proteome Research, 2005, vol. 4, pp. 1053-1059.
Mayeux et al. "Biomarkers: potential uses and limitations" NeuroRx, 2005, vol. 1, pp. 182-188.
Barth, et al. (2002) "Dissecting interactions between EB1, microtubules and APC in cortical clusters at the plasma membrane" *J. Cell Sci.* 115(Pt. 8):1583-1590.
Bers (2002) "Cardiac excitation-contraction coupling" Nature 415(6868):198-205.
Beuckelmann, et al. (1992) "Intracellular calcium handling in isolated ventricular myocytes from patients with terminal heart failure" *Circulation* 85(3):1046-1055.
Cheng, et al. (1993) "Calcium sparks: elementary events underlying excitation-contraction coupling in heart muscle" *Science* 262(5134):740-744.
Etienne-Manneville & Hall (2003) "Cdc42 regulates GSK-3β and adenomatous polyposis coli to control cell polarity" Nature 421(6924):753-756.
Fabiato (1983) "Calcium-induced release of calcium from the cardiac sarcoplasmic reticulum" *Am. J. Physiol.* 245(1):C1-C14.

(Continued)

*Primary Examiner* — Gary W Counts
(74) *Attorney, Agent, or Firm* — Shweta Chandra; Carol L. Francis; Bozicevic, Field & Francis, LLP

(57) ABSTRACT

The present disclosure provides methods involving use of BIN1 expression levels, in heart tissue, in evaluating the risk of a poor outcome in a patient diagnosed with congestive heart failure. The methods finds use in evaluating patients who are heart transplant candidates as well as in assessing therapy options and efficacy of treatment in congestive heart failure patients.

22 Claims, 22 Drawing Sheets

(56) References Cited

OTHER PUBLICATIONS

GenBank Accession No. EAW88895 "Calcium channel, voltage-dependent, L type, alpha 1C subunit, isoform CRA_a [*Homo sapiens*]" dated Feb. 4, 2010.
GenBank Accession No. EAW88896 "calcium channel, voltage-dependent, L type, alpha 1C subunit, isoform CRA_b [*Homo sapiens*]"dated Feb. 4, 2010.
GenBank Accession No. EAW88897 "calcium channel, voltage-dependent, L type, alpha 1C subunit, isoform CRA_c [*Homo sapiens*]" dated Feb. 4, 2010.
GenBank Accession No. EAW88898 "calcium channel, voltage-dependent, L type, alpha 1C subunit, isoform CRA_d [*Homo sapiens*]" Feb. 4, 2010.
GenBank Accession No. EAW88899 "calcium channel, voltage-dependent, L type, alpha 1C subunit, isoform CRA_e [*Homo sapiens*]" dated Feb. 4, 2010.
GenBank Accession No. EAW88900 "calcium channel, voltage-dependent, L type, alpha 1C subunit, isoform CRA_f [*Homo sapiens*]" dated Feb. 4, 2010.
GenBank Accession No. EAW88901 "calcium channel, voltage-dependent, L type, alpha 1C subunit, isoform CRA_g [*Homo sapiens*]" dated Feb. 4, 2010.
GenBank Accession No. EAW88902 "calcium channel, voltage-dependent, L type, alpha 1C subunit, isoform CRA_h [*Homo sapiens*]" dated Feb. 4, 2010.
GenBank Accession No. EAW88903 "calcium channel, voltage-dependent, L type, alpha 1C subunit, isoform CRA_i [*Homo sapiens*]" dated Feb. 4, 2010.
GenBank Accession No. EAW88904 "calcium channel, voltage-dependent, L type, alpha 1C subunit, isoform CRA_j [*Homo sapiens*]" dated Feb. 4, 2010.
GenBank Accession No. EAW88905 "calcium channel, voltage-dependent, L type, alpha 1C subunit, isoform CRA_k [*Homo sapiens*]" dated Feb. 4, 2010.
GenBank Accession No. EAW88906 "calcium channel, voltage-dependent, L type, alpha 1C subunit, isoform CRA_l [*Homo sapiens*]" dated Feb. 4, 2010.
GenBank Accession No. EAW88907 "calcium channel, voltage-dependent, L type, alpha 1C subunit, isoform CRA_m [*Homo sapiens*]" dated Feb. 4, 2010.
GenBank Accession No. EAW88908 "calcium channel, voltage-dependent, L type, alpha 1C subunit, isoform CRA_n [*Homo sapiens*]" dated Feb. 4, 2010.
GenBank Accession No. EAW88909 "calcium channel, voltage-dependent, L type, alpha 1C subunit, isoform CRA_o [*Homo sapiens*]" dated Feb. 4, 2010.
GenBank Accession No. EAW88910 "calcium channel, voltage-dependent, L type, alpha 1C subunit, isoform CRA_p [*Homo sapiens*]" dated Feb. 4, 2010.
GenBank Accession No. NM_000719.6 "*Homo sapiens* calcium channel, voltage-dependent, L type, alpha 1C subunit (CACNA1C), transcript variant 18, mRNA" dated Dec. 18, 2011.
GenBank Accession No. NM_004305.2 "*Homo sapiens* bridging integrator 1 (BIN1), transcript variant 8, mRNA" dated Aug. 21, 2011.
GenBank Accession No. NM_139343.1 "*Homo sapiens* bridging integrator 1 (BIN1), transcript variant 1, mRNA" dated Aug. 21, 2011.
GenBank Accession No. NM_139344.1 "*Homo sapiens* bridging integrator 1 (BIN1), transcript variant 2, mRNA" dated Aug. 21, 2011.
GenBank Accession No. NM_139345.1 "*Homo sapiens* bridging integrator 1 (BIN1), transcript variant 3, mRNA" dated Aug. 21, 2011.
GenBank Accession No. NM_139346.1 "*Homo sapiens* bridging integrator 1 (BIN1), transcript variant 4, mRNA" dated Aug. 21, 2011.
GenBank Accession No. NM_139347.1 "*Homo sapiens* bridging integrator 1 (BIN1), transcript variant 5, mRNA" dated Aug. 21, 2011.
GenBank Accession No. NM_139348.1 "*Homo sapiens* bridging integrator 1 (BIN1), transcript variant 6, mRNA" dated Aug. 21, 2011.
GenBank Accession No. NM_139349.1 "*Homo sapiens* bridging integrator 1 (BIN1), transcript variant 7, mRNA" dated Aug. 21, 2011.
GenBank Accession No. NM_139350.1 "*Homo sapiens* bridging integrator 1 (BIN1), transcript variant 9, mRNA" dated Aug. 21, 2011.
GenBank Accession No. NM_139351.1 "*Homo sapiens* bridging integrator 1 (BIN1), transcript variant 10, mRNA" dated Aug. 21, 2011.
GenBank Accession No. NP_000710 "voltage-dependent L-type calcium channel subunit alpha-1C isoform 18 [*Homo sapiens*]" dated Dec. 18, 2011.
GenBank Accession No. NP_004296.1 "myc box-dependent-interacting protein 1 isoform 8 [*Homo sapiens*]" dated Nov. 28, 2011.
GenBank Accession No. NP_647593.1 "myc box-dependent-interacting protein 1 isoform 1 [*Homo sapiens*]" dated Dec. 4, 2011.
GenBank Accession No. NP_647594.1 "myc box-dependent-interacting protein 1 isoform 2 [*Homo sapiens*]" dated Nov. 28, 2011.
GenBank Accession No. NP_647595.1 "myc box-dependent-interacting protein 1 isoform 3 [*Homo sapiens*]" dated Dec. 4, 2011.
GenBank Accession No. NP_647596.1 "myc box-dependent-interacting protein 1 isoform 4 [*Homo sapiens*]" dated Nov. 28, 2011.
GenBank Accession No. NP_647597.1 "myc box-dependent-interacting protein 1 isoform 5 [*Homo sapiens*]" dated Nov. 28, 2011.
GenBank Accession No. NP_647598.1 "myc box-dependent-interacting protein 1 isoform 6 [*Homo sapiens*]" dated Nov. 28, 2011.
GenBank Accession No. NP_647599.1 "myc box-dependent-interacting protein 1 isoform 7 [*Homo sapiens*]" dated Nov. 28, 2011.
GenBank Accession No. NP_647600.1 "myc box-dependent-interacting protein 1 isoform 9 [*Homo sapiens*]" dated Dec. 4, 2011.
GenBank Accession No. NP_647601.1 "myc box-dependent-interacting protein 1 isoform 10 [*Homo sapiens*]" dated Dec. 4, 2011.
Gómez, et al. (1997) "Defective excitation-contraction coupling in experimental cardiac hypertrophy and heart failure" *Science* 276(5313):800-806.
Green, et al. (2005) "APC and EB1 function together in mitosis to regulate spindle dynamics and chromosome alignment" *Mol. Biol. Cell* 16(10):4609-4622.
Gwathmey, et al. (1987) "Abnormal intracellular calcium handling in myocardium from patients with end-stage heart failure" *Circ. Res.* 61(1):70-76.
Harding, et al. (1994) "Contractile function and response to agonists in myocytes from failing human heart" *Eur. Heart J.* 15(Suppl. D):35-36.
Hasenfuss (1998) "Alterations of calcium-regulatory proteins in heart failure" *Cardiovasc. Res.* 37(2):279-289.
Hasenfuss, et al. (1999) "Relationship between Na+-Ca2+-exchanger protein levels and diastolic function of failing human myocardium" *Circulation* 99(5):641-648.
Hullin, et al. (1999) "Subunit expression of the cardiac L-type calcium channel is differentially regulated in diastolic heart failure of the cardiac allograft" *Circulation* 100(2):155-163.
Inui, et al. (1987) "Isolation of the ryanodine receptor from cardiac sarcoplasmic reticulum and identity with the feet structures" *J. Biol. Chem.* 262(32):15637-15642.
Lehnart, et al. (2005) "Phosphodiesterase 4D deficiency in the ryanodine-receptor complex promotes heart failure and arrhythmias" *Cell* 123(1):25-35.
Ligon & Holzbaur (2007) "Microtubules tethered at epithelial cell junctions by dynein facilitate efficient junction assembly" *Traffic* 8(7):808-819.
Litwin, et al. (2000) "Dyssynchronous Ca(2+) sparks in myocytes from infarcted hearts" *Circ. Res.* 87(11):1040-1047.
Marx, et al. (2000) "PKA phosphorylation dissociates FKBP12.6 from the calcium release channel (ryanodine receptor): defective regulation in failing hearts" *Cell* 101(4):365-376.
Mewes & Ravens (1994) "L-type calcium currents of human myocytes from ventricle of non-failing and failing hearts and from atrium" *J. Mol. Cell. Cardiol.* 26(10):1307-1320.

(56) References Cited

OTHER PUBLICATIONS

Neufeld & White (1997) "Nuclear and cytoplasmic localizations of the adenomatous polyposis coli protein" *Proc. Natl. Acad. Sci. U.S.A.* 94(7):3034-3039.

Fernando et al. (2009) "Bin1 SRC homology 3 domain acts as a scaffold for myofiber sarcomere assembly" *J Biol Chem* 284(40):27674-27686.

Hong et al. (2010) "BIN1 localizes the L-type calcium channel to cardiac T-tubules" *PLoS Biol* 8(2):e1000312, pp. 1-14.

Sedwick et al. (2010) "Synopsis. BIN1: a protein with great heart" *PLoS Biol* 8(2):e1000311, pp. 1-2.

De Groote, et al. (2005) "The impact of beta-adrenoreceptor genepolymorphisms on survival in patients with congestive heart failure" *Eur. J. Heart Fail.* 7(6):966-973.

Hesse, et al. (2007) "Dilated cardiomyopathy is associated with reduced expression of the cardiac sodium channel Scn5a" *Cardiovasc Res.* 75(3):498-509.

Lee, et al. (2002) "Amphiphysin 2 (Bin1) and T-tubule biogenesis in muscle" *Science* 297(5584):1193-1196.

Muller, et al. (2003) Targeted Disruption of the Murine *Bin1/Amphiphysin II* Gene Does Not Disable Endocytosis but Results in Embryonic Cardiomyopathy with Aberrant Myofibril Formation. *Mol. Cell. Biol.* 23(12):4295-4306.

Wechsler-Reya, et al. (1998) "A role for the putative tumor suppressor Bin1 in muscle cell differentiation" *Mol. Ccell. Biol.* 18(1):566-575.

Birks, et al. (2006) "Left ventricular assist device and drug therapy for the reversal of heart failure" *N Engl. J Med.* 355(18):1873-1884.

Brette & Orchard (2007) "Resurgence of Cardiac T-Tubule Research" *Physiology (Bethesda)* 22:167-173.

Butler, et al. (1997) "Amphiphysin II (SH3P9; BIN1), a member of the amphiphysin/Rvs family, is concentrated in the cortical cytomatrix of axon initial segments and nodes of ranvier in brain and around T tubules in skeletal muscle" *J. Cell Biol.* 137(6):1355-1367.

Chang, et al. (2007) Bin1 Ablation in Mammary Gland Delays Tissue Remodeling and Drives Cancer Progression. *Cancer Res.* 67(1):100-107.

Chang, et al. (2007) Bin1 Ablation Increases Susceptibility to Cancer during Aging, Particularly Lung Cancer. *Cancer Res.* 67(16):7605-7612.

Chen, et al. (2002). L-type Ca2+ channel density and regulation are altered in failing human ventricular myocytes and recover after support with mechanical assist devices. Circ Res *91*, 517-524.

Dipla, et al. (1998) "Myocyte recovery after mechanical circulatory support in humans with end-stage heart failure" *Circulation* 97:2316-2322.

LIMR Link The Newsletter of the Lankenau Institute for Medical Research, Summer 2008. www.limr.org.

Nicot, et al. (2007) Mutations in amphiphysin 2 (BIN1) disrupt interaction with dynamin 2 and cause autosomal recessive centronuclear myopathy. Nature genetics 39, 1134-1139.

Prendergast, et al. (2009) BAR the Door: Cancer Suppression by Amphiphysin-Like Genes. *Biochimica et Biophysica Acta* 1795(1):25-36.

Pessah, et al. (1985) "The calcium-ryanodine receptor complex of skeletal and cardiac muscle" *Biochem. Biophys. Res. Commun.* 128(1):449-456.

Pollack, et al. (1997) "Dynamics of beta-catenin interactions with APC protein regulate epithelial tubulogenesis" *J. Cell Biol.* 137(7):1651-1662.

Schröder, et al. (1998) "Increased availability and open probability of single L-type calcium channels from failing compared with nonfailing human ventricle" *Circulation* 98(10):969-976.

Scriven, et al. (2000) "Distribution of proteins implicated in excitation-contraction coupling in rat ventricular myocytes" *Biophys. J.* 79(5):2682-2691.

Shaw, et al. (2007) "Microtubule plus-end-tracking proteins target gap junctions directly from the cell interior to adherens junctions" *Cell* 128(3):547-560.

Sipido, et al. (1998) "Frequency dependence of Ca2+ release from the sarcoplasmic reticulum in human ventricular myocytes from end-stage heart failure" *Cardiovasc. Res.* 37(2):478-488.

Takahashi, et al. (2004) "Membrane-associated guanylate kinase-like properties of beta-subunits required for modulation of voltage-dependent Ca2+ channels" *Proc. Natl. Acad. Sci. U.S.A.* 101(18):7193-7198.

\* cited by examiner

A

B

Fig. 11A (SEQ ID NO:1)
NM_004305
*Homo sapiens* BIN1 transcript variant 8

```
   1 cgcgcccctc cctcctcgcg gacctggcg tgccggcgcc cggagtggcc ctttaaaagg
  61 cagcttattg tccggagggg gcgggcgggg cccccgtcg ggcgccgacc gcggcctgag gcccggcccc
 121 tcccctctcc ctccctctgt cccccgtcg ctcgctggct agctcgctgg ctcgctcgcc
 181 cgtccggcgc acgctccgcc tccgtcagtt ggctccgctg tcgggtcgc ggcgtggagc
 241 ggcagccggt ctgacgcgc ggccggcgcg ggggctggg gagcgccgc gcaagatctc
 301 cccgcgag agcggcccct gccaccggc gaggcctgcg ccggatggc agagatgggc
 361 agtaaagggg tgacggcggg aaagatcgcc agcaacgtgc agaagaagct cacccgcgcg
 421 caggagaagg ttctccagaa gctgggaag gcagatgaga ccaaggatga gcagtttgag
 481 cagtgcgtcc agaatttcaa caagcagctg acggagggca cccggctgca gaaggatctc
 541 cgacctacc tggcctccgt caaagccatg cacgaggctt ccaagaagct gaatgagtgt
 601 ctgcagagg tgtatgagcc cgattggccc ggcagggatg aggcaaacaa gatcgcagag
 661 aacaacgacc tgctgtggat ggattaccac cagaagctgg tggaccaggc gctgctgacc
 721 atggacacgt acctgggcca gttcccccgac atcaagtcac gcattgccaa gcgggggcgc
 781 aagctggtgg actacgacag tgcccggcac cactacgagt cccttcaaaac tgccaaaaag
 841 aaggatgaag ccaaaattgc caaggccgag gaggagctca gaaagccca gaaggtgttt
 901 gaggagatga atgtggatct gcaggaggag ctgccgtccc tgtgaacag ccgcgtaggt
 961 ttctacgtca acacgttcca gagcatcgcg gcctggagg aaaacttcca caaggagatg
1021 agcaagctca accagaacct caatgatgtg ctgtcggcg tggagaagca acacggagc
1081 aacaccttca cgtcaaggc ccagcccaga aagaaaagta aactgttttc gcggctgcgc
1141 agaaagaaga acagtgacta cgcgccact ctgaagagc agagccctc gcctccagat
1201 ggctccctg ccgccaccc cgagatcaga gtcaaccacg agccagagcc ggccggggg
1261 gccacgccg gggccaccct cccaagtcc ccatctcagc cagcagaggc ctcggaggtg
1321 gcgggtggga cccaacctgc ggctggagcc caggagccag gggacggc ggcaagtgaa
1381 gcagcctcca gctctcttcc tgctgtcgtg gtgagacct tcccagcaac tgtgaatgcc
1441 accgtggagg gcggcagtgg ggccggcgc ttggacctgc ccccaggttt catgttcaag
1501 gtacaggccc agcacgacta cacggccact gacacagacg agctgcagct caaggctggt
1561 gatgtggtgc tggtgatccc cttccagaac cctgaaagagc aggatgaagg ctggctcatg
1621 ggcgtgaagg agagcgactg gaaccagcac aaggagctgg agaagtgccg tggcgtcttc
1681 cccgagaact tcactgagag ggtcccatga cggcggggcc caggcagcct ccgggcgtgt
1741 gaagaacacc tcctcccgaa aaatgtgtgg ttcttttttt tgttttgttt tcgtttttca
1801 tcttttgaag agcaaaggga aatcaagagg agaccccccag gcagaggggc gttctcccaa
```

Fig. 11A Cont.

```
1861 agattaggtc gttttccaaa gagccgcgtc ccggcaagtc cggcggaatt caccagtgtt
1921 cctgaagctg ctgtgtcctc tagttgagtt tctggcgccc ctgcctgtgc ccgcatgtgt
1981 gcctggccgc agggcgggc tggggctgc cgagccacca tgcttgcctg aagcttcggc
2041 cgcgccaccc gggcaagggt cctctttttcc tggcagctgc tgtgggtggg gcccagacac
2101 cagcctagcc tggctctgcc ccgcagacgg tctgtgtgct gtttgaaaat aaatcttagt
2161 gttcaaaaca aatgaaaca aaaaaaaaat gataaaaact ctcaaaaaaa
```

Fig. 11B (SEQ ID NO:2)
GenBank NP_004296
*Homo sapiens*
Bridging integrator 1 (BIN1) isoform 8

```
  1 maemgskgvt agkiasnvqk kltraqekvl qklgkadetk deqfeqcvqn fnkqltegtr
 61 lqkdlrtyla svkamheask klneclqevy epdwpgrdea nkiaenndll wmdyhqklvd
121 qalltmdtyl gqfpdiksri akrgrklvdy dsarhhyesl qtakkkdeak iakaeeelik
181 aqkvfeemnv dlqeelpslw nsrvgfyvnt fqsiagleen fhkemsklnq nlndvlvgle
241 kqhgsntftv kaqprkkskl fsrlrrkkns dnapakgnks psppdgspaa tpeirvnhep
301 epaggatpga tlpkspsqpa easevaggtq paagaqepge taaseaasss lpavvvetfp
361 atvngtvegg sgagrldlpp gfmfkvqaqh dytatdtdel qlkagdvvlv ipfqnpeeqd
421 egwlmgvkes dwnqhkelek crgvfpenft ervp
```

Fig. 12A  (SEQ ID NO:3)
GenBank NM_139350
*Homo sapiens*
BIN1 isoform 9

```
   1 cgcgccctc cctcctcgcg gacctggcgg tgccggcgcc cggagtggcc ctttaaaagg
  61 cagcttattg tcggagggg gcgggcgggg ggcgccgacc gcggcctgag gcccgcccc
 121 tccctctcc ctccctctgt ccccgcgtcg ctcgctggct agctcgctgg ctcgctcgcc
 181 cgtccggcgc acgctccgcc tcgtcagtt ggctccgctg gcctccgcgc ggcgtggagc
 241 ggcagccggt ctgacgcgc ggccggggct ggggctggg agcgccgcgc gcaagatctc
 301 cccgcgcgag agcggccct gccaccgggc gccaacgtgc agcgcgatggc agagatgggc
 361 agtaaagggg tgacggcgg aaagatcgcc agcaacgtgc agaagaagct caccccgcg
 421 caggagaagg ttctccagaa gctggggaag gcagatgaga ccaaggatga gcagtttgag
 481 cagtgcgtcc agaatttcaa caagcagctg acggagggca acggagctgca gaaggatctc
 541 cggacctacc tgcctccgt caaagccatg cacgaggctt ccaagaagct gaatgagtgt
 601 ctgcaggagg tgtatgagcc cgattggccc ggcagggatg aggcaaacaa gatcgcagag
 661 aacaacgacc tgctgtggat ggattaccac cagaagctgg tggaccaggc gctgctgacc
 721 atggacacgt acctgggcca gttcccccgac atcaagtcac gcattgccaa gcgggggcgc
 781 aagctggtgg actacgacag tgcccggcac cactacgagt cccttcaaac tgccaaaaag
 841 aaggatgaag ccaaaattgc caaggccgag gagagctca tcaaagccca gaaggtgttt
 901 gaggagatga tgtggatct gcaggagag ctgcgtccc tgtgaacag ccgcgtaggt
 961 ttctacgtca acacgttcca gagcatcgcg ggcctggagg gcctggagg aaaacttcca caaggagatg
1021 agcaagctca accagaacct caatgatgtg ctggtcggcc tggagaagca acacggagc
1081 aacaccttca cggtcaaggc ccagcaagc gacaacgcgc ctgcaaaagg gaacaagagc
1141 cctttcgcctc cagatggctc ccctgccgcc accccgaga tcagagtcaa ccacgagcca
1201 gagccggccg gcgggcccg gccgggccaa agtcccatc tcagccagca
1261 gaggcctcgg agtggcggg tgggacccaa cctgcgggctg gagcccagga gccaggggag
1321 acgcggcaa gtgaagcagc ctccagctct cttcctgctg tcgtggtgga gaccttccca
1381 gcaactgtga atgcaccgt ggaggggcggc agtgggccg ggcgcttgga cctgcccca
1441 ggtttcatgt tcaaggtaca ggccagcac gactacacgg ccactgacac agacgagctg
1501 cagctcaagg ctggtgatgt ggtgctgtg atccccttcc agaaccttcc agacaggat
1561 gaaggctggc tcatgggcgt gaaggagagc gacttcact gactgaacc agcacaagga gctggagaag
1621 tgccgtggcg tcttcccga gaacttcact gagagggtcc catgacgcg ggcccaggc
1681 agcctccggg cgtgtgaaga acacctcctc ccgaaaaatg tgtggttctt tttttgtt
```

Fig. 12A Cont.

```
1741 tgtttttcgtt tttcatcttt tgaagagcaa agggaaatca agaggagacc cccaggcaga
1801 ggggcgttct cccaaagatt agtcgtttt ccaagagcc gcgtcccggc aagtccggcg
1861 gaattcacca gtgttcctga agctgctgtg tcctctagtt gagttttctgg cgcccctgcc
1921 tgtgcccgca tgtgtgcctg gccgcagggc gggctggggg gctgccgagc caccatgctt
1981 gcctgaagct tcggccgcgc caccccgcgc agggtcctct tttcctggca gctgctgtgg
2041 gtggggccca gacaccagcc tagcctggct ctgccccgca gacggtctgt gtgctgtttg
2101 aaaataaatc ttagtgttca aaacaaaatg aaacaaaaaa aaaatgataa aaactctcaa
2161 aaaaa
```

Fig. 12B (SEQ ID NO:4)
GenBank NP_647600
*Homo sapiens*
BIN1 isoform 9

```
  1 maemgskgvt agkiasnvqk kltraqekvl qklgkadetk deqfeqcvqn fnkqltegtr
 61 lqkdlrtyla svkamheask klneclqevy epdwpgrdea nkiaenndll wmdyhqklvd
121 qalltmdtyl gqfpdiksri akrgrklvdy dsarhyesl qtakkkdeak iakaeeelik
181 aqkvfeemnv dlqeelpslw nsrvgfyvnt fqsiagleen fhkemskIng nlndvlvgle
241 kqhgsntftv kaqpsdnapa kgnkspsppd gspaatpeir vnhepepagg atpgatlpks
301 psqpaeasev aggtqpaaga qepgetaase aassslpavv vetfpatvng tveggsgagr
361 ldlppgfmfk vqaqhdytat dtdelqlkag dvvlvipfqn peeqdegwlm gvkesdwnqh
421 kelekcrgvf penftervp
```

Fig. 13A (SEQ ID NO:5)
GenBank NM_000719
*Homo sapiens*
CaV1.2

```
   1 atggtcaatg agaatacgag gatgtacatt ccagaggaaa accaccaagg ttccaactat
  61 gggagcccac gccccgccca tgccaacatg aatgccaatg cggcagcggg gctgccccct
 121 gagcacatcc ccaccccggg ggctgccctg cgtggccagg cggccatcga cgcagcccgg
 181 caggctaagc tgatggcag cgctggcaat gcgaccatct ccaccgtcag ctccacgcag
 241 cggaagcggc agcaatatgg gaaacccaag aagcaggca gcaccacgc cacacgcccg
 301 ccccgagccc tgctctgcct gaccctgaag aaccccatcc ggaggcctg catcagcatt
 361 gtcgaatgga accatttga aataattatt ttactgacta tttttgccaa ttgtgtgcc
 421 ttagcgatct atattccctt tcagaagat gattccaacg ccaccaattc caacctgaa
 481 cgagtggaat atctcttct cataatttt acggtggaag cgttttaaa agtaatcgcc
 541 tatgactcc tcttcaccc caatgcctac ctccgcaacg gctgaacct actagatttt
 601 ataattgtgg ttgtgggct ttttagtgca atttagaaac aagcaaccaa agcagatggg
 661 gcaaacgctc tcggaggaa aggggccgga tttgatgtga aggcgctgag ggccttccgc
 721 gtgctgcgcc ccctgcgct ggtgtccgga gtcccaagtc tccaggtggt cctgaattcc
 781 atcatcaagg ccatggtcc cctgctcac atcgccctgc ttgtgctgtt tgtcatcatc
 841 atctacgcca tcatcggctt ggagctcttc atggggaaga tgcacaagac ctgctacaac
 901 caggagggca tagcagatgt tccagcagaa gatgacctt cccctgtgc gctggaaacg
 961 ggccacggc ggcagtgcca gaacggcacg gtgtgcaagc ccggctggga tggtcccaag
1021 cacggcatca ccaactttga caacttgcc ttcgccatgc tcacggtgtt ccagtgcatc
1081 accatggagg gctgacgga cgtgctgtac tgggtcaatg atgccgtagg aagggactgg
1141 cccctgatct attttgttac actaatcatc ataggtcat tttttgtact taacttggtt
1201 ctcgtgtgc ttagcggaga gttttccaaa gagaggaga aggccaaggc ccgggagat
1261 ttccagaagc tgcgggaga gcagcagcta gaagaggatc tcaaaggcta cctggattgg
1321 atcactcagg ccgaagacat cgatcctgag aatgaggacg aaggcatgga tgaggagaag
1381 ccccgaaaca tgagcatgcc caccagtgag accgagtccg tcaacaccga aaacgtggct
1441 ggaggtgaca tcgagggaga aactgcggg gccagctggg cggttctgca cccaccggat
1501 aagttcagcc gctactgccg ccggtggaat cggttctgca attttttgca gaaggaagtg ctccaagtca ccgcgccgca
1561 gtcaagtcta atgtcttcta ctgctggtg atttttcctgg tgttcctcaa cacgctcacc
```

Fig. 13A Cont.

```
1621  attgcctctg  agcactacaa  ccagcccaac  tggctcacag  aagtccaaga  cacggcaaac
1681  aaggccctgc  tggccctgtt  cacggcagag  atgctcctga  agatgtacag  cctggcctg
1741  caggcctact  tcgtgtccct  cttcaaccgc  tttgactgct  tcgtcgtgtg  tggcggcatc
1801  ctggagacca  tcctggtgga  gaccaagatc  atgtcccac   tgggcatctc  cgtgctcaga
1861  tgcgtccggc  tgctgaggat  tttcaagatc  acgaggtact  ggaactcctt  gagcaacctg
1921  gtgtccatcc  tgctgcatcc  tgtcgcctcc  atcgcctccc  tgctcctcct  cctcttcctc
1981  ttcatcatca  tcttctccct  cctgggatg   cagctctttg  gaggaaagtt  caactttgat
2041  gagatgcaga  cccggaggag  cacattcgat  aacttccccc  agtccctcct  cactgtgttt
2101  cagatcctga  cggggagga   ctggaattcg  gtgatgtatg  atggatcat   ggcttatggc
2161  ggcccctctt  ttccagggat  gttagtctgt  atttacttca  tcatcctctt  catctgtgga
2221  aactatatcc  tactgaatgt  gttcttggcc  attgctgtgg  acaacctggc  tgatgctgag
2281  agcctcacat  ctgcccaaaa  ggaggaggaa  gaggagaagg  agagaaagaa  gctggccagg
2341  actgccagcc  cagagaagaa  acaagagttg  gtgagaagc   cgcagtggg   ggaatccaag
2401  gaggagaaga  ttgagctacg  atccatcacg  gctgacgag   agtctccacc  cgccaccaag
2461  atcaaacatgg atgacctcca  gcccaatgaa  aatgaggata  agagccctc   cccaaccca
2521  gaaactacag  gagaagagga  tgaggaggag  ccagagatgc  ctgtcggccc  tcgcccacga
2581  ccactctctg  agcttcacct  taaggaaaag  gcagtgccca  tgccagaagc  cagcgcgttt
2641  ttcatcttca  gctctaacaa  caggtttcgc  ctccagtgcc  acgcattgt   caatgacacg
2701  atcttcacca  acctgatcct  cttcttcatt  ctgctcagca  gcatttccct  ggctgctgag
2761  atcctgtccc  agcacacctc  cttcaggaac  catattctgt  tttatttga   tattgtttt
2821  gaccggtcc   agcacattt   tcaccattga  aattgctctg  aagatgactg  cttatgggc  tttcttgcac
2881  accacatcca  aagggtctt   tctgccgaa   ctacttcaac  atcctgacc   tgctgtggt  cagcgtgtcc
2941  ctcatctcct  ttggcatcca  gtccagtgca  atcaatgtcg  tgaagatctt  gcgagtcctg
3001  cgagtactca  ggccctgcg   ggccatcaac  agggccaagg  gctaaagca   tgtgttcag
3061  tgtgtgtttg  tcgccatccg  gaccatcgg   aacatcgtga  ttgtcaccac  cctgctgcag
3121  ttcatgtttt  cctgcatcgg  gtccagctc   ttcaagggaa  agctgtacac  ctgttcagac
3181  agttccaagc  agacagagc   ggaatgcaag  ggcaactaca  tcacgtacaa  agacgggag
3241  gttgaccacc  ccatcatcca  acccgcagc   tgggagaaca  gcaagtttga  ctttgacaat
3301  gttctggcag  ccatgatggc  cctcttcacc  gtctccacct  tcgaagggtg  gccagagctg
3361  ctgtaccgct  ccatcgactc  ccacacgaa   gacaagggcc  ccatctacaa  ctaccgtgtg
3421  gagatctcca  tcttcttcat  catctacatc  atcatcatcg  ccttcttcat  gatgaacatc
```

Fig. 13A Cont.

```
3481 ttcgtgggct tcgtcatcgt agaaccagcg acagtgcgtg gaatacgccc tcaaggcccg gcccctgcgg
3541 gagctggaca agaaccatcc ccaagaacca gcaccagtac aaagtgtggt acgtggtcaa ctccacctac
3601 agtacatcc ccaagaacca gcaccagtac aaagtgtggt acgtggtcaa ctccacctac
3661 ttcgagtacc tgatgttcgt cctcatcctg ctcaacacca tctgcctggc catgcagcac
3721 tacggccaga gctgcctgtt caaatcgcc atgaacatcc tcaacatgct cttcactggc
3781 ctcttcaccg tggagatgat cctgaagctc cgccttgatt gttgtgggta gcattgttga tatagcaatc
3841 gatgcatgaa atacatttga cgccttgatt gttgtgggta gcattgttga tatagcaatc
3901 accgagtaa accagctga acatacccaa tgctctccct ctatgaacgc agaggaaaac
3961 tcccgcatct ccatcacctt cttccgcctg ttccgggtca tgcgtctggt gaagctgctg
4021 agccgtgggg aggcatccg gacgctgctg tggaccttca tcaagtcctt ccaggccctg
4081 ccctatgtgg ccctcctgat cgtgatgctg ttcttcatct acgcggtgat cgggatgcag
4141 gtgttttggga aaattgccct gaatgatacc acagagatca accggaacaa caactttcag
4201 accttccccc aggccgtgct gctcctcttc agtgtgccca cgggaggc ctggcaggac
4261 atcatgctgg cctgcatgcc aggcaagaag tgtgcccag agtccgagcc cagcaacagc
4321 acggagggtg aaacacccttg tggtagcagc tttgctgtct tctacttcat cagcttctac
4381 atgctctgtg ccttcctgat catcaacctc tttgtagctg tcatcatgga caacttttgac
4441 tacctgacaa gggactggtc catccttggt cccaccacc tggatgagtt taaaagaatc
4501 tgggcagagt atgacccctga agccaagggt cgtatcaaac cctggatgt ggtgaccctc
4561 ctccggcgga ttcagccgcc actaggtttt gggaagctgt gccctcaccg cgtggcttgc
4621 aaacgcctgg tctccatgaa catgcctctg aacagcgacg ggacagtcat gttcaatgcc
4681 accctgtttg ccctggtcag gacggcccctg aggatcaaaa cagaaaggaa cctagaacaa
4741 gccaatgagg agctgcgggc gatcatcaag aagatctgga agcggaccag catgaagctg
4801 ctggaccagg tggtgcccc tgcaggtgat gatgaggtca ccgttgcaa gttctacgcc
4861 acgttcctga tccaggagta cttccggaag ttcaagaagc gcaaagagca gggccttgtg
4921 ggcaagccct cccagaggaa cgcgctgtct ctgcaggctg gcttgcgcac actgcatgac
4981 atcggcctg agatccgacg ggccatctct ggagatctca ccgctgagga ggagctggac
5041 aaggccatga aggaggctgt gtccgctgct tctgaagatg acatcttcag gagggccggt
5101 ggcctgttcg gcaaccacgt cagctactac cagcacatc caaagcgacg gccgagcgc cttccccag
5161 acctttcacca ctcagcgccc gctgcacatc aacaaggcgg gcagcagcca gggcgacact
5221 gagtcgccat cccacgagaa gctggtggac tccaccttca cccgagcag ctactcgtcc
```

Fig. 13A Cont.

```
5281 accggctcca acgccaacat caacaacgcc aacaacaccg ccctgggtcg cctccctcgc
5341 cccgccggct acccagcac ggtcagcact gtggagggcc acgggccccc cttgtcccct
5401 gccatccggg tgcaggaggt ggcgtggaag ctcagctcca acaggtgcca ctcccggag
5461 agccaggcag ccatggcggg tcaggaggag acgtctcagg atgagaccta tgaagtgaag
5521 atgaaccatg acacggaggc ctgcagtgag cccagcctgc tctccacaga gatgctctcc
5581 taccaggatg acgaaaatcg gcaactgacg ctcccagagg aggacaagag ggacatccgg
5641 caatctccga agaggggttt cctccgctct gcctcactag gtcgaagggc ctccttccac
5701 ctggaatgtc tgaagcgaca gaaggaccga gggagagaca tctctcagaa gacagtcctg
5761 ccctttgcatc tggttcatca tcaggcattg gcagtggcag gcctgagccc cctcctccag
5821 agaagccatt cccctgcctc attccctagg ccttttgcca cccaccagc cacacctggc
5881 agccgaggct ggccccccaca gccgtcccc accctgcggc ttgagggggt cgagtccagt
5941 gagaaactca acagcagctt cccatccatc cactgcggct cctgggctga gaccaccccc
6001 ggtggcgggg gcagcagcgc cgccggaga gtccggcccg tcccctcat ggtgcccagc
6061 caggctgggg cccccaggag gcagttccac ggcagtgcca gcagcctggt ggaagcggtc
6121 ttgatttcag aaggactggg gcagttttgct caagatccca agttcatcga ggtcaccacc
6181 caggagctgg ccgacgctg cgacatgacc cgacatgacc ataggagaga tggagagcgc ggccgacaac
6241 atcctcagcg ggggcgcccc acagagcccc aatggcgccc tcttaccctt tgtgaactgc
6301 agggacgcgg ggcaggaccg agccggggc gaagaggacg cggctgtgt gcgcgcgg
6361 ggtcgaccga gtgaggagga gctccaggac agcaggtct acgtcagcag cctgtag
```

Fig. 13B          (SEQ ID NO:6)
GenBank NP_000710
*Homo sapiens*
CaV1.2

```
   1 mvnentrmyi peenhqgsny gsprpahanm nanaaaglap ehiptpgaal swqaaidaar
  61 qaklmgsagn atistvsstq rkrqqygkpk kqgsttatrp prallcltlk npirracisi
 121 vewkpfeiii lltifancva laiyipfped dsnatnsnle rveylfliif tveaflkvia
 181 ygllfhpnay lrngwnlldf iivvvglfsa ileqatkadg analgkgag fdvkalrafr
 241 vlrplrlvsg vpslqvvlns iikamvpllh iallvlfvii iyaiiglelf mgkmhktcyn
 301 qegiadvpae ddpspcalet ghgrqcngt vckpgwdgpk hgitnfdnfa famltvfqci
 361 tmegwtdvly wvndavgrdw pwiyfvtlii igsffvlnlv lgvlsgefsk erekakargd
 421 fqklrekqql eedlkgyldw itqaedidpe nedegmdeek prnmsmptse tesvntenva
 481 ggdiegencg arlahrisks kfsrywrrwn rfcrrkcraa vksnvfywlv iflvflntlt
 541 iasehynqpn wltevqdtan kallalftae mlikmyslgl qayfvslfnr fdcfvcggi
 601 letilvetki msplgisvlr cvrllrifki trywnslsnl vaslinsvrs iasllllfl
 661 fiiifsllgm qlfggkfnfd emqtrrstfd nfpqsliltvf qiltgedwns vmydgimayg
 721 gpsfpgmlvc iyfiilficg nyillnvfla iavdnladae sltsaqkeee eekerkklar
 781 taspekkqel vekpavgesk eekielksit adgesppatk inmddlqpne nedkspypnp
 841 ettgeedeee pempvgprpr plselhlkek avpmpeasaf fifssnnrfr lqchrivndt
 901 iftnlilffi llssislaae dpvqhtsfrn hilfyfdivf ttiftieial kmtaygaflh
 961 kgsfcrnyfn ildllvvsvs lisfgiqssa invvkilrvl rvlrplrain rakglkhvvq
1021 cvfvairtig nivivttllq fmfacigvql fkgklytcsd sskqteaeck gnyitykdge
1081 vdhpiiqprs wenskfdfdn vlaammalft vstfegwpel lyrsidshte dkgpiynyrv
1141 eisiffiiyi iiiaffmmni fvgfvivtfq eggeqeyknc eldknqrqcv eyalkarplr
1201 ryipknqhqy kvwyvvnsty feylmfvlil lnticlamqh yggsclfkia mnilnmlftg
1261 lftvemilkl iafkpkhyfc dawntfdali vvgsivdiai tevnpaehtq cspsmnaeen
1321 srisitffrl frvmrlvkll srgegirtll tfpqavllf rcatgeawqd imlacmpgkk capesepsns
1381 vfgkialndt teinrnnnfq tfpqavllf rcatgeawqd imlacmpgkk capesepsns
1441 tegetpcgss favfyfisfy mlcafliinl fvavimdnfd yltrdwsilg phhldefkri
1501 waeydpeakg rikhldvvtl lrriqpplgf gklcphrvac kiwkrtsmkl ldqvvppagd devtvgkfya
1561 tlfalvrtal riktegnleq aneelraiik kiwkrtsmkl ldqvvppagd devtvgkfya
1621 tfliqeyfrk fkkrkeqglv gkpsqrnals lqaglrtlhd igpeirrais gdltaeeeld
```

Fig. 13B Cont.

```
1681 kamkeavsaa seddifrrag glfgnhvsyy qsdgrsafpq tfttqrplhi nkagssqgdt
1741 espsheklvd stftpssyss tgsnaninna nntalgrlpr pagypstvst veghgpplsp
1801 airvqevawk lssnrchsre sqaamagqee tsqdetyevk mnhdteacse pslstemls
1861 yqddenrqlt lpeedkrdir qspkrgflrs aslgrrasfh leclkrqkdr ggdisqktvl
1921 plhlvhhqal avaglspllq rshspasfpr pfatppatpg srgwppqpvp tlrlegvess
1981 eklnssfpsi hcgswaettp ggggssaarr vrpvslmvps qagapgrqfh gsasslveav
2041 liseglgqfa qdpkfievtt qeladacdmt ieemesaadn ilsggapqsp ngallpfvnc
2101 rdagqdragg eedagcvrar grpseeelqd srvyvssl
```

BIN1 AS A PROGNOSTIC MARKER IN CARDIOVASCULAR DISEASE

CROSS-REFERENCE TO RELATED APPLICATIONS

This application claims priority benefit to U.S. provisional application Ser. No. 61/172,608 filed on Apr. 24, 2009 which is hereby incorporated by reference in its entirety.

STATEMENT REGARDING FEDERALLY SPONSORED RESEARCH

This invention was made with government support under Grant No. HL094414 awarded by the NHLBI, National Institutes of Health. The government has certain rights in the invention.

TECHNICAL FIELD

This invention relates to cardiovascular disease and methods to assess the same.

INTRODUCTION

During the last decade, congestive heart failure (CHF) has burgeoned into the most prominent public health problem in cardiovascular medicine. CHF affects close to 20 million people worldwide and approximately 5 million Americans. In the United States alone, about 400,000 new cases of CHF are diagnosed annually and the condition is responsible for approximately 200,000 deaths per year. About a 100,000 patients diagnosed with CHF have end-stage heart failure. Currently, the treatment for these patients with end-stage heart failure is heart transplant. However, only 2000 hearts are available each year for heart transplant. Mechanical assist devices may be used to stabilize patients waiting for a heart transplant. In some cases, mechanical assist devices are being considered as a treatment option rather than a bridge to heart transplant.

There is a need for diagnostic methods for diagnosing cardiac health, and for evaluating treatment options and efficacy of treatment.

SUMMARY

The present disclosure provides methods involving use of BIN1 expression levels in evaluating the risk of a poor outcome in a patient diagnosed with congestive heart failure. The methods find use in evaluating patients who are heart transplant candidates, as well as in determining therapy options and assessing efficacy of treatment in congestive heart failure patients.

Accordingly, the present disclosure provides a method for determining a risk of a poor outcome in a congestive heart failure patient, the method comprising assaying a BIN1 expression level in a heart tissue sample obtained from the patient; and using the BIN1 expression level to determine the risk of a poor outcome in the patient, wherein a decreased BIN1 expression level is positively correlated to an increase in the risk of a poor outcome. Poor outcome can include, for example, cardiac mortality, the need for mechanical device support (e.g., a left ventricular assist device (LVAD) implant), or a left ventricular ejection fraction of less than 25%. In certain embodiments, the congestive heart failure patient has received a heart transplant and the heart tissue sample is from the transplanted heart. In related embodiments, the heart of the congestive heart failure patient is connected to a mechanical assist device. In other embodiments, the patient is undergoing treatment for CHF. In further embodiments, the patient is undergoing immunosuppression therapy. In certain embodiments, a decreased BIN1 expression level compared to a reference BIN expression level is positively correlated to an increase in the risk of a poor outcome.

In exemplary embodiments, the assaying comprises measuring the level of BIN1 mRNA. In certain cases, the assaying comprises measuring the level of BIN1 protein. In yet other embodiments, the method comprises assaying a CaV1.2 expression level and normalizing the BIN1 expression level using CaV1.2 expression level.

The present disclosure also provides a method for determining a risk of a poor outcome in a congestive heart failure patient, the method comprising assaying expression levels of BIN1 and an internal control gene in a heart tissue sample obtained from the patient; determining an Intrinsic Disease Factor (IDF) by calculating a ratio of the internal control gene expression level to the BIN1 expression level; and using the IDF to determine the risk of a poor outcome in the patient, wherein an increased IDF is positively correlated to an increased risk of a poor outcome. In exemplary embodiments, the internal control gene is a housekeeping gene. In other examples, the internal control gene is CaV1.2. In certain embodiments, the assaying comprises measuring the levels of BIN1 and the internal control gene mRNA. In related embodiments, the congestive heart failure patient has received a heart transplant and the heart tissue sample is from the transplanted heart. In alternate embodiments, the heart of the congestive heart failure patient is connected to a mechanical assist device. In related embodiments, the patient is undergoing treatment for CHF. In certain embodiments, the patient is undergoing immunosuppression therapy. In certain embodiments, the IDF ratio of the patient is compared to a reference IDF and an IDF ratio greater than than the reference IDF ratio is indicative of an increased risk of a poor outcome

Confocal image (100×) of isolated human cardiomyocytes stained with BIN1 indicate much less expression of BIN1 and much shallower T-tubule structures defined by BIN1 staining. 3D volume views of WGA-labeled human cardiomyocytes reconstructed from stacks of 100× confocal image frames acquired at a z-step of 0.1 μm reveal a loss of organized T-tubule network in failing human cardiomyocytes.

Figure 5:
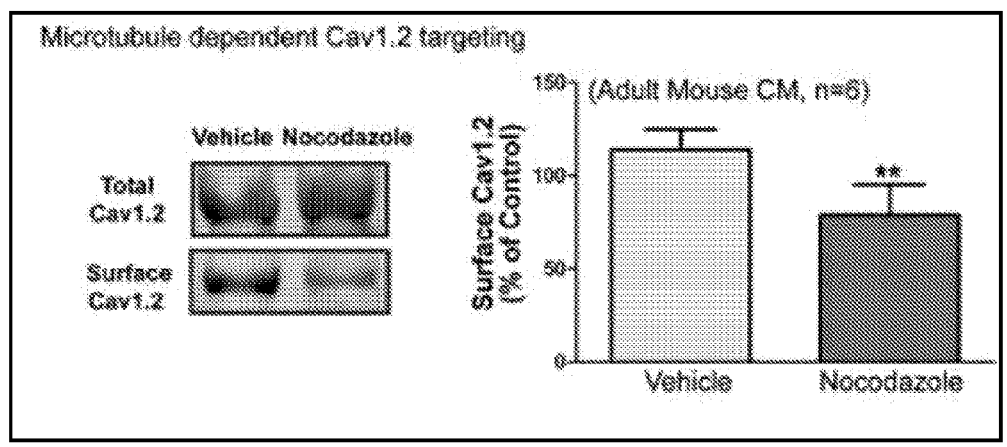

FIG. 5 depicts microtubule dependent forward trafficking of CaV1.2. Surface biotinylation of mouse cardiomyocytes showed that nocodazole reduced surface CaV1.2 expression, indicating a need for microtubules in CaV1.2 trafficking.

Figure 6:
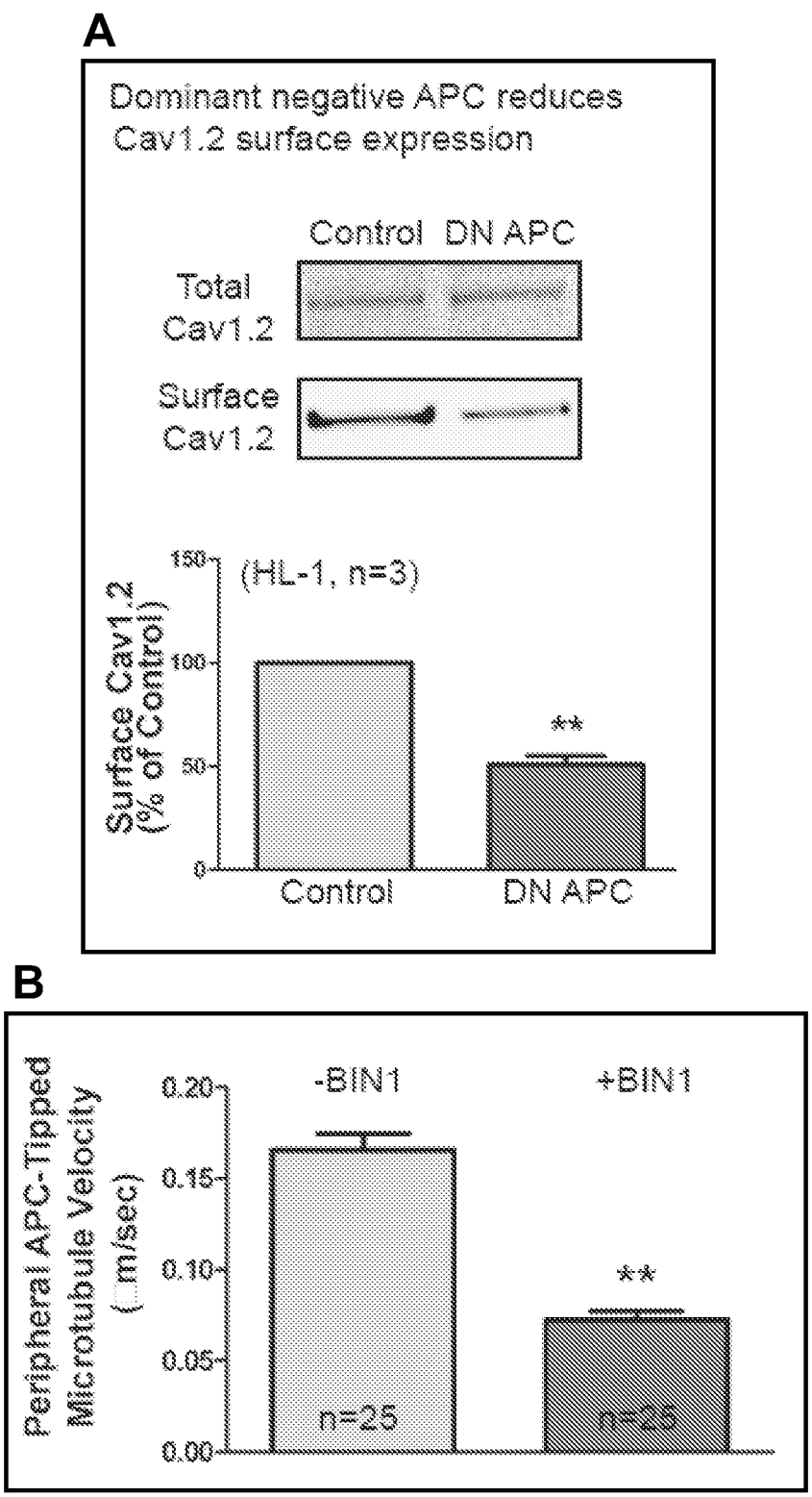

FIG. 6 shows CaV1.2 targeting involves APC-tipped microtubules (A) Surface biotinylation shows dominant negative APC (DN APC) reduced surface CaV1.2 expression in HL-1 cells. (B) APC particles travel a longer distance at a faster velocity when BIN1 is absent.

Figure 7:
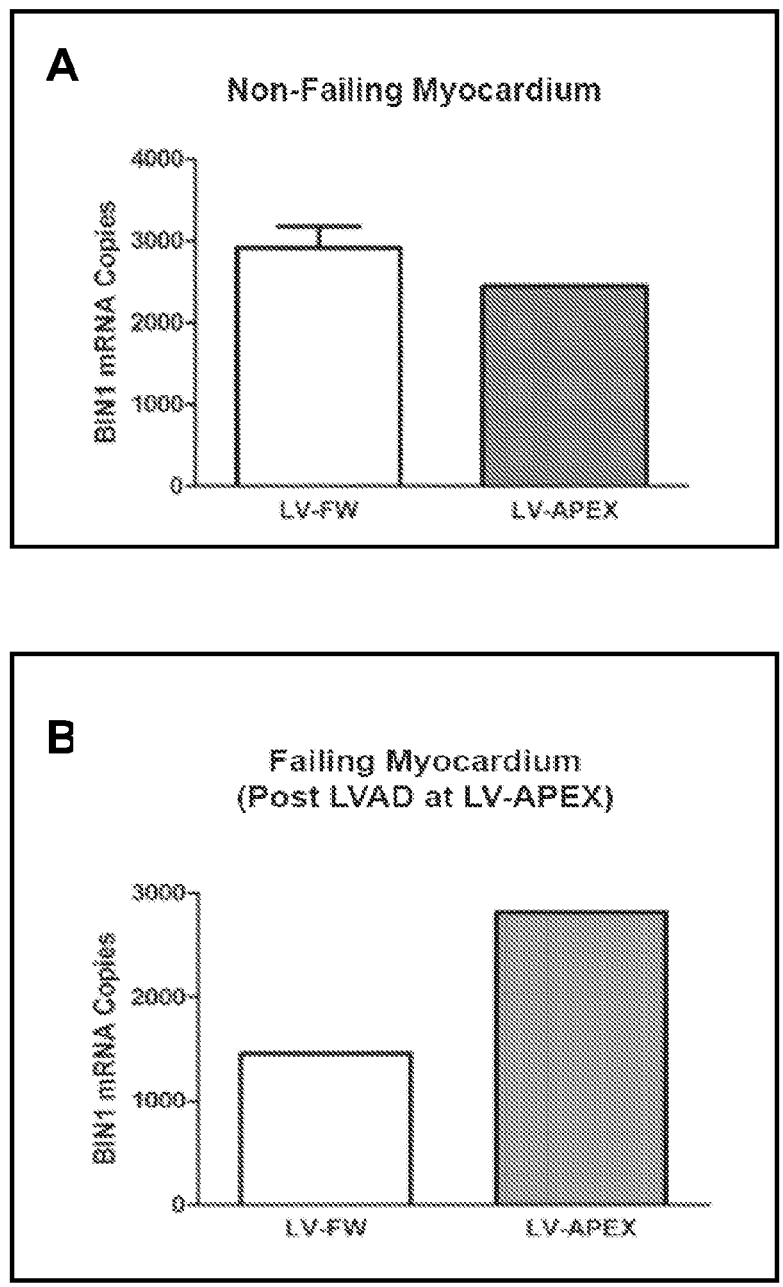

FIG. 7 depicts BIN1 expression levels in non-failing normal heart (A) and in failing heart (B). (A) Non-failing heart from individuals who died for reasons other than heart disease exhibit comparable BIN1 expression levels in left ventricle free wall (LVFW) and LV Apex. (B) Hearts from end stage dilated cardiomyopathy patients who received LVAD at LV Apex show a recovery of BIN1 expression in the LV apex heart tissue (compare to LV-FW).

Figure 8:
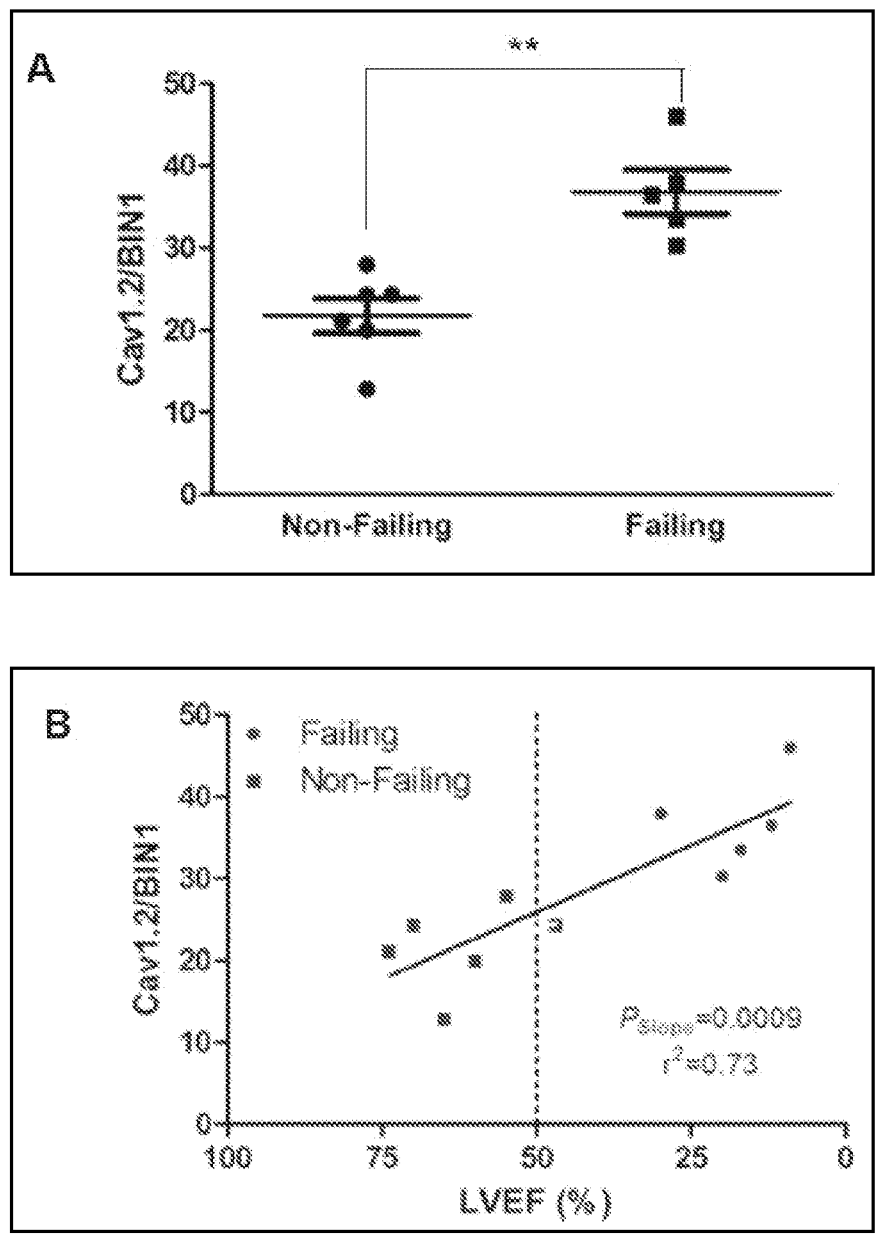

FIG. 8 depicts Intrinsic Disease Factor ($IDF_{CaV}$, measured as a ratio of CaV1.2 mRNA to BIN1 mRNA) for normal and diseased heart. (A) Cardiac $IDF_{CaV}$ for explanted donor hearts. $IDF_{CaV}$ for non-failing heart from individuals who died for reasons other than heart disease (filled circles) and for failing hearts from end staged dilated cardiomyopathy patients (filled squares). Cardiac $IDF_{CaV}$ is significantly higher in hearts with end-stage dilated cardiomyopathy. (B) Cardiac $IDF_{CaV}$ correlates with left ventricular ejection fraction (LVEF). $IDF_{CaV}$ for non-failing heart from normal control individuals who died for reasons other than heart disease (filled squares) and for failing hearts from end-stage dilated cardiomyopathy patients (filled circles).

Figure 9:
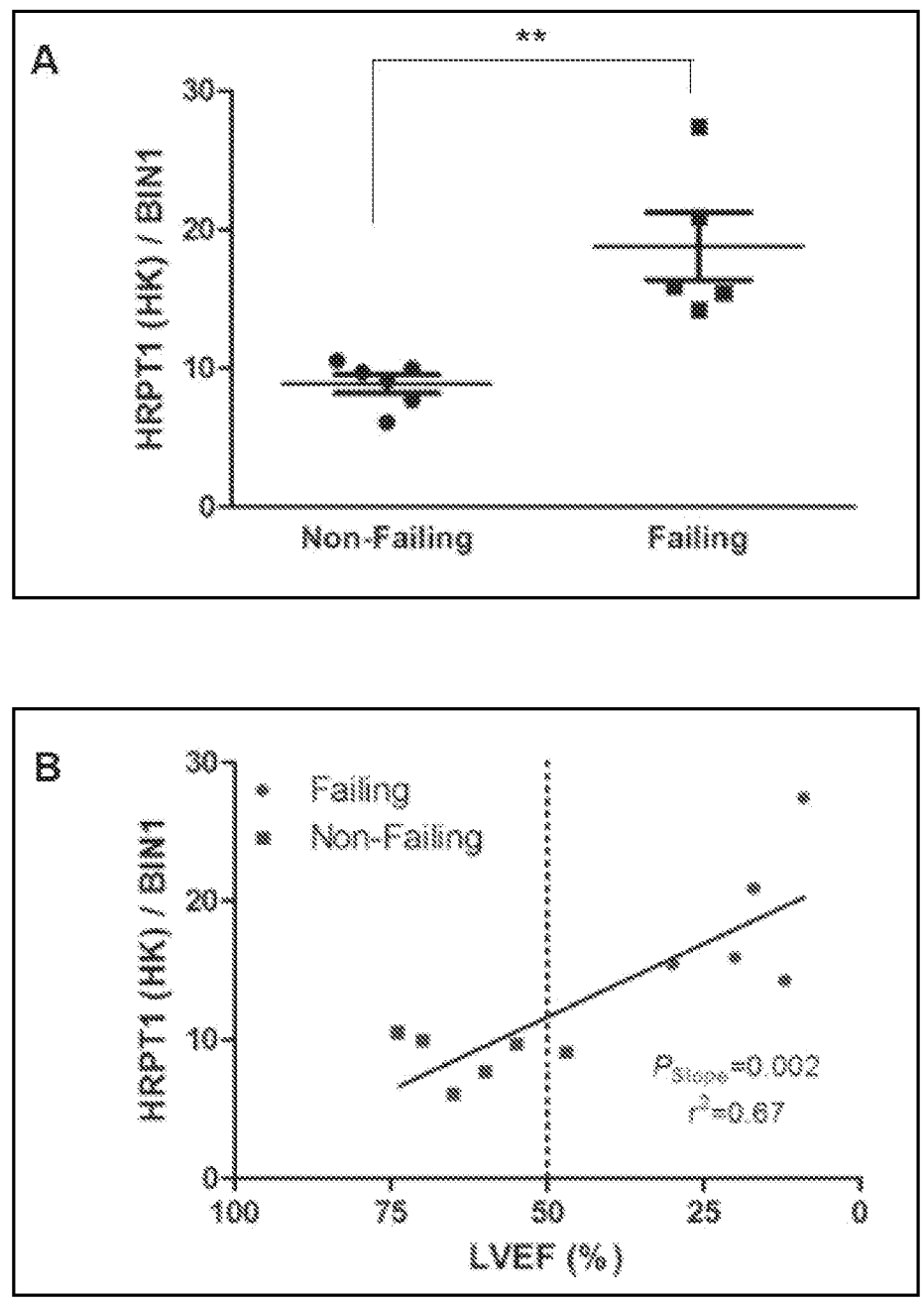

FIG. 9 depicts Intrinsic Disease Factor ($IDF_{HK}$, measured as a ratio of a housekeeping gene mRNA to BIN1 mRNA) for normal and diseased heart. (A) Cardiac IDF ($IDF_{HK}$, measured as a ratio of a HPRT1 mRNA to BIN1 mRNA) for explanted donor hearts. $IDF_{HK}$ for non-failing heart from normal control individuals who died for reasons other than heart disease (filled circles) and for failing hearts from end-stage dilated cardiomyopathy patients (filled squares). Cardiac $IDF_{HK}$ is significantly higher in hearts with end-stage dilated cardiomyopathy. (B) Cardiac $IDF_{HK}$ correlated to left ventricular ejection fraction (LVEF). $IDF_{HK}$ for non-failing heart from normal control individuals who died for reasons other than heart disease (filled squares) and for failing hearts from end-stage dilated cardiomyopathy patients (filled circles).

Figure 10:
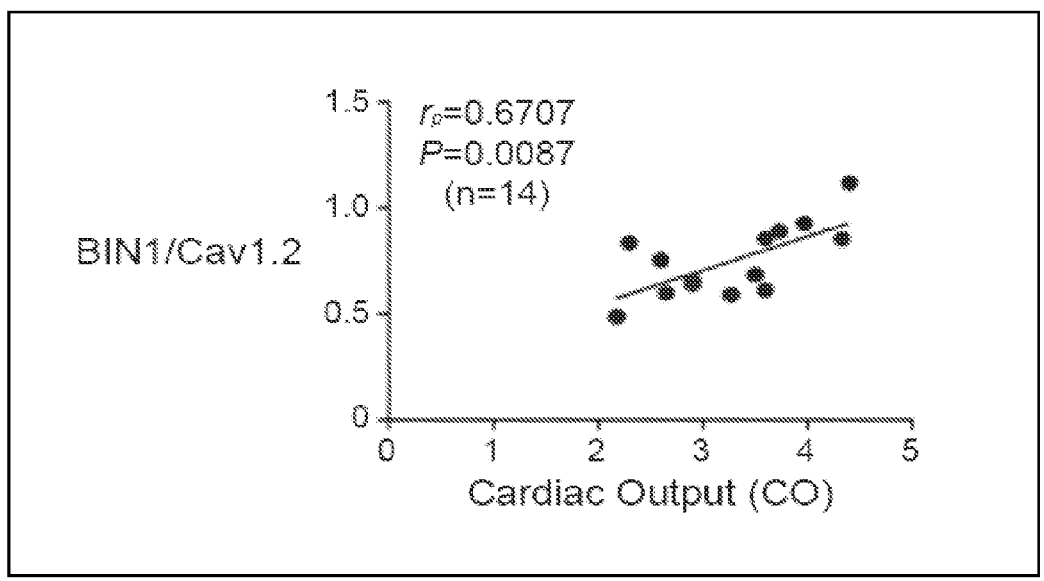

FIG. 10 illustrates the correlation of BIN expression level (normalized to CaV1.2) with cardiac output. The ratio of BIN1 to Cav1.2 is the reciprocal of $IDF_{CaV}$.

FIGS. 11A and 11B provide exemplary BIN1 nucleotide (transcript variant 8) (SEQ ID NO:1) and amino acid (isoform 8) (SEQ ID NO:2) sequences, respectively.

FIGS. 12A and 12B provide exemplary BIN1 nucleotide (transcript variant 9) (SEQ ID NO:3) and amino acid (isoform 9) (SEQ ID NO:4) sequences, respectively.

FIGS. 13A and 13B provide exemplary CaV1.2 nucleotide (SEQ ID NO: 5) and amino acid (SEQ ID NO:6) sequences, respectively.

DETAILED DESCRIPTION OF EXEMPLARY EMBODIMENTS

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a housekeeping gene" includes a plurality of such genes and reference to "the gene" includes reference to one or more genes and equivalents thereof known to those skilled in the art, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "heart failure" or "congestive heart failure" (CHF), and "congestive cardiac failure" (CCF), are used interchangeably herein, and refer to a clinical condition that may result from any structural or functional cardiac disorder that impairs the ability of the heart to fill with or pump a sufficient amount of blood throughout the body to maintain adequate circulation of blood in the tissues of the body or to pump out the venous blood returned to it by the venous circulation.

The term "End-stage heart failure" refers to CHF that is refractory to conventional medical therapy. Patients with end-stage heart failure have a high mortality rate. These patients frequently undergo multiple frequent hospitalizations, intravenous medications, and require surgical therapies such intraaortic balloon pumps, ventricular assist devices, and heart transplant.

The terms "end-stage dilated cardiomyopathy" and "end-stage CHF" are used interchangeably herein.

The term "cardiomyopathy" or "heart muscle disease" refers to the deterioration of the function of the myocardium (i.e., the heart muscle) for any reason. As used herein, the term "cardiomyopathy" includes "extrinsic cardiomyopathies" and "intrinsic cardiomyopathies". In extrinsic cardiomyopathies the primary pathology is outside the myocardium itself, for example, ischemic cardiomyopathy. In intrinsic cardiomyopathies, weakness in the heart muscle is not due to an identifiable external cause, for example, Dilated cardiomyopathy (DCM). In DCM the heart (especially the left ventricle) is enlarged and the pumping function is diminished.

The term "Ischemic cardiomyopathy" refers to cardiomyopathy that results from coronary artery disease, such as atherosclerosis and occlusion of the coronary arteries.

The term "Non-ischemic cardiomyopathy" refers to cardiomyopathy that is not due to coronary artery disease.

The term "prognosis" as used herein refers to a prediction of likelihood of a particular outcome of a disease in a patient, such as likelihood of cardiac mortality in a cardiac disease patient, such as a CHF patient.

"Poor outcome" as used herein in the context of a cardiac patient (e.g., a heart failure patient) refers to an outcome associated with declining heart health. "Poor outcome" includes, for example, in a given time period, a failure of left ventricular ejection fraction (LVEF) to improve or the need for mechanical device support (e.g., a left ventricular assist device (LVAD) implant), or the need for a heart transplant, or cardiac death.

The term "treating" or "treatment" of a condition or disease includes providing a clinical benefit to a subject, and includes: (1) inhibiting the disease, i.e., arresting or reducing the development of the disease or its symptoms, or (2) relieving the disease, i.e., causing regression of the disease or its clinical symptoms.

Overview

The methods of the present disclosure are based on the discovery that decreasing BIN1 expression levels are positively correlated with declining health of cardiac tissue, and thus with an increasing likelihood of a poor outcome in a cardiac disease patient having congestive heart failure (CHF). For example, as BIN1 expression levels in heart tissue decrease relative to a reference BIN1 expression level, such as a normal BIN1 expression level of normal heart tissue or BIN1 expression level from heart tissue of a patient with congestive heart failure who did not show a poor outcome, the risk of cardiac mortality in the patient increases. The term "cardiac mortality", as used herein, refers to patient mortality due to cardiac disease. Accordingly, BIN1 expression can be used as a prognostic marker that is assayed to provide an expression level value that decreases as the health of heart tissue decreases.

The methods disclosed herein also provide for use of a BIN1 expression level to calculate an Intrinsic Disease Factor (IDF), which provides a score that increases in value as heart tissue health declines. IDF is calculated as a ratio of control gene(s) expression to BIN1 expression. Accordingly, IDF is represented by the formula:

$$IDF = [Control/BIN1]$$

wherein "Control" represents an expression value for one or more internal control genes, i.e., a gene(s) which is not significantly differentially expressed in diseased versus normal human heart tissue. Exemplary internal control genes include CaV 1.2, and/or housekeeping genes. Accordingly, increasing IDF values are positively correlated with increasing risk of a poor outcome, i.e., the higher the IDF, the greater the risk of poor outcome (e.g., the greater the risk of, for example, cardiac mortality, requirement for a LVAD implant, a failure for LVEF to improve from severe dysfunction.

BIN1 expression levels can be assayed by detection of a BIN1 gene product, e.g., by detection of mRNA (e.g., by detection of cDNA generated from mRNA in a heart tissue sample) or BIN1 protein. Exemplary methods for assaying BIN1 expression are provided below.

The methods of the present disclosure are described in further detail below.

BIN1

Bridging integrator 1 (BIN1) gene encodes a nucleocytosolic protein which was initially identified as a Myc-interacting protein with features of a tumor suppressor. BIN1 is also known as amphiphysin II, amphiphysin-like, and box dependant MYC interacting protein 1. Alternate splicing of the BIN1 gene results in ten transcript variants encoding different isoforms. Some isoforms of BIN1 are expressed ubiquitously while others show a tissue specific expression. BIN1 isoforms 1-7 are expressed in neurons. Isoform 8 is muscle specific while isoforms 9 and 10 are ubiquitous. Isoforms that are expressed in the central nervous system may be involved in synaptic vesicle endocytosis and may interact with dynanim, synaptojanin, endophilin, and clathrin. Aberrant splice variants expressed in tumor cell lines have also been described.

BIN1 expression can be assayed by detection of one or more of the BIN1 transcript variants and/or isoforms. BIN1 isoform or transcript variant 1 mRNA (NM_139343.1) and isoform 1 protein (NP_647593.1), BIN1 transcript variant 2 mRNA (NM_139344.1) and isoform 2 protein (NP_647594.1), BIN1 transcript variant 3 mRNA (NM_139345.1) and isoform 3 protein (NP_647595.1), BIN1 transcript variant 4 mRNA (NM_139346.1) and isoform 4 protein (NP_647596.1), BIN1 transcript variant 5 mRNA (NM_139347.1) and isoform 5 protein (NP_647597.1), BIN1 variant 6 mRNA (NM_139348.1) and isoform 6 protein (NP_647598.1), BIN1 transcript variant 7 mRNA (NM_139349.1) and isoform 7 protein (NP_647599.1), BIN1 transcript variant 8 mRNA (NM_004305.2) and isoform 8 protein (NP_004296.1), BIN1 transcript variant 9 mRNA (NM_139350.1) and isoform 9 protein (NP_647600.1), and BIN1 transcript variant 10 mRNA (NM_139351.1) and isoform 10 protein (NP_647601.1) sequences are available in the art. In certain embodiments, BIN1 expression may be assayed by detection of BIN1 transcript variant 8 mRNA and/or BIN1 isoform 8 protein. In other embodiments, BIN1 expression may be assayed by detection of BIN1 transcript variant 9 mRNA and/or BIN1 isoform 9 protein. In other embodiments, BIN1 expression is assayed by detection of both BIN1 transcript variant 8 mRNA and BIN1 transcript variant 9 mRNA and/or detection of both BIN1 isoform 8 protein and BIN1 isoform 9 protein. In exemplary embodiments, BIN1 expression may be assayed by detection of BIN1 transcript variant 8 and 9 mRNA, for example, by detection of structural features shared by BIN1 transcript variants 8 and 9 mRNA and/or by detection of structural features shared by BIN1 isoform 8 protein and BIN1 isoform 9 protein.

In general, BIN1 expression levels may be assayed by using reagents that provide for detection of structure features shared by gene products of the various BIN1 transcript variants/isoforms, e.g., by using primers and/or probes that provide for detection of a region of BIN1 mRNA common to all transcript variants of BIN1 or an antibody that binds an epitope(s) shared by BIN1 isoforms.

Internal Controls

A variety of different internal controls can be used in connection with the assay methods described herein. In general, a gene that is known not to be significantly differentially expressed in heart tissue of a CHF patient and normal heart tissue may be used as an internal control. The following provides exemplary internal control genes which can be assayed.

CaV 1.2

CACNA1C encodes Cav1.2, an alpha-1 subunit of a voltage-dependent calcium channel. Amino acid sequence of *Homo sapiens* CACNA1c polypeptides are known in the art. See, e.g., GenBank Accession No. NP_000710. Amino acid sequences of *Homo sapiens* CACNA1C isoforms CRA_a through CRA_p are found under GenBank Accession Nos. EAW88895 (isoform CRA_a); EAW88896 (isoform CRA_b); EAW88897 (isoform CRA_c); EAW88898 (isoform CRA_d); EAW88899 (isoform CRA_e); EAW88900 (isoform CRA_f); EAW888901 (isoform CRA_g); EAW888902 (isoform CRA_h); EAW888903 (isoform CRA_i); EAW888904 (isoform CRA_j); EAW888905 (isoform CRA_k); EAW888906 (isoform CRA_l); EAW888907 (isoform CRA_m); EAW888908 (isoform CRA_n); EAW888909 (isoform CRA_o); and EAW888910 (isoform CRA_p). Corresponding nucleotide sequences (e.g., nucleotide sequences encoding CaV1.2) are known in the art. See, e.g., GenBank Accession No. NM_000719 (encoding CaV1.2 having the amino acid sequence provided in GenBank Accession No. NP_000710).

In general, CaV1.2 expression levels may be assayed by using reagents that provide for detection of structure features shared by gene products of the various CaV1.2 transcript variants/isoforms, e.g., by using primers and/or probes that provide for detection of a region of CaV1.2 mRNA common to all transcript variants of CaV1.2 or an antibody that binds an epitope(s) shared by CaV1.2 isoforms. In certain embodiments, CaV1.2 transcript variant 18 (NM_000719.6) may be assayed.

Cav1.2 expression level may be assayed by detection of CaV1.2 mRNA or protein.

Housekeeping Genes

A housekeeping gene is typically a constitutively expressed gene that is transcribed at a relatively constant level in a tissue of interest across conditions being evaluated herein. The housekeeping genes typically encode gene products that facilitate maintenance of cells, such nucleic acid synthesis, metabolism, cytoskeletal structure, and the like. In general, expression level of a housekeeping gene is not substantially differentially expressed between a failing and a non-failing heart tissue. Examples of housekeeping genes include HPRT, GAPDH, β-actin, tubulin, ubiquitin, RPL13A, PP1A, and EEF1A1 and the like.

Housekeeping gene expression level may be assayed by detection of mRNA or protein.

Methods for Assaying Gene Expression

Gene expression may be assayed by quantifying the levels of BIN1 mRNA or polypeptide. Commonly used methods known in the art for the quantification of mRNA expression in a sample may be employed for assaying BIN1 expression levels. Such methods include PCR-based methods, such as reverse transcription polymerase chain reaction (RT-PCR) (Weis et al., Trends in Genetics 8:263-264 (1992)), in situ hybridization (Parker & Barnes, Methods in Molecular Biology 106:247-283 (1999)), northern blotting, and RNAse protection assays (Hod, Biotechniques 13:852-854 (1992)). Alternatively, antibodies may be employed that can recognize sequence-specific duplexes, including DNA duplexes, RNA duplexes, and DNA-RNA hybrid duplexes or DNA-protein duplexes. The levels of BIN1 polypeptide may be detected by quantitative western-blot, immunoprecipitation, etc. In certain cases, BIN-1 expression levels may be determined by in situ assays, for example, by hybridizing labeled probes specific to BIN-1 mRNA or using a BIN-1 antibody.

In general, BIN1 gene expression may be assayed in a sample of heart tissue from a patient. The heart tissue is usually a biopsy sample. The heart tissue may be biopsied in a variety of procedures, well known to one of skill in the art. The heart tissue may be processed by any method compatible with the assay to be conducted. For example, the heart tissue may be freshly obtained, frozen (e.g., flash frozen), formalin fixed, paraffin embedded, or any suitable combination thereof. In general, the method may be selected so as to avoid substantial degradation of the analyte to be assayed (e.g., proteins and/or mRNA) in the heart tissue.

Quantitative Reverse Transcriptase PCR (qRT-PCR)

The first step is the isolation of mRNA from a sample. The starting material is typically total RNA isolated from the heart tissue of a patient diagnosed with congestive heart failure and, optionally, from corresponding normal tissue as a control. Heart tissue may be obtained fresh or may be frozen or archived paraffin-embedded and fixed (e.g. formalin-fixed) tissue sample.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A67 (1987), and De Andrés et al., *BioTechniques* 18:42044 (1995). In particular, RNA isolation can be performed using a purification kit, buffer set and protease from commercial manufacturers, such as Qiagen, according to the manufacturer's instructions. For example, total RNA can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from heart tissue can be isolated, for example, by cesium chloride density gradient centrifugation.

Typically, the first step in RT-PCR is the reverse transcription of the RNA template into cDNA, followed by its exponential amplification in a PCR reaction. A number of reverse transcriptases may be used, including but not limited to, Avian Myeloblastosis Virus Reverse Transcriptase (AMV-RT), Moloney Murine Leukemia Virus Reverse Transcriptase (MMLV-RT), reverse transcriptase from human T-cell leukemia virus type I (HTLV-I), bovine leukemia virus (BLV), Rous sarcoma virus (RSV), human immunodeficiency virus (HIV) and *Thermus thermophilus* (Tth). The reverse transcription step is typically primed using specific primers, random hexamers, or oligo-dT primers, depending on the circumstances and the goal of RT-PCR. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, Taq- Man® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700 Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700 Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as $C_t$, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986-994 (1996).

It is desirable to correct for (normalize away) both differences in the amount of RNA assayed and variability in the quality of the RNA used. Therefore, the assay typically incorporates analysis of the expression of certain reference genes (or "normalizing genes"), including well known housekeeping genes, such as GAPDH, HPRT1, ubiquitin, etc.

Alternatively, normalization can be based on the mean or median signal ($C_t$) of all of the assayed genes or a large subset thereof (often referred to as a "global normalization" approach). On a gene-by-gene basis, measured normalized amount of a patient heart tissue mRNA may be compared to the amount found in a corresponding normal heart tissue. See M. Cronin, et al., Am. Soc. Investigative Pathology 164:35-42 (2004).

Design of Primers and Probes

Primers and probes (e.g., for use in PCR amplification-based methods) can be designed based upon exon sequence or upon intron sequences present in the gene to be amplified. Accordingly, the first step in the primer/probe design is the delineation of a target exon or intron sequence within the gene of interest. This can be done by publicly available software, such as the DNA BLAT software developed by Kent, W. J., *Genome Res.* 12(4):656-64 (2002), or by the BLAST software including its variations. Subsequent steps follow well established methods of PCR primer and probe design.

In order to avoid non-specific signals, repetitive sequences within the target sequence of the gene can be masked when designing the primers and probes. This can be easily accomplished by using the Repeat Masker program available online through the Baylor College of Medicine, which screens DNA sequences against a library of repetitive elements and returns a query sequence in which the repetitive elements are masked. The masked sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386).

The factors to be considered in PCR primer design can include primer length, melting temperature (Tm), G/C content, specificity, complementary primer sequences, and 3'-end sequence. In general, optimal PCR primers are 17-30 bases in length, and contain about 20-80% G+C bases, (e.g., about 50-60% G+C bases). Tm's between 50° C. and 80° C., e.g. about 50° C. to 70° C. are typically preferred.

For further guidelines for PCR primer and probe design see, Dieffenbach, C. W. et al., "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T. N. Primerselect: Primer and probe design. *Methods Mol. Biol.* 70:520-527 (1997), the entire disclosures of which are hereby expressly incorporated by reference.

Microarrays

Microarray technology may be used to detect differential expression of BIN1 in diseased heart tissue and normal heart tissue. In this method, polynucleotide sequences of interest (including cDNAs and oligonucleotides) are plated, or arrayed, on a microchip substrate. The arrayed sequences are then hybridized with specific DNA probes from cells or tissues of interest. Similar to the RT-PCR method, the source of mRNA typically is total RNA isolated from patient heart tissue, and optionally corresponding normal heart tissue.

Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pair wise to the array. The relative abundance of the transcripts from the two sources corresponding to each specified gene is thus determined simultaneously. Microarray methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GenChip technology, or Incyte's microarray technology.

The arrayed oligonucleotides may include oligonucleotides which hybridize to a specific region of BIN1 nucleic acid. In certain embodiments, multiple copies of a first oligonucleotide which specifically hybridizes to a first region of BIN1 nucleic acid are arrayed. In certain embodiments, multiple copies of first and a second oligonucleotide which specifically hybridize to a first and a second region of BIN1 nucleic acid, respectively are arrayed, and so on. In certain embodiments, the BIN1 expression level is determined by mean values of the signal from each of these oligonucleotides. In certain embodiments, the array may also include oligonucleotides which specifically hybridize to nucleic acid of a normalizing gene, such as a housekeeping gene or other genes known not to be significantly differentially expressed in diseased versus normal heart tissue, for example, CaV 1.2.

Immunodetection

Immunohistochemical methods may also be suitable for detecting the expression levels of BIN1. Thus, antibodies or antisera, such as, polyclonal antisera and monoclonal antibodies specific for BIN1 may be used to assess BIN1 expression. The antibodies can be detected by direct labeling of the antibodies themselves, for example, with radioactive labels, fluorescent labels, hapten labels such as biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. In certain examples, BIN1 expression in a heart sample from a patient may be compared to BIN1 expression in a normal heart sample. Immunohistochemistry protocols and kits are well known in the art and are commercially available.

In certain cases, the amount of BIN1 protein present in a heart tissue sample may be determined by a western blot. For example, proteins present in the whole cell lysate from a heart sample may be separated by SDS-PAGE; the separated proteins transferred to a nitrocellulose membrane; BIN1 detected by using an antibody or antiserum specific for BIN1. At least one normalizing protein, for example, Cav1.2 or a housekeeping protein such as GAPDH or β-actin may also be detected simultaneously or in parallel and used to normalize the BIN protein expression levels. In alternative embodiments, BIN1 expression level may be determined by performing a BIN1 immunoprecipitation using an excess of anti-BIN1 antibody, followed by separation of the immunoprecipitate by SDS-PAGE; the separated proteins transferred to a nitrocellulose membrane; and detected by staining the gel, e.g., by Coommassie Blue or silver staining. Immunoprecipitation of a control protein such as GAPDH or ubiquitin may also be carried out either simultaneously or in parallel. Optionally, the same procedure may be carried out on corresponding normal heart tissue.

Use of BIN1 Expression Levels in Prognosis of Risk of Cardiac Mortality

BIN1 expression can be used as a prognostic marker that is assayed to predict the risk of a poor outcome in a CHF patient. A decrease in BIN1 expression level is positively correlated with an increase in the risk of a poor outcome such as cardiac mortality. BIN1 expression level may be used to calculate an Intrinsic Disease Factor (IDF), which provides a score that increases in value as the risk of a poor outcome such as cardiac mortality increases.

Use of BIN1 Expression Levels

The method can involve assaying BIN1 expression level in a heart tissue sample from a patient diagnosed with CHF. Analysis of BIN1 can involve comparison of the BIN expression level to a reference BIN1 expression level, for example a normal BIN1 expression level or a BIN1 expression level known to be indicative of a low risk of a poor outcome.

The reference BIN1 expression level may be a BIN1 expression level known to be indicative of a low risk of a poor outcome. The reference BIN1 expression level may be the BIN1 expression level in a CHF patient (or an average of BIN1 expression levels of a group of patients) who is known not to have a poor outcome, such as cardiac mortality, LVAD implant, or LVEF that fails to improve. A low BIN1 expression level compared to the reference BIN1 expression level indicates that the patient has an increased likelihood of a poor outcome. In contrast, a BIN1 expression level equal to or greater than the reference value indicates that the patient has a decreased likelihood of a poor outcome.

A normal BIN1 expression level generally refers to a BIN1 expression level in non-failing heart muscle. A normal BIN1 expression level can be determined from BIN1 expression levels of non-failing heart tissue obtained from an individual whose heart function was deduced to be normal from an examination of the gross morphology of the heart, left ventricular ejection fraction, cardiac catheterization, and/or from lack of heart related condition in the individual medical record, and the like.

A low BIN1 expression level compared to a reference BIN expression level indicates that the patient has an increased likelihood of cardiac mortality. In general, at least a 20% reduction in BIN1 expression level compared to a normal BIN expression level indicates that the patient has an increased likelihood of cardiac mortality. Thus, a patient with a 20% reduction, a 30% reduction, a 40% reduction, a 50% reduction, a 75% reduction, or more, in BIN1 expression level compared to a normal BIN expression level has an increased risk of cardiac mortality.

Usually, the BIN1 mRNA or protein level is normalized with reference to an internal control, such as a housekeeping gene or a gene known not to change in CHF, such as CaV1.2. In certain embodiments, the BIN1 mRNA or protein level is normalized with reference to a plurality of internal controls, such as a plurality of housekeeping genes. In general, when a plurality of internal controls is used the mean expression level of these controls is used for normalizing BIN1 expression level.

BIN 1 expression levels may be used to predict the risk of a poor outcome over a period of time following the assessment of the BIN1 expression level, for example, the risk of a poor outcome for the CHF patient over the next 1 day-24 months, e.g., 6 months-18 months, such as, over the next 6 months-12 months, or 12 months-18 months.

Intrinsic Disease Factor (IDF)

Intrinsic disease factor (IDF) is calculated as a ratio of control gene(s) expression to BIN1 expression. Accordingly, IDF is represented by the formula:

$$IDF = [Control/BIN1]$$

wherein "Control" represents an expression value for one or more internal control genes, i.e., a gene(s) which is not significantly differentially expressed in diseased versus normal human heart tissue. Exemplary internal control genes include CaV 1.2, and/or housekeeping genes.

$IDF_{CaV}$ refers to IDF calculated as a ratio of Cav1.2 expression to BIN1 expression and is represented by the formula:

$$IDF_{CaV} = [Cav1.2/BIN1]$$

$IDF_{HK}$ refers to IDF calculated as a ratio of housekeeping (HK) gene(s) expression to BIN1 expression and is represented by the formula:

$$IDF_{HK} = [HK/BIN1]$$

Exemplary housekeeping genes that may be used to determine $IDF_{HK}$ have been described above. Expression level of a single housekeeping gene may be used to calculate $IDF_{HK}$. Alternatively, the mean expression level of two or more housekeeping genes may be used to calculate $IDF_{HK}$.

Analysis of IDF can involve comparison of the IDF value to a reference IDF value, e.g., a normal IDF value or an IDF value indicative of a low risk of a poor outcome. A normal IDF value is the ratio of control gene(s) expression to BIN1 expression in non-failing heart tissue. Non-failing heart tissue is obtained from an individual whose heart function was deduced to be normal from an examination of one or more parameters of heart health, such as, the gross morphology of the heart, left ventricular ejection fraction (LVEF), cardiac catheterization, and/or from lack of heart related condition in the individual medical record, etc. For example, a normal heart tissue has a LVEF of 55% or more.

A decrease in BIN1 expression and accordingly increasing IDF values are positively correlated with increasing risk of cardiac mortality, i.e., the higher the IDF, the greater the risk of cardiac mortality. For example, IDF value of greater than about 1.5 times a normal IDF value is indicative of increased risk of cardiac mortality. Thus, an IDF value greater than about 1.5 times, or greater than about 2 times, or greater than about 3 times, or greater than about 4 times, or greater than about 5 times, or more, the normal IDF value is indicative of increased risk of cardiac mortality.

BIN1 expression levels and IDF values for a patient can also be assessed relative to a threshold value. A "threshold value" or "risk threshold value" is a value which can be used to distinguish a relatively high risk of poor outcome from a relatively low risk of a poor outcome. For example, in most cases the threshold value is an approximate value above which risk of a poor outcome is relatively higher, and below which risk of a poor outcome is relatively lower. For example, a normalized BIN1 expression level of about 0.65 represents a threshold value, where cardiac patients having a normalized BIN1 expression level lower than threshold value have a relatively increased risk of a poor outcome, and cardiac patients having a normalized BIN1 expression level greater than or equal to this threshold value have a relatively decreased risk of poor outcome.

BIN1 expression levels and/or IDF value may be used to predict the risk of a poor outcome over a period of time following assessment, for example, the risk of a poor outcome for the CHF patient over the next e.g., 6 months-18 months, such as, over the next 6 months-12 months, or 12 months-18 months.

Clinical Applications

Determination of BIN1 expression level and/or IDF value in heart tissue from a CHF patient may be used to assign a priority level to the patient for receiving a heart transplant, to facilitate assessing response to CHF treatment, and/or to guide modification of a treatment plan.

In general, the lower the BIN1 expression, and/or the higher the IDF value, the higher the likelihood of poor cardiac recovery and hence the patient is assigned a high priority level for receiving a heart transplant. Alternatively, if a CHF patient has a normal or near normal BIN expression level, the expectation is that the heart has a good chance to recover, and the patient might be assigned a low priority level for receiving a heart transplant. In general, the lower the BIN1 expression level and/or the higher the IDF value, the higher is the priority level of the patient for receiving a heart transplant.

Similarly, in patients with only moderately decreased BIN1 expression and/or moderately increased IDF value, there would be increased priority of placing the patient on a left ventricular assist device to help the patient recover. Removal of the left ventricular assist device could be timed with normalization of BIN expression and/or IDF value. A further decrease of BIN1 expression or increase of IDF value despite the left ventricular assist device would indicate listing the patient for heart transplant.

A determination of a risk of cardiac mortality may be used to assess efficacy of CHF treatment and to determine a change to treatment strategy. A CHF patient may be undergoing treatment by, for example, surgery, mechanical assist device, heart transplant, drug therapy, such as, angiotensin-converting enzyme (ACE) inhibitors, angiotensin-receptor blockers (ARBs), beta blockers, diuretics, etc. The efficacy of a CHF treatment may be assessed by assaying for BIN expression level and/or IDF value. In general, a low BIN1 expression, and/or a high IDF value, indicates a high likelihood of a cardiac failure and that the treatment is not efficacious. Such a determination of treatment efficacy may be used to alter the treatment. For example, by classifying the patient at a high priority level for a heart transplant.

On the other hand, a CHF treatment may stabilize the BIN expression level resulting in a normal or near normal expression level. As described in the examples below, as a failing heart recovers, the BIN1 expression level increases. A normal BIN1 expression, and/or a normal IDF value, indicates a decreased likelihood of a cardiac failure and that the treatment is efficacious. This information may be used to classify the patient at a low priority level for receiving a heart transplant, and can indicate other therapies such as an intraortic balloon pump, ventricular assist device, intravenous heart therapy.

A normalized BIN1 expression or IDF value may be used to determine therapy options. For example, a normalized BIN1 expression level less than about 0.65 may be positively correlated to a risk of a poor outcome. A normalized BIN1 expression level of less than about 0.65 may be positively correlated to a poor outcome for the patient in the near future, for example, in the next 1 day-24 months, e.g., 1 day-7 days, or 1 week-2 weeks, 2 weeks-4 weeks, 1 month-3 months, 3 month-6 months, 6 months-8 months, 8 months-12 months, 12 months-18 months, 18 months-24 months. The poor outcome may be death, LVAD implant, or no improvement in LVEF or even a further deterioration of LVEF. This information may be used to classify the patient at a high priority level for receiving a heart transplant, and can indicate other therapies such as an intraortic balloon pump, ventricular assist device, intravenous heart therapy.

On the other hand, a normalized BIN1 expression level greater than or equal to 0.65 may be negatively correlated to a risk of cardiac mortality. A normalized BIN1 expression level greater than or equal to 0.65 may be positively correlated to absence of poor outcome for the patient in the near future, for example, in the next 1 day-24 months, e.g., 1 day-7 days, or 1 week-2 weeks, 2 weeks-4 weeks, 1 month-3 months, 3 month-6 months, 6 months-8 months, 8 months-12 months, 12 months-18 months, 18 months-24 months. This information may be used to classify the patient at a low priority level for receiving a heart transplant and other therapies such as an intraortic balloon pump, ventricular assist device, intravenous heart therapy, and can indicate that a drug based therapy may stabilize the heart function of the patient.

Patients

In general, patients amenable to methods described herein are human patient diagnosed with CHF.

A CHF patient may be a patient diagnosed with end-stage CHF, or acute fulminant myocarditis, or chronic progressive non-ischemic cardiomyopathy, or chronic progressive ischemic cardiomyopathy, or a CHF patient undergoing treatment for CHF, such as, a heart transplant (i.e., post heart-transplant patient), or a patient with refractory CHF, etc.

Kits

The materials for use in the methods of the present disclosure are suited for preparation of kits produced in accordance with well known procedures. The present disclosure thus provides kits comprising agents, which may include gene-specific or gene-selective probes and/or primers, for quantitating the expression of BIN1 for predicting clinical outcome, determining treatment options or predicting response to treatment, etc. Such kits may optionally contain reagents for the extraction of RNA from heart tissue samples and/or reagents for RNA amplification. In addition, the kits may optionally comprise the reagent(s) with an identifying description or label or instructions relating to their use in the methods of the present disclosure. The kits may comprise containers (including microtiter plates suitable for use in an automated implementation of the method), each with one or more of the various reagents (typically in concentrated form) utilized in the methods, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present disclosure. Mathematical algorithms used to estimate or quantify prognostic and/or predictive information are also properly potential components of kits.

The methods provided by the present disclosure may also be automated in whole or in part.

Reports

The methods of the present disclosure are suited for the preparation of reports summarizing the results of assaying the expression level of BIN1. In certain embodiments, a report may include a determination of the risk of cardiac mortality in a CHF patient. A "report," as described herein, is an electronic or tangible document which includes report elements that provide information of interest relating to BIN1 expression level and/or a risk of cardiac mortality. A subject report can be completely or partially electronically generated, e.g., presented on an electronic display (e.g., computer monitor). A report can further include one or more of: 1) information regarding the testing facility; 2) service provider information; 3) patient data; 4) sample data; 5) an interpretive report, which can include various information including: a) indication; b) test data, where test data can include a normalized level of one or more genes of interest, and 6) other features.

The present disclosure thus provides for methods of creating reports and the reports resulting therefrom. The report may include a summary of the expression levels of the RNA transcripts, or the expression products of such RNA transcripts, for certain genes, such as BIN1, in the cells obtained from the patient's heart tissue. The report may include an assessment of risk of cardiac mortality. The report may include a recommendation for treatment modality such as surgery alone or surgery in combination with therapy. The report may be presented in electronic format or on paper. The methods disclosed herein can further include a step of generating or outputting a report, which report can be provided in the form of an electronic medium (e.g., an electronic display on a computer monitor), or in the form of a tangible medium (e.g., a report printed on paper or other tangible medium).

For clarity, it should be noted that the term "user," which is used interchangeably with "client," is meant to refer to a person or entity to whom a report is transmitted, and may be the same person or entity who does one or more of the following: a) collects a sample; b) processes a sample; c) provides a sample or a processed sample; and d) generates data (e.g., level of a response indicator gene product(s); level of a reference gene product(s); normalized level of a response indicator gene product(s)) for use in the risk of cardiac mortality assessment. In some cases, the person(s) or entity(ies) who provides sample collection and/or sample processing and/or data generation, and the person who receives the results and/or report may be different persons, but are both referred to as "users" or "clients" herein to avoid confusion. In certain embodiments, e.g., where the methods are completely executed on a single computer, the user or client provides for data input and review of data output. A "user" can be a health professional (e.g., a clinician, a laboratory technician, a physician (e.g., an cardiologist, surgeon, primary care physician), etc.).

In embodiments where the user only executes a portion of the method, the individual who, after computerized data processing according to the methods of the invention, reviews data output (e.g., results prior to release to provide a complete report, a complete report, or reviews an "incomplete" report and provides for manual intervention and completion of an interpretive report) is referred to herein as a "reviewer." The reviewer may be located at a location remote to the user (e.g., at a service provided separate from a healthcare facility where a user may be located).

Where government regulations or other restrictions apply (e.g., requirements by health, malpractice, or liability insurance), all results, whether generated wholly or partially electronically, are subjected to a quality control routine prior to release to the user.

Computer-Based Systems and Methods

The methods and systems described herein can be implemented in numerous ways. In one embodiment of particular interest, the methods involve use of a communications infrastructure, for example the internet. Several embodiments of the invention are discussed below. It is also to be understood that the present invention may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site associated (e.g., at a service provider's facility). In some embodiments, the step of using the BIN1 expression level to determine the risk of cardiac mortality in a CHF patient is performed by a computer programmed to execute an algorithm for calculating the risk. In other examples, the subject method includes causing a computer to execute an algorithm for calculating the risk of cardiac mortality in a CHF patient based on the expression level of BIN1.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which can include test data (e.g., level of a response indicator gene product(s); level of a reference gene product(s); normalized level of a response indicator gene product(s)); and may also include other data such as patient data. This information received can be stored at least temporarily in a database, and data analyzed to generate a report as described above.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the final report) are maintained on a web server for access, preferably confidential access, with typical browsers. The data may be accessed or sent to health professionals as desired. The input and output data, including all or a portion of the final report, can be used to populate a patient's medical record which may exist in a confidential database at the healthcare facility.

A system for use in the methods described herein generally includes at least one computer processor (e.g., where the method is carried out in its entirety at a single site) or at least two networked computer processors (e.g., where data is to be input by a user (also referred to herein as a "client") and transmitted to a remote site to a second computer processor for analysis, where the first and second computer processors are connected by a network, e.g., via an intranet or internet). The system can also include a user component(s) for input; and a reviewer component(s) for review of data, generated reports, and manual intervention. Additional components of the system can include a server component(s); and a database(s) for storing data (e.g., as in a database of report elements, e.g., interpretive report elements, or a relational database (RDB) which can include data input by the user and data output. The computer processors can be processors that are typically found in personal desktop computers (e.g., IBM, Dell, Macintosh, etc.), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one example, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The input client components can be complete, stand-alone personal computers offering a full range of power and features to run applications. The client component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the client and server(s), including processing on a single machine such as a mainframe, a collection of machines, or other suitable configuration are contemplated. In general, the client and server machines work together to accomplish the processing of the present disclosure.

Where used, the database(s) is usually connected to the database server component and can be any device which will hold data. For example, the database can be a magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc., as desired.

Computer-readable Storage Media

The present disclosure also contemplates a computer-readable storage medium (e.g. CD-ROM, memory key, flash memory card, diskette, etc.) having stored thereon a program which, when executed in a computing environment, provides for implementation of algorithms to carry out all or a portion of the calculation of risk of cardiac mortality, as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data is carried out at the remote site to generate a report. After review of the report, and completion of any needed manual intervention, to provide a complete report, the complete report is then transmitted back to the user as an electronic document or printed document (e.g., fax or mailed paper report). The storage medium containing a program according to the invention can be packaged with instructions (e.g., for program installation, use, etc.) recorded on a suitable substrate or a web address where such instructions may be obtained. The computer-readable storage medium can also be provided in combination with one or more reagents for carrying out the assaying step of the subject method (e.g., primers, probes, arrays, or other such kit components).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, and temperature is in degrees Centigrade.

Materials and Methods

Plasmids, Cell Culture, and Transfection. Human BIN1 (Isotype 8) cDNA was obtained from Origene. Whole length BIN1-8(1-454aa) and BIN1-BAR*(1-282aa) were then amplified and cloned into pDONR/Zeo (Invitrogen) using Gateway BP cloning to generate entry clones. The genes were subsequently inserted into pDest-eGFP-N1, pDest-mCherry-N1 (converted vectors originally from Clontech), and pcDNA3.2-V5-Dest by Gateway LR cloning. Human CaV1.2 was obtained from Origene. Human β2b and rabbit α2δ1 were provided by Dr. Michael Sangunetti. APC-GFP was provided by Dr. Torsten Wittmann. N-terminal GFP-CaV1.2 was provided by Dr. Kurt Beam, and C-terminal CaV1.2-GFP was described previously (Takahashi et al., 2004). Dominant Negative APC (APC 1-1450aa) was provided by Dr. Ken Kaplan.

HeLa cells and mouse atrial HL-1 cells were cultured in DMEM and Claycomb medium under standard mammalian cell conditions. FuGene 6 (Roche) was used for cDNA transfections in HeLa cells. Lipofectamine (Invitrogen) with plus reagent were used for cDNA transfections in HL-1 cells.

Immunostaining and Electron Microscopy. For all immunocytochemistry, cold methanol fixation (Shaw et al., 2007) was used except for WGA labeling (4% PFA, room temperature) as previously described. For immunohistochemistry, cryosections were fixed in ice-cold acetone for 10 min. For EM tannic acid labeling, cells were fixed with 1.2% glutaraldehyde in the presence of 0.5 1 mg/ml tannic acid. For immunolabeling, mouse cardiomyocyte suspension was fixed in 2% paraformaldehyde with 0.1% glutaraldehyde for 2 hours at room temperature, then washed in 120 mM sodium phosphate buffer and pelleted. Pellets were then infiltrated in PVP sucrose, mounted, and frozen in liquid nitrogen. Immunogold labeling of cryosections was performed as described (Butler et al., 1997). Mouse anti-BIN1 antibody was obtained from Sigma. For CaV1.2, rabbit anti-CaV1.2 from Alamone was used.

Widefield Epifluorescent, TIRF and Spinning Disc Confocal Microscopy. All imaging was performed on a Nikon Eclipse Ti microscope with a 100×1.49 NA TIRF objective and NIS Elements software. Deconvolution of widefield epifluorescent images was performed using Autoquant software (Media Cybernetics). A laser merge module 5 (Spectral applied research, CA) with DPSS lasers (486, 561, 647 nm) was used as a source for TIRF and confocal (Yokogawa, CSU-X1) imaging. Multiple wavelength TIRF was achieved with Dual-View emission splitter (Optical Insights). Time lapse sequence for APC and BIN1 were acquired at a continuous rate of two frames per second with 200 ms and 400 ms exposure per frame for BIN1 and APC, respectively. High resolution Cool SNAP HQ2 camera and high sensitive Cascade II 512 camera (Photometrics) were used for image capture.

Human Tissue Collection and Cardiomyocytes Isolation. With the approval of the University of California, San Francisco (UCSF) Committee for Human Research, tissue from hearts removed at the time of transplant at UCSF, or from organ donors whose hearts were not transplanted, were obtained. Full informed consent was obtained from all UCSF transplant recipients prior to surgery. The California Transplant Donor Network (CTDN) provided the unused donor hearts and obtained informed consent for their use from the next of kin.

After immediate perfusion with cold cardioplegia, full-thickness samples from left ventricular free wall were cleaned rapidly of all epicardial fat and snap frozen into liquid nitrogen for later protein and mRNA analysis. More sections were embedded in OCT medium and frozen in liquid N2-chilled isopentane for immunohistochemistry. For cardiomyocytes isolation, ventricular free wall samples were cut into ~1 mm3 sections for digestion with pre-warmed collagenase II (2 mg/ml, Worthington) at 37° C. in calcium free KHB solution (134 mM NaCl, 11 mM Glucose, 10 mM Hepes, 4 mM KCl, 1.2 mM $MgSO_4$, 1.2 mM $Na_2HPO_4$, 10 mM BDM, 0.5 mg/ml BSA, pH 7.4) (Dipla et al., 1998) with modification of a previously reported method (Beuckelmann et al., 1991). Dissociated cardiomyocytes were allowed to attach to laminin-precoated glass coverslips before fixation for immunocytochemistry.

Isolation and Culture of Adult Mouse Cardiomyocytes. Mouse ventricular myocytes were isolated from male adult C57/Black mouse (8-12 weeks; Charles River) after dissociation with collagenase II (Worthington, Lakewood, N.J.) with previously described method (O'Connell et al., 2007). For surface biotinylation experiments, cardiomyocytes were attached to laminin-precoated culture dishes and cultured in primary cardiomyocyte medium (ScienCell) in 37° C. and 5% $CO_2$ incubator overnight in the presence of 20 μM Dynasore with or without 30 μM Nocodazole.

Surface Biotinylation of CaV1.2. After treatment, the cells were quickly washed and incubated with ice-cold 1 mg/ml EZ-link™ Sulfo-NHS-SS-Biotin (Pierce) for 25 min. After 2×5 min quenching of unbound biotin with 100 µM glycine, cells were washed and lysed in RIPA buffer (50 mM Tris pH 7.4, 150 mM NaCl, 1 mM EDTA, 1% Triton X-100, 1% sodium deoxycholate, 2 mM NaF, 200 µM $Na_3VO_4$) supplemented with Complete Mini protease inhibitor cocktail (Roche). Total protein concentrations were determined and normalized between samples. The lysates were then incubated with prewashed NeutrAvidin coated beads at 4° C. overnight. After washes, bound surface proteins were eluted and denatured, separated on NuPage gels (Invitrogen), and probed with rabbit anti-CaV1.2 antibody (Alomone).

Communoprecipitation. Hela cells were cotransfected with human CaV1.2 along with regulatory β2b and α2δ1 subunits and BIN1-V5, harvested, lysed in 1% Triton X-100 Co-IP buffer (50 mM Tris pH 7.5, 150 mM NaCl, 2 mM EDTA, 2 mM EGTA, 1 mM DTT, 1 mM NaF, 100 µM $Na_3VO_4$, 1% Triton X-100) supplemented with Complete Mini protease inhibitor cocktail. The lysate was then incubated with either mouse anti V5 antibody (2 µg) or equal amount of non-specific mouse IgG for 2 hours before pull down with rec-protein-G-Sepharose (Invitrogen) for 1 hr. Material bound to washed beads were eluted, denatured, separated, and probed with rabbit antibodies against CaV1.2 (Alomone) or V5 (Sigma).

Quantifying Gene Expression. TaqMan primer/probe sets (5'FAM/3'BHQ; Applied Biosystems) for real-time PCR for human CaV1.2, BIN1, genes were obtained using Primer Express (Applied Biosystems). Total RNA was isolated and purified from left ventricle free wall by TRIzol (Invitrogen) extraction, followed by purification by PureLink™ RNA mini kit (Invitrogen) and treatment with Turbo DNase (Ambion). First-strand cDNA synthesis was performed using the Superscript First-Strand Synthesis System (BioRad) and oligo-dT primers. Quantitative real-time PCR reactions were performed in a 384-well format using Platinum qPCR mix (Applied Biosystems) and total reaction volumes of 10 µl on an ABI 7900HT (Applied Biosystems). Absolute gene expression was quantified using the method of Dolganov et al. using PP1A, Ubiquitin, EEFA1, PRL13A, and HRPT1 as control genes (Dolganov et al., 2001) (Butler et al., 1997). The primer probes for BIN1 and CaV1.2 were obtained from Applied Biosystems. TaqMan® Gene Expression Assays, Assay ID Hs01120898_m1 was used for quantification of BIN1 expression level. This assay detects BIN1 transcript variants 8 and 9. TaqMan® Gene Expression Assays, Assay ID Hs00167681_m1 was used for quantification of CaV1.2 expression level. The following probes were used for the housekeeping genes: RPL13A-TMP: CAGAGCGGCCTG-GCCTCGCT (SEQ ID NO: 7), Ubiquitin-TMP: TGAGCT-TGTTTGTGTCCCTGTGGGTG (SEQ ID NO: 8), EEF1A1-TMP: CACTGGCATTGCCATCCTTACGGG (SEQ ID NO: 9), and PPIA-TMP: ATGGCAAATGCTGGACCCAA-CACA (SEQ ID NO: 10).

Quantifying Cardiac Ejection Fraction. A transthoracic echocardiogram was performed on the heart which consists of using ultrasound waves from a probe placed on the chest of the patient. The ultrasound waves are used to construct one-dimensional and two-dimensional slices of the heart. Standard volume rendering software on clinical echocardiogram machines (e.g. Acuson) compute left ventricular volume from the slices. The ejection fraction is the difference in volumes during systole and diastole divided by the volume in diastole. Normal ejection fraction is approximately 55-60%.

Example 1

CaV1.2 Has an Intracellular Distribution in Failing Heart

Cardiac excitation-contraction (EC) coupling, a process essential to each heartbeat, links electrical excitation of the myocyte to its mechanical contraction. EC coupling begins with local calcium entry through CaV1.2 channels that then causes a large release of calcium by the intracellular sarcoplasmic reticulum (Fabiato, 1983). Ryanodine receptors on the sarcoplasmic reticulum (SR) are the local calcium sensors and release channels (Cheng et al., 1993; Inui et al., 1987; Pessah et al., 1985). In ventricular cardiomyocytes, close association of CaV1.2 channels and ryanodine receptors is necessary for efficient calcium-induced-calcium release (CICR) (Bers, 2002). Synchronous CICR occurs at the EC-couplons, where 10-25 L-type calcium channels and 100-200 ryanodine receptors coincide and cooperate with each other (Bers, 2001). In order to locally approximate the SR bound ryanodine receptors, CaV1.2 channels are necessarily enriched on the T-tubule invaginations of the sarcolemma (Scriven et al., 2000). Despite the clear positional necessity of CaV1.2 channels to be enriched at T-tubules, there exists little understanding of the mechanism by which CaV1.2 channels are trafficked and localized to these regions of membrane.

In failing heart, the intracellular calcium transient of ventricular cardiomyocytes has a low amplitude and slow decline (Beuckelmann et al., 1992; Gwathmey et al., 1987; Sipido et al., 1998), resulting in compromised contraction (Harding et al., 1994). Multiple factors downstream of calcium entry through CaV1.2 have been identified in failing muscle that contribute to changes in the calcium transient, including dysfunction in calcium removal (Hasenfuss, 1998; Hasenfuss et al., 1999) and more recently, phosphorylation and dysfunction of the ryandoine release channels (Lehnart et al., 2005; Marx et al., 2000). There have also been reports that dyssynchronous CICR may exist in failing cardiomyocytes and contribute to defective EC-coupling gain in failing heart (Gomez et al., 1997; Litwin et al., 2000).

Figure 1:
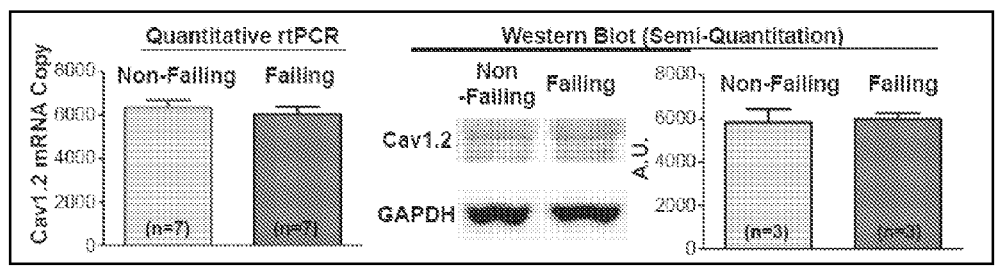
FIG. 1 depicts CaV1.2 expression in human heart. (A) Quantitative RT-PCR analysis (left) and semi-quantitative western blotting show no difference in CaV1.2 expression in both non-failing and failing human hearts. (B) Three dimensional volume view of intracellular CaV1.2 distribution reconstructed from a stack of 100× confocal image frames acquired at a z-step of 0.1 μm.
Figure 1:
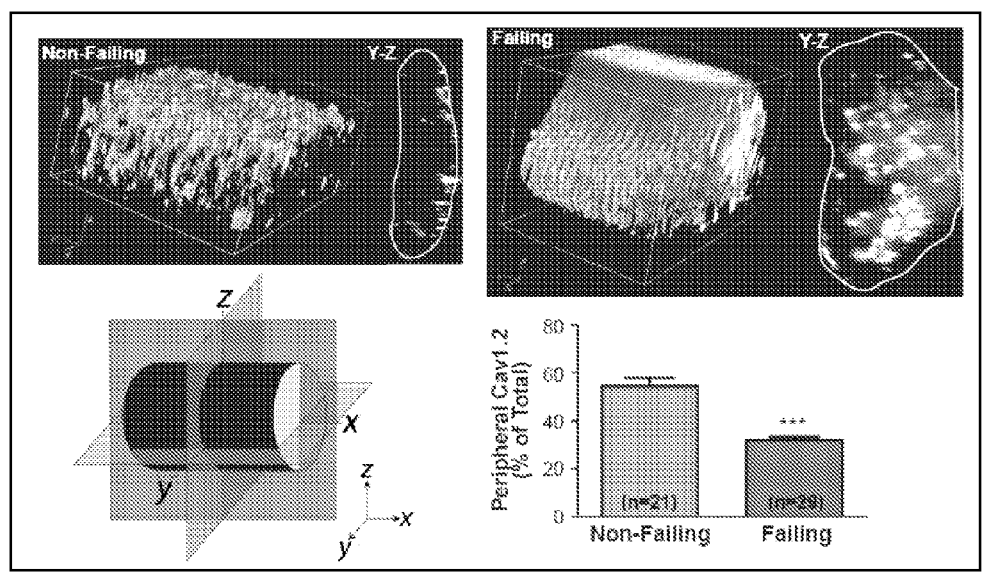

Reports of CaV1.2 channel expression in dilated cardiomyopathy muscle vary considerably from CaV1.2 being unchanged to decreased (Hullin et al., 1999; Mewes and Ravens, 1994; Schroder et al., 1998). Freshly explanted hearts from transplant recipients with end-stage non-ischemic dilated cardiomyopathy and non-failing hearts from organ donors that could not be used for transplantation were obtained. After immediate perfusion with cardioplegia, ventricular sections were frozen and ventricular cardiomyocytes were also isolated. Immunohistochemistry of cryosections shows staining of CaV1.2 and a marker for T-tubules, the T-tubule formation protein BIN1) (Lee et al., 2002). In non-failing myocardium, CaV1.2 distribution is well organized along T-tubules marked with BIN1. However, in failing myocardium, T-tubular BIN1 distribution is disrupted along with CaV1.2. Interestingly, data shown in FIG. 1A indicate that CaV1.2 expression is unchanged both at mRNA and protein levels in failing myocardium. These data indicate that the cellular distribution of CaV1.2, rather than expression level, is altered in failing myocardium.

To better understand the cellular distribution of CaV1.2, isolated human cardiomyocytes were stained and imaged at Z-depth increments of 0.1 µm with a spinning disc confocal microscope. The Z-axis cross sections of cardiomyocytes were generated from the original z-stack and shown in the side images. Fluorescent intensity at cell peripheral within 2 µm of cell edges were quantified and normalized to total cellular fluorescent intensity and presented in the bottom right panel. Peripheral fluorescent signal is significantly reduced in failing cardiomyocytes. Three dimensional volume views and Z-axis cross sections are shown in FIG. 1B. As seen in the subsection of a non-failing cardiomyocyte (left), CaV1.2 is enriched at T-tubules, whereas in diseased cardiomyocytes CaV1.2 has an intracellular distribution and the distinctive T-tubular invaginations are lost. Peripheral CaV1.2 quantification indicates that the peripheral proportion of CaV1.2 (within 2 µm from cell edges concentrated of T-Tubules) is significantly reduced in failing cardiomyocytes. CaV1.2 internalization in failing cardiomyocytes can also be seen in full 360 degree rotations. Given that CaV1.2 protein and mRNA are unchanged (FIG. 1A), internalization of L-type calcium channels in failing cardiomyocytes indicates improper post-Golgi trafficking of the channel.

Example 2

BIN1 Targets CaV1.2 to T-Tubules

Figure 2:
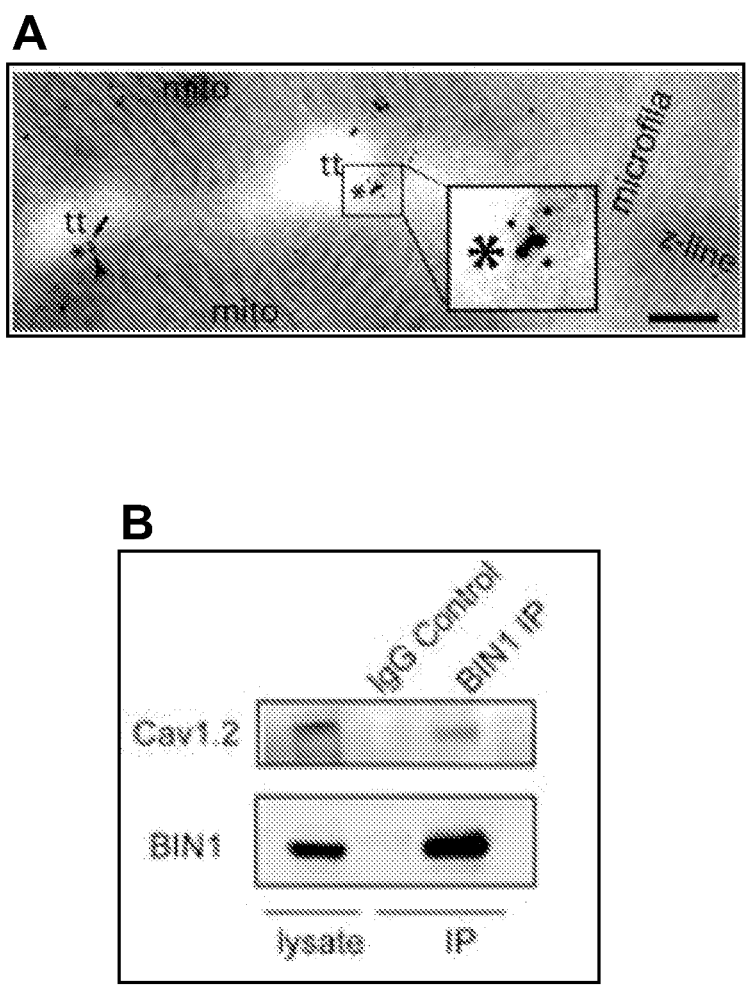
FIG. 2 shows BIN1 mediated targeting of CaV1.2 to T-Tubules. (A) Electron microscope image of a mouse cardiomyocyte fixed and immunogold labeled BIN1 (small dots at Ø 10 nm) and CaV1.2 (large dots at Ø 15 nm) (Scale bar: 200 nm). BIN1 and CaV1.2 cluster within 50 nm on T-tubule membranes close to Z-line. (B) CaV1.2 immunoprecipitates with BIN1.

The mechanism of CaV1.2 targeting to T-tubule membranes was explored. Co-staining of BIN1 and CaV1.2 in both isolated non-failing human cardiomyocytes and mouse cardiomyocytes indicates that BIN1 outlines T-tubules and CaV1.2 is enriched along such invaginations and colocalizes with BIN1. For higher resolution imaging, transmission electron microscopy with dual immunogold labeling was used to identify CaV1.2 and BIN1 on T-tubule ultrastructures in adult mouse cardiomyocytes. A representative image in FIG. 2A indicates that BIN1 (small 10 nm dots) and CaV1.2 (large 15 nm dots) are enriched and cluster within 10-50 nm of each other, occurring at T-tubular membrane structures.

Given that CaV1.2 is closely associated with the tubulogenesis protein BIN1 at T-tubules, it is possible that BIN1 specifically attracts delivery of CaV1.2 to T-tubules. This possibility was tested using the reductionist approach of studying the association between BIN1 and CaV1.2 in an atrial myocyte cell type HL-1 cells that do not have the capability of forming T-tubules but do express endogenous CaV1.2 (*), and non-myocyte Hela cells that have neither T-tubules nor CaV1.2. In both cell lines, exogenous BIN1 is able to induce nascent T-tubule-like membrane invagination. In HL-1 cells, fixed cell immunocytochemistry indicates that endogenous CaV1.2 colocalizes with exogenous BIN1. Also, BIN1 forms linear tracks which corresponds to T-tubule-like structures (Lee et al., 2002).

Similar colocalization results are obtained with non-myocyte HeLa cells transfected with exogenous BIN1 and CaV1.2. Surface expression of CaV1.2 was evaluated using total internal reflection fluorescence (TIRF) microscopy which limits the imaging depth to within 50-100 nm of the coverslip. Using CaV1.2 and BIN1 tagged with spectrally distinct fluorophores, a brief time lapse capture was performed. The results indicate that, at the membrane surface, BIN1 induced structures attract surface CaV1.2 thereby causing local enrichment of calcium channel. The HeLa cell data are intriguing, indicating that in the absence of other myocyte structures as well as the absence of endogenous CaV1.2, membrane anchoring protein BIN1 and CaV1.2 will still congregate when overexpressed. Close biochemical association between BIN1 and CaV1.2 in Hela cells is further supported by positive co-immunoprecipitation of V5 tagged BIN1 and probed for CaV1.2. (FIG. 2B).

Example 3

CaV1.2 is Targeted to BIN1, not T-Tubules

Figure 3:
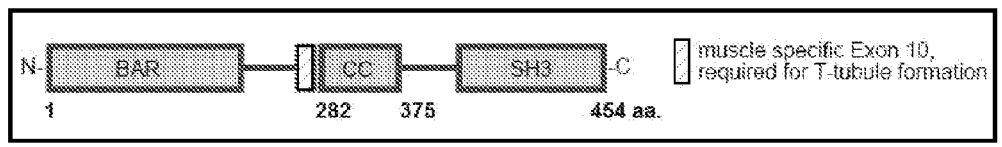
FIG. 3 shows CaV1.2 targeting requires BIN1 not T-tubule structure. (A) Domain map of wild-type BIN1 (BIN1-WT) shows a N-terminal BAR domain followed by 15 amino acids encoded by exon 10, the coiled-coil region and the C-terminal SH3 domain. (B) Surface biotinylation of CaV1.2 in HL-1 cells transfected with either BIN1-WT or a BIN1 truncation (BIN1-BAR* which retains the T-tubule forming domain but lacks CaV1.2 binding domain) shows that whole length BIN1 is required to induce surface expression of CaV1.2.
Figure 3:
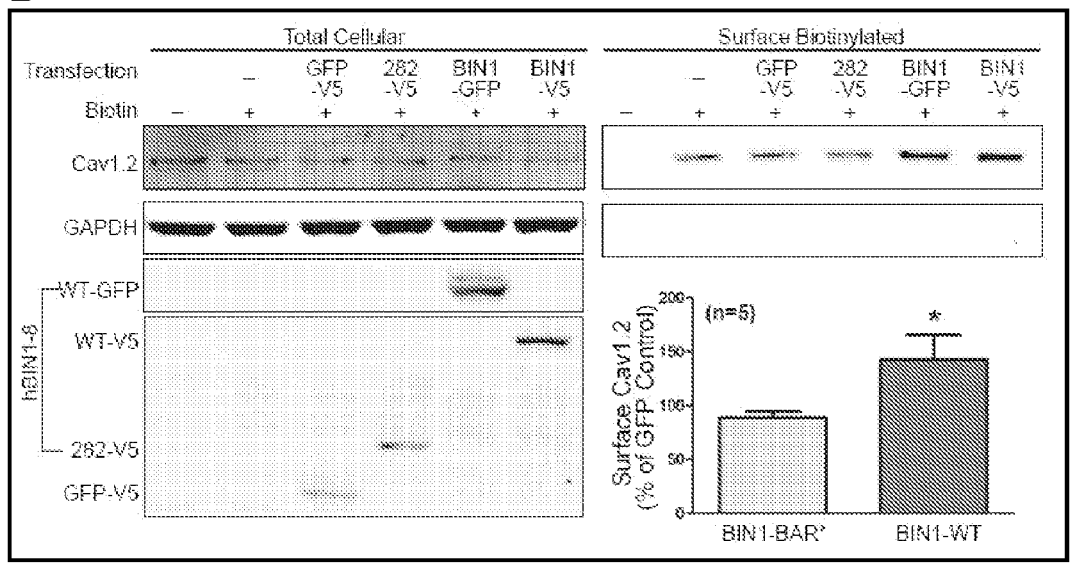

It was determined whether it is BIN1 protein or T-tubule structures that is sufficient for CaV1.2 targeting. Wild-type BIN1 (BIN1-WT, 1-454aa) has an N-terminal BAR domain followed by 15 amino acids (aa) encoded by exon 10 which is required for phospholipid binding and T-tubule formation, a coil-coiled linkage domain, and a C-terminal SH3 domain for protein-protein interaction (FIG. 3A) (Lee et al., 2002; Nicot et al., 2007). A previously published C-terminal truncated BIN1-BAR* (1-282aa, BAR+Exon10), which retains the ability to induce membrane invagination was created (Lee et al., 2002). BIN1-BAR* cannot attract endogenous CaV1.2 to the nascent T-tubule structures such as those in HL-1 cells. In an HL-1 cell transfected with BIN1-WT, endogenous CaV1.2 is distributed along BIN1 structures. In contrast, in cells transfected with BIN1-BAR*, CaV1.2 shows poor colocalization with the BIN1 structures. The effect of BIN1-WT and BIN1-BAR* on CaV1.2 surface targeting was further tested by a biochemical surface biotinylation assay. As the data in FIG. 3B indicate, unlike BIN1-BAR*, BIN1-WT induces surface expression of CaV1.2. The assay indicates that T-tubule targeting of CaV1.2 requires full length BIN1; T-tubule structures induced by BIN1-BAR* are not sufficient to attract CaV1.2.

Example 4

Failing Cardiomyocytes Express Less BIN1 and Have Shallow T-Tubules

Figure 4:
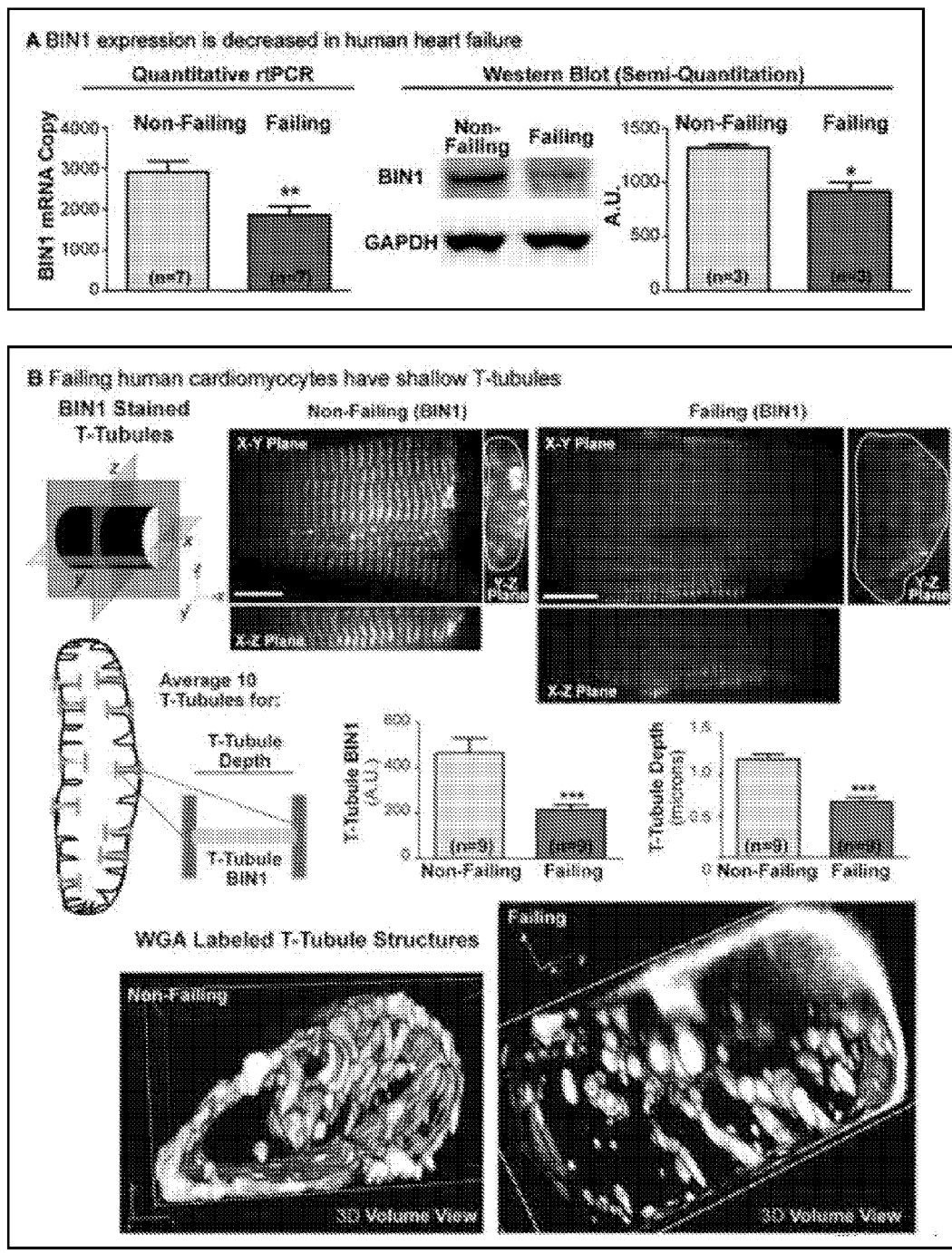
FIG. 4 depicts expression levels of BIN1 in heart and T-tubule morphology. (A) Quantitative rt-PCR analysis (left) and semi-quantitative western blotting show significant reduction of BIN1 expression in failing human hearts. (B)

Since BIN1 generates T-tubules and targets CaV1.2 to T-tubules (FIG. 3), it was determined whether the internalization of CaV1.2 (FIG. 1) in failing cardiomyocytes is the result of abnormal BIN1 expression. BIN1 mRNA and protein expression was measured in failing human hearts by quantitative RT-PCR and western blot, respectively. Compared to non-failing heart tissue, failing myocardium has a significantly lower message and protein level of BIN1 (FIG. 4A). Isolated human cardiomyocytes were also used to evaluate BIN1 expression at the cellular level. Tubular BIN1 expression and the T-tubule depth indicated by BIN1 staining in the cross sections were quantified and summarized (FIG. 4B). As indicated in the cross-section, human failing cardiomyocytes have much lower BIN1 expression along T-tubules. Quantification of BIN1 signal in T-tubules indicates that failing cardiomyocytes have less BIN1 signal and shallower T-tubules. Three dimensional reconstruction of membrane labeling with wheat germ agglutinin (WGA) confirms disruption of the T-tubule network in failing cardiomyocytes. Cross-sections indicate that failing cardiomyocytes have shallower and diminished T-tubules (FIG. 4B, bottom row). In summary, data from FIGS. 1-4 indicates that BIN1 induces T-tubule formation and targets CaV1.2 to T-tubule membranes; in failing cardiomyocytes, BIN1 is decreased, resulting in shallow T-tubules and reduced membrane associated CaV1.2.

Example 5

CaV1.2 Targeting Involves APC-Tipped Microtubules

To evaluate the role of microtubules in trafficking of CaV1.2, endogenous L-type calcium channels (CaV1.2)

were co-stained with α-tubulin in fixed atrial HL-1 cells and examined with high resolution imaging (with deconvolution post-processing). Results indicate that CaV1.2 is concentrated in the perinuclear Golgi and distributes along the microtubule network. To confirm that the CaV1.2 channels associated with microtubules are being trafficked to the membrane (i.e. forward trafficking), live HL-1 cells and adult cardiomyocytes were exposed to the microtubule disrupter nocodazole in the presence Dynasore, which is a dynamin GTPase inhibitor that blocks endocytosis (Macia et al., 2006). Expression of surface CaV1.2 was assayed by surface biotinylation. Results from the adult cardiomyocytes in FIG. 5 indicate that microtubule disruption results in less forward trafficking of CaV1.2 to the membrane. Similar results were obtained for surface expression of endogenous CaV1.2 in HL-1 cells.

Next, it was evaluated if a +TIP protein was associated with CaV1.2 delivery to BIN1 at T-tubules. EB1 distribution in cardiomyocytes was found to be concentrated at the intercalated disc rather than T-tubules. Whereas EB1 is typically associated with cell-cell border regions (Shaw et al., 2007), the +TIP protein APC has a different cellular distribution (Barth et al., 2002) and is more commonly associated with extending membrane of migrating cells (Etienne-Manneville and Hall, 2003; Neufeld and White, 1997). More importantly, APC is involved in epithelia tubulogenesis (Pollack et al., 1997). Therefore, the distribution of APC in cardiomyocytes was explored. Triple staining of α-tubulin, APC, and CaV1.2 in mouse cardiomyocytes revealed that APC resides in the regions of T-tubules and Z-lines, and that APC tipped microtubules frequently cluster in regions of CaV1.2 enrichment. To test whether APC-tipped microtubules are involved in delivery of endogenous CaV1.2, a dominant negative form of APC (Green et al., 2005) was used in atrial HL-1 cells. Surface biotinylation indicated that interfering with APC function reduces surface expression of CaV1.2 (FIG. 6A). Thus, APC has a role in delivering CaV1.2 channels to the sarcolemma.

Given that EB1-tipped microtubules can be anchored to adherens junctions structures (Ligon and Holzbaur, 2007), facilitating the delivery of ion channels (Shaw et al., 2007), live cell imaging was used to evaluate whether APC tipped microtubules could be anchored by BIN1. HeLa cells were transfected with BIN1-mCherry and APC-GFP and imaged for 120 seconds with both mCherry and GFP signals captured alternatively at an average frame rate of 2.5 seconds. APC-tipped microtubules typically concentrate at the leading edge regions of the cell. Manual traces of the path of six individual APC-tipped microtubules during the imaging interval were obtained. When APC is in the vicinity of BIN1, APC-tipped microtubules linger around the BIN1 structure. In contrast, at cell edges absent of BIN1 structures, APC-tipped microtubules travel a longer distance at a faster velocity, without being anchored. The full data of APC particle path length and velocity (FIG. 6B) indicate that APC anchors microtubules to BIN1 facilitating delivery of CaV1.2 to BIN1 containing membrane.

Example 6

BIN1 Expression Level in Heart on LVAD

Heart from an end stage dilated cardiomyopathy patients who had received a left ventricular assist device (LVAD) at LV Apex was analyzed to determine BIN1 expression level. BIN1 expression level was determined in heart muscle from the LV-FW and the LV-APEX of the patient. This patient had been on the LVAD for about six months. BIN1 expression level was also determined in corresponding tissue from individuals who died for reasons other than heart disease. The BIN 1 expression levels are shown in FIG. 7. FIG. 7 shows that non-failing heart from individuals who died for reasons other than heart disease exhibit comparable BIN1 expression levels in left ventricle free wall (LVFW) and LV Apex (A), while hearts from end stage dilated cardiomyopathy patients who received LVAD at LV Apex show a recovery of BIN1 expression in the LV apex heart tissue (compare to LV-FW) (B).

Example 7

$IDF_{CaV1.2}$ and/or $IDF_{HK}$ Values and Heart Health $IDF_{CaV}$ is a ratio of CaV1.2 mRNA expression level to BIN1 mRNA expression level. $IDF_{HK}$ is a ratio of HPRT1 (or another housekeeping gene) expression level to BIN1 mRNA expression level. $IDF_{CaV}$ and $IDF_{HK}$ values were determined for failing and non-failing heart. Results of the analysis of the $IDF_{CaV}$ values is shown in FIG. 8. FIG. 8 shows that cardiac $IDF_{CaV}$ is significantly higher in hearts with end-stage dilated cardiomyopathy. FIG. 8 (A) shows $IDF_{CaV}$ for non-failing heart from individuals who died for reasons other than heart disease (filled circles) and for failing hearts from end stage dilated cardiomyopathy patients (filled squares). FIG. 8 (B) shows that cardiac $IDF_{CaV}$ correlates with left ventricular ejection fraction (LVEF). $IDF_{CaV}$ for non-failing heart from normal control individuals who died for reasons other than heart disease (filled squares) and for failing hearts from end-stage dilated cardiomyopathy patients (filled circles) are depicted.

Results of the analysis of the $IDF_{HK}$ values (measured as a ratio of a HPRT1 mRNA to BIN1 mRNA) is shown in FIG. 9. FIG. 9 shows that cardiac $IDF_{HK}$ is significantly higher in hearts with end-stage dilated cardiomyopathy. FIG. 9 (A) shows $IDF_{HK}$ values for non-failing heart from normal control individuals who died for reasons other than heart disease (filled circles) and for failing hearts from end-stage dilated cardiomyopathy patients (filled squares). FIG. 9 (B) shows that cardiac $IDF_{HK}$ correlated to left ventricular ejection fraction (LVEF). $IDF_{HK}$ for non-failing heart from normal control individuals who died for reasons other than heart disease (filled squares) and for failing hearts from end-stage dilated cardiomyopathy patients (filled circles) are depicted.

Example 8

BIN1 Expression Correlates to Cardiac Output in Heart Failure Patients

Endomyocardial biopsies were obtained from the right ventricular septum from fourteen patients with heart failure of unknown etiology during clinical evaluation. These patients exhibited idiopathic non-infiltrative cardiomyopathy and reduced cardiac output (lower than 4.5 L/min). The heart biopsies were analyzed by quantitative immunohistochemistry for BIN1 and, for sample normalization, Cav1.2 content. For each biopsy sample, individual cardiomyocyte cross sections were outlined for measurement of cellular levels of BIN1 and Cav1.2 (at least ten cardiomyocytes per sample). As seen in FIG. 10, there is a strong correlation between normalized BIN1 levels and cardiac output.

Example 9

BIN1 Expression Predicts Outcome in Heart Failure Patients

The fourteen patients, from whom endomyocardial biopsies were obtained and normalized BIN1 levels determined (see Example 8 above), were followed-up after 6-18 months to ascertain whether the normalized BIN1 levels were predictive of outcome.

Death, LVAD implant, or LVEF less than 25% was considered as a poor outcome. The results are presented in Table 1 below:

TABLE 1

| ID | BIN1/Cav1.2 | Bad Outcome? | Note |
|----|-------------|--------------|------|
| 51 | 0.49 | yes (LVEF 10%) | |
| 53 | 0.59 | yes (LVEF 20%) | |
| 87 | 0.60 | yes (LVAD)) | |
| 68 | 0.61 | no | Test Cutoff |
| 77 | 0.64 | yes (died) | (Bin1/Ca <0.65) |
| 91 | 0.66 | no | |
| 61 | 0.68 | no | |
| 52 | 0.75 | no | |
| 76 | 0.84 | yes (LVEF 20%) | |
| 80 | 0.85 | no | |
| 55 | 0.86 | no | |
| 86 | 0.89 | no | |
| 75 | 0.93 | yes (LVAD) | Giant Cell Myocarditis |
| 73 | 1.12 | no | |

Low normalized BIN1 expression level positively correlated with a Poor outcome (Table 1). Table 1 shows that patients with low BIN1 expression levels generally did not respond to therapy and had a poor outcome, i.e., death, no improvement in LVEF, or needed a LVAD implant. On the other hand, patients with high BIN1 expression levels generally did not show a Poor outcome.

Based on the follow-up data, a normalized BIN1 value of less than 0.65 was determined to be the cut-off value. Normalized BIN1 expression level less than 0.65 indicated a positive test for poor outcome and normalized BIN1 expression level equal to or more than 0.65 indicated a negative test for poor outcome.

Using the 2×2 box in Table 2, sensitivity is obtained by dividing true test positives (4) by the sum of true positives and false negatives (4+2=6). Specificity is obtained by dividing true test negatives (7) by the sum of true negative and false positive (7+1=8). Positive predictive value is obtained by dividing true test positives (4) by the sum of true positive and false positive (4+1=5). Negative predictive value is obtained by dividing true test negatives (7) by the sum of true negative and false negative (7+2=9).

TABLE 2

| Test | Gold Standard + | Gold Standard − | | |
|------|---|---|---|---|
| + | 4 | 1 | PPV | 80% |
| − | 2 | 7 | NPV | 78% |
| | SENSITIVITY 67% | SPECIFICITY 88% | | |

As seen in Table 2, a positive test is 67% predictive (normalized BIN1 level <0.65) of a poor outcome as provided above. A negative test (normalized BIN1 level ≥0.65) has a specificity of 88% (a negative test translates to an 88% chance that heart will not have a poor outcome in the at least next 6-18 months). The positive predictive value (PPV) of BIN1 expression level for a poor outcome was 80% and the negative predictive value (NPV) of BIN1 expression level for absence of poor outcome was 78%.

Example 10

Assessing the Health of Heart on Mechanical Assist Device

A patient with end-stage dilated cardiomyopathy has a LVAD implanted to aid with heart pump function. It is clinically difficult to determine whether his heart is recovering from therapy and the LVAD can be safely removed, or whether the heart continues to deteriorate. The patient, who may be either an inpatient on the cardiac service or an outpatient under the care of a cardiac team, is scheduled for a ventricular biopsy in the cardiac catheterization laboratory. After a six hour fast the patient is brought to the catheterization laboratory and provided with mild conscious sedation as well as local anesthetic (lidocaine) to an access point of either in the internal jugular vein (neck) or femoral vein (groin). A cardiac biotome is introduced and advanced to the right ventricle under fluoroscopic guidance. The biotome is used to obtain a single biopsy of the right ventricle which is immediately flash frozen in liquid nitrogen. After 2-4 hours of monitoring, the patient is either returned to his room or discharged home from the catheterization lab. Alternatively, the cardiac biotome can be advanced to the left ventricle and then used to obtain a biopsy of the left ventricle.

The tissue sample is either stored at −80 degree Celsius freezer or immediately processed. Tissue is processed using standard laboratory techniques for RNA extraction and gene expression is determined by quantitative RTPCR (qRTPCR). Expression levels of cardiac BIN1 and/or BIN1 and cardiac CaV1.2, and/or BIN1 and HPRT1 is measured using qRT-PCR.

An increased expression of cardiac BIN1 in LV-Apex compared to the LV-FW indicates that the patient is responding to LVAD treatment. Once subsequent determination of BIN1 expression levels indicate that the BIN1 expression level has stabilized, the patient is diagnosed as treated and the LVAD is removed.

As an additional indicator of heart health, the Intrinsic Disease Factor (IDF) is also determined and is used for clinical decision making. $IDF_{CaV}$ is a ratio of CaV mRNA expression level to BIN1 mRNA expression level. $IDF_{HK}$ is a ratio of HPRT1 (or another housekeeping gene) expression level to BIN1 mRNA expression level. A severely elevated IDF (for instance $IDF_{CaV}$ of greater than 30 (FIG. 7) or $IDF_{HK}$ of great than 15 (FIG. 8) or, any similar normalized IDF greater than 1.5 times control IDF) indicates that the heart has severe heart failure. A patient with a severely elevated IDF is diagnosed as requiring long-term LVAD therapy. In subsequent determination of IDF, absence an improvement from LVAD therapy as determined by a high IDF, a heart-transplant is advised. In contrast, a patient with normal or mildly elevated IDF (normalized IDF less than 1.5 times control IDF). will indicate potential recovery of heart function and, ultimately, successful removal of the LVAD.

BIN1 expression is measured in biopsies of heart tissue at regular intervals, of about one month, to establish a trend to assess the rate of cardiac recovery (or deterioration).

Thus, BIN1 expression levels and/or IDF can distinguish between hearts that can recover by LVAD therapy and hearts that cannot.

Example 11

Analysis of BIN1 Expression Levels in End Stage CHF Patients

Prognostication using currently available methods is extremely difficult for patients with end-stage congestive heart failure. Because BIN1 expression level as well as IDF quantifies the extent of disease related changes in individual cardiomyocytes, they provide prognostic data on subsets of severe heart failure patients. Specific subsets include acute fulminant myocarditis, chronic progressive non-ischemic cardiomyopathy, chronic progressive ischemic cardiomyopathy, and post heart-transplant patients.

Endomyocardial tissue biopsies from these four subsets of patients are obtained to conduct retrospective studies. For each patient, data on cardiac diagnosis, left ventricular ejection fraction, age, sex, and cardiac outcome, such as, survival time post biopsy is obtained. Heart tissue from patients about whom the clinical data are incomplete is not included in the study.

Tissue obtained by biopsy is flash frozen in liquid nitrogen and qRTPCR is performed as described above. Archived heart tissue preserved as formalin-fixed paraffin-embedded (FFPE) sample is either analyzed by qRTPCR or by immunohistochemistry. For immunohistochemistry primary antibodies against BIN1 and/or BIN1 and CaV1.2 and/or BIN1 and a housekeeping protein are used. A reduction in gene expression corresponds to reduction in fluorescence obtained with immunohistochemistry. An IDF is also obtained with quantitative immunohistochemistry of protein levels in a manner similar to the ratios obtained with the qRTPCR data, as described above.

For each of the four datasets as well as combinations of the datasets, a survival curve, such as a Kaplan-Meyer curve is derived. Survival in the patient groups is tracked and is compared to the BIN1 expression level or IDF at the time of biopsy. Patients with elevated IDF (e.g. initial value greater than 1.5 of controls without cardiac disease) have lower expected survival than patients with IDF of less than 1.5 of controls without cardiac disease.

Example 12

Using BIN1 Expression Levels in Diagnosing Heart Health

Patients with acute fulminant myocarditis have a strong indication for endomyocardial biopsy (to rule out giant cell myocarditis and eosinophilic myocarditis). Similarly, patients with end stage ischemic and non-ischemic cardiomyopathy also frequently undergo biopsy as part of the transplantation work-up. Patients who receive a ventricular assist device such as a LVAD, a right ventricular assist device (RVAD), or a biventricular assist device (BiVAD), generate a large biopsy from the ventricular core removed to insert the device. Furthermore, biopsy is frequently obtained from patients post heart transplant as either an annual screen for pre-clinical rejection or during acute decompensation periods to rule out acute rejection.

The Intrinsic Disease Factor (IDF) is obtained from the ratio of an internal control to BIN1, both assayed by qRTPCR. Internal controls are a standard set of housekeeping genes (HK), such as HPRT1 or CaV1.2. HK genes and CaV1.2 gene expression levels are not affected in heart failure.

BIN1 expression levels and/or BIN1 derived IDF is a clinical snapshot of myocardial health. Severely high IDF (estimated at greater than 1.5 of control IDF) indicates poor myocardial health with prognostic implications of low recovery. As discussed in Example 9 above, IDF prognosticates mortality based on the initial value (IDF greater than 1.5 of control IDF corresponds to high mortality). Institution of therapy such a cardiovascular drugs and mechanical assist devices can be followed by weekly or monthly biopsies to track progression of recovery. IDF is also useful in post-transplant patients requiring screening for rejection. Current biopsy examination has relatively poor sensitive and specificity because the biopsy samples is studied for signs of inflammation and immune cells which can both be present in a healthy heart and absent in a particular sample of a heart undergoing rejection. By assaying the cell biological processes of the cardiomyocytes themselves, BIN expression level and BIN1 derived IDF improve both sensitive and specificity of detection of transplant rejection.

REFERENCES

Barth, A. I., Siemers, K. A., and Nelson, W. J. (2002). Dissecting interactions between EB1, microtubules and APC in cortical clusters at the plasma membrane. Journal of cell science 115, 1583-1590.

Bers, D. M. (2001). Ecitation-contraction coupling and cardiac contractile force. (Dordrecht, Nethelands, Kluwer Academic).

Bers, D. M. (2002). Cardiac excitation-contraction coupling. Nature 415, 198-205.

Beuckelmann, D. J., Nabauer, M., and Erdmann, E. (1991). Characteristics of calcium-current in isolated human ventricular myocytes from patients with terminal heart failure. Journal of molecular and cellular cardiology 23, 929-937.

Beuckelmann, D. J., Nabauer, M., and Erdmann, E. (1992). Intracellular calcium handling in isolated ventricular myocytes from patients with terminal heart failure. Circulation 85, 1046-1055.

Birks, E. J., Tansley, P. D., Hardy, J., George, R. S., Bowles, C. T., Burke, M., Banner, N. R., Khaghani, A., and Yacoub, M. H. (2006). Left ventricular assist device and drug therapy for the reversal of heart failure. The New England journal of medicine 355, 1873-1884.

Butler, M. H., David, C., Ochoa, G. C., Freyberg, Z., Daniell, L., Grabs, D., Cremona, O., and De Camilli, P. (1997). Amphiphysin II (SH3P9; BIN1), a member of the amphiphysin/Rvs family, is concentrated in the cortical cytomatrix of axon initial segments and nodes of ranvier in brain and around T tubules in skeletal muscle. The Journal of cell biology 137, 1355-1367.

Chen, X., Piacentino, V., 3rd, Furukawa, S., Goldman, B., Margulies, K. B., and Houser, S. R. (2002). L-type Ca2+ channel density and regulation are altered in failing human ventricular myocytes and recover after support with mechanical assist devices. Circ Res 91, 517-524.

Cheng, H., Lederer, W. J., and Cannell, M. B. (1993). Calcium sparks: elementary events underlying excitation-contraction coupling in heart muscle. Science 262, 740-744.

Dipla, K., Mattiello, J. A., Jeevanandam, V., Houser, S. R., and Margulies, K. B. (1998). Myocyte recovery after mechanical circulatory support in humans with end-stage heart failure. Circulation 97, 2316-2322.

Dolganov, G. M., Woodruff, P. G., Novikov, A. A., Zhang, Y., Fernando, R. E., Szubin, R., and Fahy, J. V. (2001). A novel method of gene transcript profiling in airway biopsy homogenates reveals increased expression of a Na+-K+-Cl-cotransporter (NKCC1) in asthmatic subjects. Genome research 11, 1473-1483.

Etienne-Manneville, S., and Hall, A. (2003). Cdc42 regulates GSK-3beta and adenomatous polyposis coli to control cell polarity. Nature 421, 753-756.

Fabiato, A. (1983). Calcium-induced release of calcium from the cardiac sarcoplasmic reticulum. The American journal of physiology 245, $C_{1-14}$.

Gomez, A. M., Valdivia, H. H., Cheng, H., Lederer, M. R., Santana, L. F., Cannell, M. B., McCune, S. A., Altschuld, R. A., and Lederer, W. J. (1997). Defective excitation-contraction coupling in experimental cardiac hypertrophy and heart failure. Science 276, 800-806.

Green, R. A., Wollman, R., and Kaplan, K. B. (2005). APC and EB1 function together in mitosis to regulate spindle dynamics and chromosome alignment. Molecular biology of the cell 16, 4609-4622.

Gwathmey, J. K., Copelas, L., MacKinnon, R., Schoen, F. J., Feldman, M. D., Grossman, W., and Morgan, J. P. (1987). Abnormal intracellular calcium handling in myocardium from patients with end-stage heart failure. Circ Res 61, 70-76.

Harding, S. E., Davies, C. H., Wynne, D. G., and Poole-Wilson, P. A. (1994). Contractile function and response to agonists in myocytes from failing human heart. European heart journal 15 Suppl D, 35-36.

Hasenfuss, G. (1998). Alterations of calcium-regulatory proteins in heart failure. Cardiovasc Res 37, 279-289.

Hasenfuss, G., Schillinger, W., Lehnart, S. E., Preuss, M., Pieske, B., Maier, L. S., Prestle, J., Minami, K., and Just, H. (1999). Relationship between Na+-Ca2+-exchanger protein levels and diastolic function of failing human myocardium. Circulation 99, 641-648.

Hullin, R., Asmus, F., Ludwig, A., Hersel, J., and Boekstegers, P. (1999). Subunit expression of the cardiac L-type calcium channel is differentially regulated in diastolic heart failure of the cardiac allograft. Circulation 100, 155-163.

Inui, M., Saito, A., and Fleischer, S. (1987). Isolation of the ryanodine receptor from cardiac sarcoplasmic reticulum and identity with the feet structures. J Biol Chem 262, 15637-15642.

Lee, E., Marcucci, M., Daniell, L., Pypaert, M., Weisz, O. A., Ochoa, G. C., Farsad, K., Wenk, M. R., and De Camilli, P. (2002). Amphiphysin 2 (Bin1) and T-tubule biogenesis in muscle. Science 297, 1193-1196.

Lehnart, S. E., Wehrens, X. H., Reiken, S., Warrier, S., Belevych, A. E., Harvey, R. D., Richter, W., Jin, S. L., Conti, M., and Marks, A. R. (2005). Phosphodiesterase 4D deficiency in the ryanodine-receptor complex promotes heart failure and arrhythmias. Cell 123, 25-35.

Ligon, L. A., and Holzbaur, E. L. (2007). Microtubules tethered at epithelial cell junctions by dynein facilitate efficient junction assembly. Traffic (Copenhagen, Denmark) 8, 808-819.

Litwin, S. E., Zhang, D., and Bridge, J. H. (2000). Dyssynchronous Ca(2+) sparks in myocytes from infarcted hearts. Circ Res 87, 1040-1047.

Macia, E., Ehrlich, M., Massol, R., Boucrot, E., Brunner, C., and Kirchhausen, T. (2006). Dynasore, a cell-permeable inhibitor of dynamin. Developmental cell 10, 839-850.

Marx, S. O., Reiken, S., Hisamatsu, Y., Jayaraman, T., Burkhoff, D., Rosemblit, N., and Marks, A. R. (2000). PKA phosphorylation dissociates FKBP12.6 from the calcium release channel (ryanodine receptor): defective regulation in failing hearts. Cell 101, 365-376.

Mewes, T., and Ravens, U. (1994). L-type calcium currents of human myocytes from ventricle of non-failing and failing hearts and from atrium. Journal of molecular and cellular cardiology 26, 1307-1320.

Neufeld, K. L., and White, R. L. (1997). Nuclear and cytoplasmic localizations of the adenomatous polyposis coli protein. Proceedings of the National Academy of Sciences of the United States of America 94, 3034-3039.

Nicot, A. S., Toussaint, A., Tosch, V., Kretz, C., Wallgren-Petters son, C., Iwars son, E., Kingston, H., Garnier, J. M., Biancalana, V., Oldfors, A., et al. (2007). Mutations in amphiphysin 2 (BIN1) disrupt interaction with dynamin 2 and cause autosomal recessive centronuclear myopathy. Nature genetics 39, 1134-1139.

O'Connell, T. D., Rodrigo, M. C., and Simpson, P. C. (2007). Isolation and culture of adult mouse cardiac myocytes. Methods in molecular biology (Clifton, N.J. 357, 271-296.

Pessah, I. N., Waterhouse, A. L., and Casida, J. E. (1985). The calcium-ryanodine receptor complex of skeletal and cardiac muscle. Biochem Biophys Res Commun 128, 449-456.

Pollack, A. L., Barth, A. I., Altschuler, Y., Nelson, W. J., and Mostov, K. E. (1997). Dynamics of beta-catenin interactions with APC protein regulate epithelial tubulogenesis. The Journal of cell biology 137, 1651-1662.

Schroder, F., Handrock, R., Beuckelmann, D. J., Hirt, S., Hullin, R., Priebe, L., Schwinger, R. H., Weil, J., and Herzig, S. (1998). Increased availability and open probability of single L-type calcium channels from failing compared with nonfailing human ventricle. Circulation 98, 969-976.

Scriven, D. R., Dan, P., and Moore, E. D. (2000). Distribution of proteins implicated in excitation-contraction coupling in rat ventricular myocytes. Biophysical journal 79, 2682-2691.

Shaw, R. M., Fay, A. J., Puthenveedu, M. A., von Zastrow, M., Jan, Y. N., and Jan, L. Y. (2007). Microtubule plus-end-tracking proteins target gap junctions directly from the cell interior to adherens junctions. Cell 128, 547-560.

Sipido, K. R., Stankovicova, T., Flameng, W., Vanhaecke, J., and Verdonck, F. (1998). Frequency dependence of Ca2+ release from the sarcoplasmic reticulum in human ventricular myocytes from end-stage heart failure. Cardiovasc Res 37, 478-488.

Takahashi, S. X., Miriyala, J., and Colecraft, H. M. (2004). Membrane-associated guanylate kinase-like properties of beta-subunits required for modulation of voltage-dependent Ca2+ channels. Proceedings of the National Academy of Sciences of the United States of America 101, 7193-7198.

What is claimed is:

1. A method for determining a risk of a poor outcome in a human patient with congestive heart failure (CHF), the method comprising:
   quantitatively assaying a BIN1 expression level in a heart tissue sample obtained from the patient; and
   using the BIN1 expression level to determine the risk of a poor outcome in the patient, wherein a decreased BIN1 expression level relative to a reference BIN1 expression level is positively correlated to an increased risk of a poor outcome, wherein the reference BIN1 expression level is BIN1 expression level in heart of a healthy human subject.

2. The method of claim 1, wherein the patient has received a heart transplant and the heart tissue sample is from the transplanted heart.

3. The method of claim 1, wherein the heart of the patient is connected to a mechanical assist device.

4. The method of claim 1, wherein the patient is undergoing treatment for CHF.

5. The method of claim 2, wherein the patient is undergoing immunosuppression therapy.

6. The method of claim 1, wherein the assaying comprises measuring the level of BIN1 mRNA.

7. The method of claim 1, wherein the assaying comprises measuring the level of BIN1 protein.

8. The method of claim 1, comprising assaying a CaV1.2 expression level and normalizing the BIN1 expression level using the assayed CaV1.2 expression level.

9. The method of claim 1, wherein the poor outcome is cardiac mortality.

10. A method for determining a risk of a poor outcome in a human patient with congestive heart failure (CHF), the method comprising:
    quantitatively assaying a BIN1 expression level and an internal control gene expression level in a heart tissue sample obtained from the patient;
    determining an Intrinsic Disease Factor (IDF) by calculating a ratio of the internal control gene expression level to the BIN1 expression level; and
    using the IDF to determine the risk of a poor outcome in the patient, wherein an increased IDF relative to a reference IDF is positively correlated to an increased risk of a poor outcome,
    wherein the reference IDF is IDF in heart of a healthy human subject.

11. The method of claim 10, wherein the internal control gene is a housekeeping gene.

12. The method of claim 10, wherein the internal control gene is CaV1.2.

13. The method of claim 10, wherein the assaying comprises measuring the levels of BIN1 and the internal control gene mRNA.

14. The method of claim 10, wherein the patient has received a heart transplant and the heart tissue sample is from the transplanted heart.

15. The method of claim 10, wherein the heart of the patient is connected to a mechanical assist device.

16. The method of claim 10, wherein the patient is undergoing treatment for CHF.

17. The method of claim 14, wherein the patient is undergoing immunosuppression therapy.

18. The method of claim 10, wherein the poor outcome is cardiac mortality.

19. The method of claim 1, further comprising:
    identifying the patient as having an increased risk of a poor outcome when the BIN1 expression level is decreased relative to the reference BIN1 expression level; and
    administering a treatment for congestive heart failure to the patient.

20. The method of claim 19, wherein the treatment comprises placement of left ventricular assist device (LVAD) or an intraortic balloon pump, or a heart transplant.

21. The method of claim 6, wherein the measuring the level of BIN1 mRNA comprises:
    reverse transcribing BIN1 mRNA to produce BIN1 cDNA;
    amplifying the BIN1 cDNA;
    quantitatively assaying level of the amplified cDNA.

22. The method of claim 7, wherein the measuring the level of BIN1 protein comprises contacting the heart tissue sample with an antibody that specifically binds to BIN1 protein.

* * * * *

SEQUENCE LISTING

```
<160> NUMBER OF SEQ ID NOS: 10

<210> SEQ ID NO 1
<211> LENGTH: 2210
<212> TYPE: DNA
<213> ORGANISM: Homo sapiens
```

<400> SEQUENCE: 1

```
cgcgcccctc cctcctcgcg gacctggcgg tgccggcgcc cggagtggcc ctttaaaagg      60
cagcttattg tccggagggg gcgggcgggg ggcgccgacc gcggcctgag gcccggcccc     120
tcccctctcc ctccctctgt ccccgcgtcg ctcgctggct agctcgctgg ctcgctcgcc     180
cgtccggcgc acgctccgcc tccgtcagtt ggctccgctg tcgggtgcgc ggcgtggagc     240
ggcagccggt ctggacgcgc ggccggggct ggggctggg  agcgcggcgc gcaagatctc     300
cccgcgcgag agcggcccct gccaccgggc gaggcctgcg ccgcgatggc agagatgggc     360
agtaaagggg tgacggcggg aaagatcgcc agcaacgtgc agaagaagct cacccgcgcg     420
caggagaagg ttctccagaa gctggggaag gcagatgaga ccaaggatga gcagtttgag     480
cagtgcgtcc agaatttcaa caagcagctg acggagggca cccggctgca gaaggatctc     540
cggacctacc tggcctccgt caaagccatg cacgaggctt ccaagaagct gaatgagtgt     600
ctgcaggagg tgtatgagcc cgattggccc ggcaggatg  aggcaaacaa gatcgcagag     660
aacaacgacc tgctgtggat ggattaccac cagaagctgg tggaccaggc gctgctgacc     720
atggacacgt acctgggcca gttccccgac atcaagtcac gcattgccaa gcgggggcgc     780
aagctggtgg actacgacag tgcccggcac cactacgagt cccttcaaac tgccaaaaag     840
aaggatgaag ccaaaattgc caaggccgag gaggagctca tcaaagccca gaaggtgttt     900
gaggagatga atgtggatct gcaggaggag ctgccgtccc tgtggaacag ccgcgtaggt     960
ttctacgtca acacgttcca gagcatcgcg ggcctggagg aaaacttcca caggagatg    1020
agcaagctca accagaacct caatgatgtg ctggtcggcc tggagaagca cacgggagc    1080
aacaccttca cggtcaaggc ccagcccaga aagaaaagta aactgttttc gcggctgcgc    1140
agaaagaaga acagtgacaa cgcgcctgca aagggaaca agagcccttc gcctccagat    1200
ggctcccctg ccgccacccc cgagatcaga gtcaaccacg agccagagcc ggccggcggg    1260
gccacgcccg gggccaccct ccccaagtcc ccatctcagc cagcagaggc ctcggaggtg    1320
gcgggtggga cccaacctgc ggctggagcc caggagccag gggagacggc ggcaagtgaa    1380
gcagcctcca gctctcttcc tgctgtcgtg gtggagacct cccagcaac  tgtgaatggc    1440
accgtggagg gcggcagtgg ggccgggcgc ttggacctgc ccccaggttt catgttcaag    1500
gtacaggccc agcacgacta cacggccact gacacagacg agctgcagct caaggctggt    1560
gatgtggtgc tggtgatccc cttccagaac cctgaagagc aggatgaagg ctggctcatg    1620
ggcgtgaagg agagcgactg gaaccagcac aaggagctgg agaagtgccg tggcgtcttc    1680
cccgagaact tcactgagag ggtcccatga cggcggggcc caggcagcct ccgggcgtgt    1740
gaagaacacc tcctcccgaa aaatgtgtgg ttcttttttt tgttttgttt tcgttttttca    1800
tcttttgaag agcaaaggga aatcaagagg agaccccag  gcagaggggc gttctcccaa    1860
agattaggtc gttttccaaa gagccgcgtc ccggcaagtc cggcggaatt caccagtgtt    1920
cctgaagctg ctgtgtcctc tagttgagtt tctggcgccc ctgcctgtgc ccgcatgtgt    1980
gcctggccgc agggcgggc  tgggggctgc cgagccacca tgcttgcctg aagcttcggc    2040
cgcgccaccc gggcaagggt cctcttttcc tggcagctgt tgtgggtggg gcccagacac    2100
cagcctagcc tggctctgcc ccgcagacgg tctgtgtgct gtttgaaaat aaatcttagt    2160
gttcaaaaca aatgaaaaca aaaaaaaaat gataaaaact ctcaaaaaaa               2210
```

<210> SEQ ID NO 2

<211> LENGTH: 454
<212> TYPE: PRT
<213> ORGANISM: Homo sapiens

<400> SEQUENCE: 2

```
Met Ala Glu Met Gly Ser Lys Gly Val Thr Ala Gly Lys Ile Ala Ser
1               5                   10                  15

Asn Val Gln Lys Lys Leu Thr Arg Ala Gln Glu Lys Val Leu Gln Lys
            20                  25                  30

Leu Gly Lys Ala Asp Glu Thr Lys Asp Glu Gln Phe Glu Gln Cys Val
        35                  40                  45

Gln Asn Phe Asn Lys Gln Leu Thr Glu Gly Thr Arg Leu Gln Lys Asp
    50                  55                  60

Leu Arg Thr Tyr Leu Ala Ser Val Lys Ala Met His Glu Ala Ser Lys
65                  70                  75                  80

Lys Leu Asn Glu Cys Leu Gln Glu Val Tyr Glu Pro Asp Trp Pro Gly
                85                  90                  95

Arg Asp Glu Ala Asn Lys Ile Ala Glu Asn Asn Asp Leu Leu Trp Met
            100                 105                 110

Asp Tyr His Gln Lys Leu Val Asp Gln Ala Leu Leu Thr Met Asp Thr
        115                 120                 125

Tyr Leu Gly Gln Phe Pro Asp Ile Lys Ser Arg Ile Ala Lys Arg Gly
    130                 135                 140

Arg Lys Leu Val Asp Tyr Asp Ser Ala Arg His His Tyr Glu Ser Leu
145                 150                 155                 160

Gln Thr Ala Lys Lys Lys Asp Glu Ala Lys Ile Ala Lys Ala Glu Glu
                165                 170                 175

Glu Leu Ile Lys Ala Gln Lys Val Phe Glu Glu Met Asn Val Asp Leu
            180                 185                 190

Gln Glu Glu Leu Pro Ser Leu Trp Asn Ser Arg Val Gly Phe Tyr Val
        195                 200                 205

Asn Thr Phe Gln Ser Ile Ala Gly Leu Glu Glu Asn Phe His Lys Glu
    210                 215                 220

Met Ser Lys Leu Asn Gln Asn Leu Asn Asp Val Leu Val Gly Leu Glu
225                 230                 235                 240

Lys Gln His Gly Ser Asn Thr Phe Thr Val Lys Ala Gln Pro Arg Lys
                245                 250                 255

Lys Ser Lys Leu Phe Ser Arg Leu Arg Arg Lys Lys Asn Ser Asp Asn
            260                 265                 270

Ala Pro Ala Lys Gly Asn Lys Ser Pro Ser Pro Asp Gly Ser Pro
        275                 280                 285

Ala Ala Thr Pro Glu Ile Arg Val Asn His Glu Pro Glu Pro Ala Gly
    290                 295                 300

Gly Ala Thr Pro Gly Ala Thr Leu Pro Lys Ser Pro Ser Gln Pro Ala
305                 310                 315                 320

Glu Ala Ser Glu Val Ala Gly Gly Thr Gln Pro Ala Ala Gly Ala Gln
                325                 330                 335

Glu Pro Gly Glu Thr Ala Ala Ser Glu Ala Ala Ser Ser Ser Leu Pro
            340                 345                 350

Ala Val Val Val Glu Thr Phe Pro Ala Thr Val Asn Gly Thr Val Glu
        355                 360                 365

Gly Gly Ser Gly Ala Gly Arg Leu Asp Leu Pro Pro Gly Phe Met Phe
    370                 375                 380

Lys Val Gln Ala Gln His Asp Tyr Thr Ala Thr Asp Thr Asp Glu Leu
```

| | | | | |
|---|---|---|---|---|
| | 385 | 390 | 395 | 400 |

Gln Leu Lys Ala Gly Asp Val Val Leu Val Ile Pro Phe Gln Asn Pro
            405                        410                        415

Glu Glu Gln Asp Glu Gly Trp Leu Met Gly Val Lys Glu Ser Asp Trp
            420                        425                        430

Asn Gln His Lys Glu Leu Glu Lys Cys Arg Gly Val Phe Pro Glu Asn
            435                        440                        445

Phe Thr Glu Arg Val Pro
    450

<210> SEQ ID NO 3
<211> LENGTH: 2165
<212> TYPE: DNA
<213> ORGANISM: Homo sapiens

<400> SEQUENCE: 3

```
cgcgcccctc cctcctcgcg gacctggcgg tgccggcgcc cggagtggcc ctttaaaagg      60
cagcttattg tccggagggg gcgggcgggg ggcgccgacc gcggcctgag gcccggcccc     120
tccctctcc ctccctctgt ccccgcgtcg ctcgctggct agctcgctgg ctcgctcgcc     180
cgtccggcgc acgctccgcc tccgtcagtt ggctccgctg tcgggtgcgc ggcgtggagc     240
ggcagccggt ctggacgcgc ggccggggct ggggctggg agcgcggcgc gcaagatctc      300
cccgcgcgag agcggcccct gccacccggc gaggcctgcg ccgcgatggc agagatgggc     360
agtaaagggg tgacggcggg aaagatcgcc agcaacgtgc agaagaagct cacccgcgcg     420
caggagaagg ttctccagaa gctggggaag cagatgaga ccaaggatga cagtttgag      480
cagtgcgtcc agaatttcaa caagcagctg acggagggca cccggctgca aaggatctc      540
cggacctacc tggcctccgt caaagccatg cacgaggctt ccaagaagct gaatgagtgt     600
ctgcaggagg tgtatgagcc cgattggccc ggcagggatg aggcaaacaa gatcgcagag     660
aacaacgacc tgctgtggat ggattaccac cagaagctgg tggaccaggc gctgctgacc     720
atggacacgt acctgggcca gttccccgac atcaagtcac gcattgccaa gcgggggcgc     780
aagctggtgg actacgacag tgcccggcac cactacgagt cccttcaaac tgccaaaaag     840
aaggatgaag ccaaaattgc caaggccgag gaggagctca tcaaagccca aaggtgttt      900
gaggagatga atgtggatct gcaggaggag ctgccgtccc tgtggaacag ccgcgtaggt     960
ttctacgtca acacgttcca gagcatcgcg ggcctggagg aaaacttcca caggagatg     1020
agcaagctca accagaacct caatgatgtg ctggtcggcc tggagaagca cacgggagc    1080
aacaccttca cggtcaaggc ccagcccagt gacaacgcgc ctgcaaaagg gaacaagagc    1140
ccttcgcctc cagatggctc ccctgccgcc accccgaga tcagagtcaa ccacgagcca    1200
gagccggccg gcggggccac gcccggggcc acctcccca gtccccatc tcagccagca    1260
gaggcctcgg aggtggcggg tggacccaa cctgcggctg gagcccagga gccaggggag    1320
acggcggcaa gtgaagcagc ctccagctct cttcctgctg tcgtggtgga gaccttccca    1380
gcaactgtga atggcaccgt ggagggcggc agtgggccg ggcgcttgga cctgccccca    1440
ggtttcatgt tcaaggtaca ggcccagcac gactacacgg ccactgacac agacgagctg    1500
cagctcaagg ctggtgatgt ggtgctggtg atccccttcc agaaccctga agagcaggat    1560
gaaggctggc tcatgggcgt gaaggagagc gactggaacc agcacaagga gctgagaaag    1620
tgccgtggcg tcttccccga gaacttcact gagagggtcc catgacgcg ggcccaggc     1680
agcctccggg cgtgtgaaga acacctcctc ccgaaaaatg tgtggttctt ttttttgttt    1740
```

-continued

```
tgttttcgtt tttcatcttt tgaagagcaa agggaaatca agaggagacc cccaggcaga    1800
ggggcgttct cccaaagatt aggtcgtttt ccaaagagcc gcgtcccggc aagtccggcg    1860
gaattcacca gtgttcctga agctgctgtg tcctctagtt gagtttctgg cgcccctgcc    1920
tgtgcccgca tgtgtgcctg gccgcagggc ggggctgggg gctgccgagc accatgctt    1980 gcctgaagct tcggccgcgc cacccgggca agggtcctct tttcctggca gctgctgtgg    2040
gtggggccca gacaccagcc tagcctggct ctgccccgca gacggtctgt gtgctgtttg    2100
aaaataaatc ttagtgttca aaacaaaatg aaacaaaaaa aaaatgataa aaactctcaa    2160
aaaaa                                                                 2165
```

<210> SEQ ID NO 4
<211> LENGTH: 439
<212> TYPE: PRT
<213> ORGANISM: Homo sapiens

<400> SEQUENCE: 4

```
Met Ala Glu Met Gly Ser Lys Gly Val Thr Ala Gly Lys Ile Ala Ser
 1               5                  10                  15

Asn Val Gln Lys Lys Leu Thr Arg Ala Gln Glu Lys Val Leu Gln Lys
            20                  25                  30

Leu Gly Lys Ala Asp Glu Thr Lys Asp Glu Gln Phe Glu Gln Cys Val
        35                  40                  45

Gln Asn Phe Asn Lys Gln Leu Thr Glu Gly Thr Arg Leu Gln Lys Asp
    50                  55                  60

Leu Arg Thr Tyr Leu Ala Ser Val Lys Ala Met His Glu Ala Ser Lys
65                  70                  75                  80

Lys Leu Asn Glu Cys Leu Gln Glu Val Tyr Glu Pro Asp Trp Pro Gly
                85                  90                  95

Arg Asp Glu Ala Asn Lys Ile Ala Glu Asn Asn Asp Leu Leu Trp Met
            100                 105                 110

Asp Tyr His Gln Lys Leu Val Asp Gln Ala Leu Leu Thr Met Asp Thr
        115                 120                 125

Tyr Leu Gly Gln Phe Pro Asp Ile Lys Ser Arg Ile Ala Lys Arg Gly
    130                 135                 140

Arg Lys Leu Val Asp Tyr Asp Ser Ala Arg His His Tyr Glu Ser Leu
145                 150                 155                 160

Gln Thr Ala Lys Lys Lys Asp Glu Ala Lys Ile Ala Lys Ala Glu Glu
                165                 170                 175

Glu Leu Ile Lys Ala Gln Lys Val Phe Glu Met Asn Val Asp Leu
            180                 185                 190

Gln Glu Glu Leu Pro Ser Leu Trp Asn Ser Arg Val Gly Phe Tyr Val
        195                 200                 205

Asn Thr Phe Gln Ser Ile Ala Gly Leu Glu Glu Asn Phe His Lys Glu
    210                 215                 220

Met Ser Lys Leu Asn Gln Asn Leu Asn Asp Val Leu Val Gly Leu Glu
225                 230                 235                 240

Lys Gln His Gly Ser Asn Thr Phe Thr Val Lys Ala Gln Pro Ser Asp
                245                 250                 255

Asn Ala Pro Ala Lys Gly Asn Lys Ser Pro Ser Pro Asp Gly Ser
            260                 265                 270

Pro Ala Ala Thr Pro Glu Ile Arg Val Asn His Glu Pro Glu Pro Ala
        275                 280                 285
```

```
Gly Gly Ala Thr Pro Gly Ala Thr Leu Pro Lys Ser Pro Ser Gln Pro
        290                 295                 300
Ala Glu Ala Ser Glu Val Ala Gly Gly Thr Gln Pro Ala Ala Gly Ala
305                 310                 315                 320
Gln Glu Pro Gly Glu Thr Ala Ala Ser Glu Ala Ala Ser Ser Ser Leu
                325                 330                 335
Pro Ala Val Val Val Glu Thr Phe Pro Ala Thr Val Asn Gly Thr Val
                340                 345                 350
Glu Gly Gly Ser Gly Ala Gly Arg Leu Asp Leu Pro Pro Gly Phe Met
            355                 360                 365
Phe Lys Val Gln Ala Gln His Asp Tyr Thr Ala Thr Asp Thr Asp Glu
        370                 375                 380
Leu Gln Leu Lys Ala Gly Asp Val Val Leu Val Ile Pro Phe Gln Asn
385                 390                 395                 400
Pro Glu Glu Gln Asp Glu Gly Trp Leu Met Gly Val Lys Glu Ser Asp
                405                 410                 415
Trp Asn Gln His Lys Leu Glu Lys Cys Arg Gly Val Phe Pro Glu
            420                 425                 430
Asn Phe Thr Glu Arg Val Pro
        435

<210> SEQ ID NO 5
<211> LENGTH: 6417
<212> TYPE: DNA
<213> ORGANISM: Homo sapiens

<400> SEQUENCE: 5
atggtcaatg agaatacgag gatgtacatt ccagaggaaa accaccaagg ttccaactat      60
gggagcccac gccccgccca tgccaacatg aatgccaatg cggcagcggg gctggccct    120
gagcacatcc ccaccccggg ggctgccctg tcgtggcagg cggccatcga cgcagcccgg    180
caggctaagc tgatgggcag cgctggcaat gcgaccatct ccacagtcag ctccacgcag    240
cggaagcggc agcaatatgg gaaacccaag aagcagggca gcaccacggc cacacgcccg    300
cccgagccc  tgctctgcct gaccctgaag aaccccatcc ggagggcctg catcagcatt    360
gtcgaatgga aaccattga aataattatt ttactgacta tttttgccaa ttgtgtggcc    420
ttagcgatct atattccctt ccagaagat gattccaacg ccaccaattc caacctggaa    480
cgagtggaat atctctttct cataattttt acggtggaag cgttttaaa agtaatcgcc    540
tatggactcc tctttcaccc caatgcctac ctccgcaacg gctggaacct actagatttt    600
ataattgtgg ttgtgggct ttttagtgca attttagaac aagcaaccaa agcagatggg    660
gcaaacgctc tcggagggaa aggggccgga tttgatgtga aggcgctgag ggccttccgc    720
gtgctgcgcc ccctgcggct ggtgtccgga gtcccaagtc tccaggtggt cctgaattcc    780
atcatcaagg ccatggtccc cctgctgcac atcgccctgc ttgtgctgtt tgtcatcatc    840
atctacgcca tcatcggctt ggagctcttc atggggaaga tgcacaagac ctgctacaac    900
caggagggca tagcagatgt tccagcagaa gatgaccctt cccttgtgc  gctggaaacg    960
ggccacgggc ggcagtgcca gaacggcacg gtgtgcaagc ccggctggga tggtcccaag   1020
cacggcatca ccaactttga caactttgcc ttcgccatgc tcacggtgtt ccagtgcatc   1080
accatggagg gctggacgga cgtgctgtac tgggtcaatg atgccgtagg aagggactgg   1140
ccctggatct atttgttac actaatcatc ataggtcat ttttgtact taacttggtt    1200
ctcggtgtgc ttagcggaga gttttccaaa gagagggaga aggccaaggc ccggggagat   1260
```

```
ttccagaagc tgcgggagaa gcagcagcta gaagaggatc tcaaaggcta cctggattgg      1320
atcactcagg ccgaagacat cgatcctgag aatgaggacg aaggcatgga tgaggagaag      1380
ccccgaaaca tgagcatgcc caccagtgag accgagtccg tcaacaccga aaacgtggct      1440
ggaggtgaca tcgagggaga aaactgcggg gccaggctgg cccaccggat ctccaagtca      1500
aagttcagcc gctactggcg ccggtggaat cggttctgca aaggaagtg ccgcgccgca       1560 gtcaagtcta tgtcttcta ctggctggtg attttcctgg tgttcctcaa cacgctcacc       1620
attgcctctg agcactacaa ccagcccaac tggctcacag aagtccaaga cacggcaaac      1680
aaggccctgc tggcccctgtt cacggcagag atgctcctga agatgtacag cctgggcctg     1740
caggcctact tcgtgtccct cttcaaccgc tttgactgct tcgtcgtgtg tggcggcatc      1800
ctggagacca tcctggtgga gaccaagatc atgtccccac tgggcatctc cgtgctcaga     1860
tgcgtccggc tgctgaggat tttcaagatc acgaggtact ggaactcctt gagcaacctg      1920
gtggcatcct tgctgaactc tgtgcgctcc atcgcctccc tgctccttct cctcttcctc      1980
ttcatcatca tcttctccct cctggggatg cagctctttg gaggaaagtt caactttgat      2040
gagatgcaga cccggaggag cacattcgat aacttccccc agtccctcct cactgtgttt      2100
cagatcctga ccggggagga ctggaattcg gtgatgtatg atgggatcat ggcttatggc      2160
ggcccctctt ttccagggat gttagtctgt atttacttca tcatcctctt catctgtgga      2220
aactatatcc tactgaatgt gttcttggcc attgctgtgg acaacctggc tgatgctgag      2280
agcctcacat ctgcccaaaa ggaggaggaa gaggagaagg agagaaagaa gctggccagg      2340
actgccagcc cagagaagaa acaagagttg gtggagaagc cggcagtggg ggaatccaag      2400
gaggagaaga ttgagctgaa atccatcacg gctgacggag agtctccacc cgccaccaag      2460
atcaacatgg atgacctcca gcccaatgaa atgaggaata agagccccta ccccaaccca      2520
gaaactacag gagaagagga tgaggaggag ccagagatgc ctgtcggccc tcgcccacga      2580
ccactctctg agcttcacct taaggaaaag gcagtgccca tgccagaagc cagcgcgttt      2640
ttcatcttca gctctaacaa caggtttcgc ctccagtgcc accgcattgt caatgacacg      2700
atcttcacca acctgatcct cttcttcatt ctgctcagca gcatttccct ggctgctgag      2760
gacccggtcc agcacacctc cttcaggaac catattctgt tttattttga tattgttttt      2820
accaccattt tcaccattga aattgctctg aagatgactg cttatgggc tttcttgcac      2880 aagggttctt tctgccggaa ctacttcaac atcctggacc tgctggtggt cagcgtgtcc      2940
ctcatctcct ttggcatcca gtccagtgca atcaatgtcg tgaagatctt gcgagtcctg      3000
cgagtactca ggccctgag ggccatcaac agggccaagg ggctaaagca tgtggttcag      3060
tgtgtgtttg tcgccatccg gaccatcggg aacatcgtga ttgtcaccac cctgctgcag      3120
ttcatgtttg cctgcatcgg ggtccagctc ttcaagggaa agctgtacac ctgttcagac      3180
agttccaagc agacagaggc ggaatgcaag ggcaactaca tcacgtacaa agacggggag      3240
gttgaccacc ccatcatcca accccgcagc tgggagaaca gcaagtttga ctttgacaat      3300
gttctggcag ccatgatggc cctcttcacc gtctccacct tcgaagggtg gccagagctg      3360
ctgtaccgct ccatcgactc ccacacggaa gacaagggcc ccatctacaa ctaccgtgtg      3420
gagatctcca tcttcttcat catctacatc atcatcatcg ccttcttcat gatgaacatc      3480
ttcgtgggct tcgtcatcgt cacctttcag gagcaggggg agcaggagta caagaactgt      3540
gagctggaca agaaccagcg acagtgcgtg gaatacgccc tcaaggcccg cccctgcgg      3600
```

```
aggtacatcc ccaagaacca gcaccagtac aaagtgtggt acgtggtcaa ctccacctac    3660
ttcgagtacc tgatgttcgt cctcatcctg ctcaacacca tctgcctggc catgcagcac    3720
tacggccaga gctgcctgtt caaaatcgcc atgaacatcc tcaacatgct cttcactggc    3780
ctcttcaccg tggagatgat cctgaagctc attgccttca acccaagca ctatttctgt     3840 gatgcatgga atacatttga cgccttgatt gttgtgggta gcattgttga tatagcaatc    3900
accgaggtaa acccagctga acatacccaa tgctctccct ctatgaacgc agaggaaaac    3960
tcccgcatct ccatcacctt cttccgcctg ttccgggtca tgcgtctggt gaagctgctg    4020
agccgtgggg agggcatccg gacgctgctg tggaccttca tcaagtcctt ccaggccctg    4080
ccctatgtgg ccctcctgat cgtgatgctg ttcttcatct acgcggtgat cgggatgcag    4140
gtgtttggga aaattgccct gaatgatacc acagagatca accggaacaa caactttcag    4200
accttccccc aggccgtgct gctcctcttc aggtgtgcca ccggggaggc ctggcaggac    4260
atcatgctgg cctgcatgcc aggcaagaag tgtgccccag agtccgagcc cagcaacagc    4320
acggagggtg aaacaccctg tggtagcagc tttgctgtct tctacttcat cagcttctac    4380
atgctctgtg ccttcctgat catcaacctc tttgtagctg tcatcatgga aactttgac     4440 tacctgacaa gggactggtc catccttggt ccccaccacc tggatgagtt taaaagaatc    4500
tgggcagagt atgaccctga agccaagggt cgtatcaaac acctggatgt ggtgacccte    4560 ctccggcgga ttcagccgcc actaggtttt gggaagctgt gccctcaccg cgtggcttgc    4620
aaacgcctgg tctccatgaa catgcctctg aacagcgacg ggacagtcat gttcaatgcc    4680
accctgtttg ccctggtcag gacggccctg aggatcaaaa cagaagggaa cctagaacaa    4740
gccaatgagg agctgcgggc gatcatcaag aagatctgga gcggaccag catgaagctg     4800 ctggaccagg tggtgccccc tgcaggtgat gatgaggtca ccgttggcaa gttctacgcc    4860
acgttcctga tccaggagta cttccggaag ttcaagaagc gcaaagagca gggccttgtg    4920
ggcaagccct cccagaggaa cgcgctgtct ctgcaggctg gcttgcgcac actgcatgac    4980
atcgggcctg agatccgacg ggccatctct ggagatctca ccgctgagga ggagctggac    5040
aaggccatga aggaggctgt gtccgctgct tctgaagatg acatcttcag agggccggt    5100 ggcctgttcg gcaaccacgt cagctactac caaagcgacg gccggagcgc cttcccccag    5160
accttcacca ctcagcgccc gctgcacatc aacaaggcgg gcagcagcca gggcgacact    5220
gagtcgccat cccacgagaa gctggtggac tccaccttca ccccgagcag ctactcgtcc    5280
accggctcca cgccaacat caacaacgcc aacaacaccg cctgggtcg cctccctcgc      5340 cccgccggct accccagcac ggtcagcact gtggagggcc acgggccccc cttgtcccct    5400
gccatccggg tgcaggaggt ggcgtggaag ctcagctcca caggtgcca ctcccgggag     5460 agccaggcag ccatggcggg tcaggaggag acgtctcagg atgagaccta tgaagtgaag    5520
atgaaccatg acacggaggc ctgcagtgag cccagcctgc tctccacaga gatgctctcc    5580
taccaggatg acgaaaatcg gcaactgacg ctcccagagg aggacaagag ggacatccgg    5640
caatctccga gaggggttt cctccgctct gcctcactag gtcgaagggc ctccttccac     5700
ctggaatgtc tgaagcgaca gaaggaccga ggggagaca tctctcagaa gacagtcctg    5760
cccttgcatc tggttcatca tcaggcattg gcagtggcag gcctgagccc cctcctccag    5820
agaagccatt cccctgcctc attccctagg ccttttgcca ccccaccagc cacacctggc    5880
agccgaggct ggccccaca gcccgtcccc acctgcgcgc ttgaggggt cgagtccagt      5940 gagaaactca acagcagctt cccatccatc cactgcggct cctgggctga gaccaccccc    6000
```

-continued

```
ggtggcgggg gcagcagcgc cgcccggaga gtccggcccg tctccctcat ggtgcccagc    6060
caggctgggg ccccagggag gcagttccac ggcagtgcca gcagcctggt ggaagcggtc    6120
ttgatttcag aaggactggg gcagtttgct caagatccca agttcatcga ggtcaccacc    6180
caggagctgg ccgacgcctg cgacatgacc atagaggaga tggagagcgc ggccgacaac    6240
atcctcagcg ggggcgcccc acagagcccc aatggcgccc tcttacccct tgtgaactgc    6300
agggacgcgg ggcaggaccg agccgggggc gaagaggacg cgggctgtgt gcgcgcgcgg    6360
ggtcgaccga gtgaggagga gctccaggac agcagggtct acgtcagcag cctgtag      6417
```

<210> SEQ ID NO 6
<211> LENGTH: 2138
<212> TYPE: PRT
<213> ORGANISM: Homo sapiens

<400> SEQUENCE: 6

```
Met Val Asn Glu Asn Thr Arg Met Tyr Ile Pro Glu Glu Asn His Gln
  1               5                  10                  15

Gly Ser Asn Tyr Gly Ser Pro Arg Pro Ala His Ala Asn Met Asn Ala
             20                  25                  30

Asn Ala Ala Ala Gly Leu Ala Pro Glu His Ile Pro Thr Pro Gly Ala
         35                  40                  45

Ala Leu Ser Trp Gln Ala Ala Ile Asp Ala Ala Arg Gln Ala Lys Leu
     50                  55                  60

Met Gly Ser Ala Gly Asn Ala Thr Ile Ser Thr Val Ser Ser Thr Gln
 65                  70                  75                  80

Arg Lys Arg Gln Gln Tyr Gly Lys Pro Lys Lys Gln Gly Ser Thr Thr
                 85                  90                  95

Ala Thr Arg Pro Pro Arg Ala Leu Leu Cys Leu Thr Leu Lys Asn Pro
            100                 105                 110

Ile Arg Arg Ala Cys Ile Ser Ile Val Glu Trp Lys Pro Phe Glu Ile
        115                 120                 125

Ile Ile Leu Leu Thr Ile Phe Ala Asn Cys Val Ala Leu Ala Ile Tyr
    130                 135                 140

Ile Pro Phe Pro Glu Asp Asp Ser Asn Ala Thr Asn Ser Asn Leu Glu
145                 150                 155                 160

Arg Val Glu Tyr Leu Phe Leu Ile Ile Phe Thr Val Glu Ala Phe Leu
                165                 170                 175

Lys Val Ile Ala Tyr Gly Leu Leu Phe His Pro Asn Ala Tyr Leu Arg
            180                 185                 190

Asn Gly Trp Asn Leu Leu Asp Phe Ile Ile Val Val Gly Leu Phe
        195                 200                 205

Ser Ala Ile Leu Glu Gln Ala Thr Lys Ala Asp Gly Ala Asn Ala Leu
    210                 215                 220

Gly Gly Lys Gly Ala Gly Phe Asp Val Lys Ala Leu Arg Ala Phe Arg
225                 230                 235                 240

Val Leu Arg Pro Leu Arg Leu Val Ser Gly Val Pro Ser Leu Gln Val
                245                 250                 255

Val Leu Asn Ser Ile Ile Lys Ala Met Val Pro Leu Leu His Ile Ala
            260                 265                 270

Leu Leu Val Leu Phe Val Ile Ile Ile Tyr Ala Ile Ile Gly Leu Glu
        275                 280                 285

Leu Phe Met Gly Lys Met His Lys Thr Cys Tyr Asn Gln Glu Gly Ile
    290                 295                 300
```

```
Ala Asp Val Pro Ala Glu Asp Pro Ser Pro Cys Ala Leu Glu Thr
305                 310                 315                 320

Gly His Gly Arg Gln Cys Gln Asn Gly Thr Val Cys Lys Pro Gly Trp
        325                 330                 335

Asp Gly Pro Lys His Gly Ile Thr Asn Phe Asp Asn Phe Ala Phe Ala
            340                 345                 350

Met Leu Thr Val Phe Gln Cys Ile Thr Met Glu Gly Trp Thr Asp Val
                355                 360                 365

Leu Tyr Trp Val Asn Asp Ala Val Gly Arg Asp Trp Pro Trp Ile Tyr
        370                 375                 380

Phe Val Thr Leu Ile Ile Ile Gly Ser Phe Phe Val Leu Asn Leu Val
385                 390                 395                 400

Leu Gly Val Leu Ser Gly Glu Phe Ser Lys Glu Arg Glu Lys Ala Lys
                405                 410                 415

Ala Arg Gly Asp Phe Gln Lys Leu Arg Glu Lys Gln Gln Leu Glu Glu
            420                 425                 430

Asp Leu Lys Gly Tyr Leu Asp Trp Ile Thr Gln Ala Glu Asp Ile Asp
        435                 440                 445

Pro Glu Asn Glu Asp Glu Gly Met Asp Glu Glu Lys Pro Arg Asn Met
450                 455                 460

Ser Met Pro Thr Ser Glu Thr Glu Ser Val Asn Thr Glu Asn Val Ala
465                 470                 475                 480

Gly Gly Asp Ile Glu Gly Glu Asn Cys Gly Ala Arg Leu Ala His Arg
                485                 490                 495

Ile Ser Lys Ser Lys Phe Ser Arg Tyr Trp Arg Arg Trp Asn Arg Phe
            500                 505                 510

Cys Arg Arg Lys Cys Arg Ala Ala Val Lys Ser Asn Val Phe Tyr Trp
        515                 520                 525

Leu Val Ile Phe Leu Val Phe Leu Asn Thr Leu Thr Ile Ala Ser Glu
        530                 535                 540

His Tyr Asn Gln Pro Asn Trp Leu Thr Glu Val Gln Asp Thr Ala Asn
545                 550                 555                 560

Lys Ala Leu Leu Ala Leu Phe Thr Ala Glu Met Leu Leu Lys Met Tyr
                565                 570                 575

Ser Leu Gly Leu Gln Ala Tyr Phe Val Ser Leu Phe Asn Arg Phe Asp
        580                 585                 590

Cys Phe Val Val Cys Gly Gly Ile Leu Glu Thr Ile Leu Val Glu Thr
            595                 600                 605

Lys Ile Met Ser Pro Leu Gly Ile Ser Val Leu Arg Cys Val Arg Leu
        610                 615                 620

Leu Arg Ile Phe Lys Ile Thr Arg Tyr Trp Asn Ser Leu Ser Asn Leu
625                 630                 635                 640

Val Ala Ser Leu Leu Asn Ser Val Arg Ser Ile Ala Ser Leu Leu Leu
                645                 650                 655

Leu Leu Phe Leu Phe Ile Ile Ile Phe Ser Leu Leu Gly Met Gln Leu
            660                 665                 670

Phe Gly Gly Lys Phe Asn Phe Asp Glu Met Gln Thr Arg Arg Ser Thr
        675                 680                 685

Phe Asp Asn Phe Pro Gln Ser Leu Leu Thr Val Phe Gln Ile Leu Thr
        690                 695                 700

Gly Glu Asp Trp Asn Ser Val Met Tyr Asp Gly Ile Met Ala Tyr Gly
705                 710                 715                 720
```

```
Gly Pro Ser Phe Pro Gly Met Leu Val Cys Ile Tyr Phe Ile Ile Leu
                725                 730                 735

Phe Ile Cys Gly Asn Tyr Ile Leu Leu Asn Val Phe Leu Ala Ile Ala
            740                 745                 750

Val Asp Asn Leu Ala Asp Ala Glu Ser Leu Thr Ser Ala Gln Lys Glu
        755                 760                 765

Glu Glu Glu Glu Lys Glu Arg Lys Lys Leu Ala Arg Thr Ala Ser Pro
    770                 775                 780

Glu Lys Lys Gln Glu Leu Val Glu Lys Pro Ala Val Gly Glu Ser Lys
785                 790                 795                 800

Glu Glu Lys Ile Glu Leu Lys Ser Ile Thr Ala Asp Gly Glu Ser Pro
                805                 810                 815

Pro Ala Thr Lys Ile Asn Met Asp Asp Leu Gln Pro Asn Glu Asn Glu
            820                 825                 830

Asp Lys Ser Pro Tyr Pro Asn Pro Glu Thr Thr Gly Glu Glu Asp Glu
        835                 840                 845

Glu Glu Pro Glu Met Pro Val Gly Pro Arg Pro Arg Pro Leu Ser Glu
    850                 855                 860

Leu His Leu Lys Glu Lys Ala Val Pro Met Pro Glu Ala Ser Ala Phe
865                 870                 875                 880

Phe Ile Phe Ser Ser Asn Asn Arg Phe Arg Leu Gln Cys His Arg Ile
                885                 890                 895

Val Asn Asp Thr Ile Phe Thr Asn Leu Ile Leu Phe Phe Ile Leu Leu
            900                 905                 910

Ser Ser Ile Ser Leu Ala Ala Glu Asp Pro Val Gln His Thr Ser Phe
        915                 920                 925

Arg Asn His Ile Leu Phe Tyr Phe Asp Ile Val Phe Thr Thr Ile Phe
    930                 935                 940

Thr Ile Glu Ile Ala Leu Lys Met Thr Ala Tyr Gly Ala Phe Leu His
945                 950                 955                 960

Lys Gly Ser Phe Cys Arg Asn Tyr Phe Asn Ile Leu Asp Leu Leu Val
                965                 970                 975

Val Ser Val Ser Leu Ile Ser Phe Gly Ile Gln Ser Ser Ala Ile Asn
            980                 985                 990

Val Val Lys Ile Leu Arg Val Leu Arg Val Leu Arg Pro Leu Arg Ala
        995                 1000                1005

Ile Asn Arg Ala Lys Gly Leu Lys His Val Val Gln Cys Val Phe Val
    1010                1015                1020

Ala Ile Arg Thr Ile Gly Asn Ile Val Ile Val Thr Thr Leu Leu Gln
1025                1030                1035                1040

Phe Met Phe Ala Cys Ile Gly Val Gln Leu Phe Lys Gly Lys Leu Tyr
                1045                1050                1055

Thr Cys Ser Asp Ser Ser Lys Gln Thr Glu Ala Glu Cys Lys Gly Asn
            1060                1065                1070

Tyr Ile Thr Tyr Lys Asp Gly Val Asp His Pro Ile Ile Gln Pro
        1075                1080                1085

Arg Ser Trp Glu Asn Ser Lys Phe Asp Phe Asp Asn Val Leu Ala Ala
    1090                1095                1100

Met Met Ala Leu Phe Thr Val Ser Thr Phe Glu Gly Trp Pro Glu Leu
1105                1110                1115                1120

Leu Tyr Arg Ser Ile Asp Ser His Thr Glu Asp Lys Gly Pro Ile Tyr
                1125                1130                1135

Asn Tyr Arg Val Glu Ile Ser Ile Phe Phe Ile Ile Tyr Ile Ile Ile
```

-continued

```
            1140                1145                 1150
Ile Ala Phe Phe Met Met Asn Ile Phe Val Gly Phe Ile Val Thr
            1155                1160                 1165
Phe Gln Glu Gln Gly Glu Gln Glu Tyr Lys Asn Cys Glu Leu Asp Lys
    1170                1175                1180
Asn Gln Arg Gln Cys Val Glu Tyr Ala Leu Lys Ala Arg Pro Leu Arg
1185                1190                1195                1200
Arg Tyr Ile Pro Lys Asn Gln His Gln Tyr Lys Val Trp Tyr Val Val
                1205                1210                1215
Asn Ser Thr Tyr Phe Glu Tyr Leu Met Phe Val Leu Ile Leu Leu Asn
            1220                1225                1230
Thr Ile Cys Leu Ala Met Gln His Tyr Gly Gln Ser Cys Leu Phe Lys
            1235                1240                1245
Ile Ala Met Asn Ile Leu Asn Met Leu Phe Thr Gly Leu Phe Thr Val
            1250                1255                1260
Glu Met Ile Leu Lys Leu Ile Ala Phe Lys Pro Lys His Tyr Phe Cys
1265                1270                1275                1280
Asp Ala Trp Asn Thr Phe Asp Ala Leu Ile Val Val Gly Ser Ile Val
                1285                1290                1295
Asp Ile Ala Ile Thr Glu Val Asn Pro Ala Glu His Thr Gln Cys Ser
            1300                1305                1310
Pro Ser Met Asn Ala Glu Glu Asn Ser Arg Ile Ser Ile Thr Phe Phe
            1315                1320                1325
Arg Leu Phe Arg Val Met Arg Leu Val Lys Leu Leu Ser Arg Gly Glu
            1330                1335                1340
Gly Ile Arg Thr Leu Leu Trp Thr Phe Ile Lys Ser Phe Gln Ala Leu
1345                1350                1355                1360
Pro Tyr Val Ala Leu Leu Ile Val Met Leu Phe Phe Ile Tyr Ala Val
                1365                1370                1375
Ile Gly Met Gln Val Phe Gly Lys Ile Ala Leu Asn Asp Thr Thr Glu
            1380                1385                1390
Ile Asn Arg Asn Asn Asn Phe Gln Thr Phe Pro Gln Ala Val Leu Leu
            1395                1400                1405
Leu Phe Arg Cys Ala Thr Gly Glu Ala Trp Gln Asp Ile Met Leu Ala
            1410                1415                1420
Cys Met Pro Gly Lys Lys Cys Ala Pro Glu Ser Glu Pro Ser Asn Ser
1425                1430                1435                1440
Thr Glu Gly Glu Thr Pro Cys Gly Ser Ser Phe Ala Val Phe Tyr Phe
                1445                1450                1455
Ile Ser Phe Tyr Met Leu Cys Ala Phe Leu Ile Ile Asn Leu Phe Val
            1460                1465                1470
Ala Val Ile Met Asp Asn Phe Asp Tyr Leu Thr Arg Asp Trp Ser Ile
            1475                1480                1485
Leu Gly Pro His His Leu Asp Glu Phe Lys Arg Ile Trp Ala Glu Tyr
            1490                1495                1500
Asp Pro Glu Ala Lys Gly Arg Ile Lys His Leu Asp Val Val Thr Leu
1505                1510                1515                1520
Leu Arg Arg Ile Gln Pro Pro Leu Gly Phe Gly Lys Leu Cys Pro His
                1525                1530                1535
Arg Val Ala Cys Lys Arg Leu Val Ser Met Asn Met Pro Leu Asn Ser
            1540                1545                1550
Asp Gly Thr Val Met Phe Asn Ala Thr Leu Phe Ala Leu Val Arg Thr
            1555                1560                1565
```

```
Ala Leu Arg Ile Lys Thr Glu Gly Asn Leu Glu Gln Ala Asn Glu Glu
    1570                1575                1580

Leu Arg Ala Ile Ile Lys Lys Ile Trp Lys Arg Thr Ser Met Lys Leu
1585                1590                1595                1600

Leu Asp Gln Val Val Pro Pro Ala Gly Asp Asp Glu Val Thr Val Gly
                1605                1610                1615

Lys Phe Tyr Ala Thr Phe Leu Ile Gln Glu Tyr Phe Arg Lys Phe Lys
            1620                1625                1630

Lys Arg Lys Glu Gln Gly Leu Val Gly Lys Pro Ser Gln Arg Asn Ala
        1635                1640                1645

Leu Ser Leu Gln Ala Gly Leu Arg Thr Leu His Asp Ile Gly Pro Glu
    1650                1655                1660

Ile Arg Arg Ala Ile Ser Gly Asp Leu Thr Ala Glu Glu Leu Asp
1665                1670                1675                1680

Lys Ala Met Lys Glu Ala Val Ser Ala Ala Ser Glu Asp Asp Ile Phe
                1685                1690                1695

Arg Arg Ala Gly Gly Leu Phe Gly Asn His Val Ser Tyr Tyr Gln Ser
            1700                1705                1710

Asp Gly Arg Ser Ala Phe Pro Gln Thr Phe Thr Thr Gln Arg Pro Leu
        1715                1720                1725

His Ile Asn Lys Ala Gly Ser Ser Gln Gly Asp Thr Glu Ser Pro Ser
    1730                1735                1740

His Glu Lys Leu Val Asp Ser Thr Phe Thr Pro Ser Ser Tyr Ser Ser
1745                1750                1755                1760

Thr Gly Ser Asn Ala Asn Ile Asn Asn Ala Asn Asn Thr Ala Leu Gly
                1765                1770                1775

Arg Leu Pro Arg Pro Ala Gly Tyr Pro Ser Thr Val Ser Thr Val Glu
            1780                1785                1790

Gly His Gly Pro Pro Leu Ser Pro Ala Ile Arg Val Gln Glu Val Ala
        1795                1800                1805

Trp Lys Leu Ser Ser Asn Arg Cys His Ser Arg Glu Ser Gln Ala Ala
    1810                1815                1820

Met Ala Gly Gln Glu Glu Thr Ser Gln Asp Glu Thr Tyr Glu Val Lys
1825                1830                1835                1840

Met Asn His Asp Thr Glu Ala Cys Ser Glu Pro Ser Leu Leu Ser Thr
                1845                1850                1855

Glu Met Leu Ser Tyr Gln Asp Asp Glu Asn Arg Gln Leu Thr Leu Pro
            1860                1865                1870

Glu Glu Asp Lys Arg Asp Ile Arg Gln Ser Pro Lys Arg Gly Phe Leu
        1875                1880                1885

Arg Ser Ala Ser Leu Gly Arg Arg Ala Ser Phe His Leu Glu Cys Leu
    1890                1895                1900

Lys Arg Gln Lys Asp Arg Gly Gly Asp Ile Ser Gln Lys Thr Val Leu
1905                1910                1915                1920

Pro Leu His Leu Val His His Gln Ala Leu Ala Val Ala Gly Leu Ser
                1925                1930                1935

Pro Leu Leu Gln Arg Ser His Ser Pro Ala Ser Phe Pro Arg Pro Phe
            1940                1945                1950

Ala Thr Pro Pro Ala Thr Pro Gly Ser Arg Gly Trp Pro Pro Gln Pro
        1955                1960                1965

Val Pro Thr Leu Arg Leu Glu Gly Val Glu Ser Ser Glu Lys Leu Asn
    1970                1975                1980
```

```
Ser Ser Phe Pro Ser Ile His Cys Gly Ser Trp Ala Glu Thr Thr Pro
1985                1990                1995                2000

Gly Gly Gly Gly Ser Ser Ala Ala Arg Arg Val Arg Pro Val Ser Leu
            2005                2010                2015

Met Val Pro Ser Gln Ala Gly Ala Pro Gly Arg Gln Phe His Gly Ser
        2020                2025                2030

Ala Ser Ser Leu Val Glu Ala Val Leu Ile Ser Glu Gly Leu Gly Gln
            2035                2040                2045

Phe Ala Gln Asp Pro Lys Phe Ile Glu Val Thr Thr Gln Glu Leu Ala
        2050                2055                2060

Asp Ala Cys Asp Met Thr Ile Glu Glu Met Glu Ser Ala Ala Asp Asn
2065                2070                2075                2080

Ile Leu Ser Gly Gly Ala Pro Gln Ser Pro Asn Gly Ala Leu Leu Pro
            2085                2090                2095

Phe Val Asn Cys Arg Asp Ala Gly Gln Asp Arg Ala Gly Gly Glu Glu
        2100                2105                2110

Asp Ala Gly Cys Val Arg Ala Arg Gly Arg Pro Ser Glu Glu Glu Leu
            2115                2120                2125

Gln Asp Ser Arg Val Tyr Val Ser Ser Leu
        2130                2135

<210> SEQ ID NO 7
<211> LENGTH: 20
<212> TYPE: DNA
<213> ORGANISM: Artificial Sequence
<220> FEATURE:
<223> OTHER INFORMATION: Synthetic probe

<400> SEQUENCE: 7
cagagcggcc tggcctcgct                                              20

<210> SEQ ID NO 8
<211> LENGTH: 26
<212> TYPE: DNA
<213> ORGANISM: Artificial Sequence
<220> FEATURE:
<223> OTHER INFORMATION: Synthetic probe

<400> SEQUENCE: 8
tgagcttgtt tgtgtccctg tgggtg                                       26

<210> SEQ ID NO 9
<211> LENGTH: 24
<212> TYPE: DNA
<213> ORGANISM: Artificial Sequence
<220> FEATURE:
<223> OTHER INFORMATION: Synthetic probe

<400> SEQUENCE: 9
cactggcatt gccatcctta cggg                                         24

<210> SEQ ID NO 10
<211> LENGTH: 24
<212> TYPE: DNA
<213> ORGANISM: Artificial Sequence
<220> FEATURE:
<223> OTHER INFORMATION: Synthetic probe

<400> SEQUENCE: 10
atggcaaatg ctggacccaa caca                                         24
```